(12) United States Patent
Bengtsson et al.

(10) Patent No.: US 12,144,968 B2
(45) Date of Patent: Nov. 19, 2024

(54) FLOW COMMUNICATION UNIT WITH UNCONNECTED AND CONNECTED CONFIGURATION

(71) Applicant: Novo Nordisk A/S, Bagsvaerd (DK)

(72) Inventors: Henrik Bengtsson, Taastrup (DK); Brian Jensen, Broenshoej (DK); Bo Kvolsbjerg, Helsingoer (DK)

(73) Assignee: Novo Nordisk A/S, Bagsvaerd (DK)

( * ) Notice: Subject to any disclaimer, the term of this patent is extended or adjusted under 35 U.S.C. 154(b) by 928 days.

(21) Appl. No.: 17/045,708

(22) PCT Filed: Jan. 10, 2019

(86) PCT No.: PCT/EP2019/050555
§ 371 (c)(1),
(2) Date: Oct. 6, 2020

(87) PCT Pub. No.: WO2019/197061
PCT Pub. Date: Oct. 17, 2019

(65) Prior Publication Data
US 2021/0030966 A1 Feb. 4, 2021

(30) Foreign Application Priority Data
Apr. 13, 2018 (EP) .................................... 18167233

(51) Int. Cl.
*A61M 5/24* (2006.01)
*A61M 5/28* (2006.01)
(Continued)

(52) U.S. Cl.
CPC .......... *A61M 5/2459* (2013.01); *A61M 39/24* (2013.01)

(58) Field of Classification Search
CPC .... A61M 5/2459; A61M 39/24; A61M 5/345; A61M 5/24; A61M 5/28; A61M 5/286;
(Continued)

(56) References Cited

U.S. PATENT DOCUMENTS 3,354,881 A 11/1967 Bloch
4,133,457 A 1/1979 Klassen
(Continued)

FOREIGN PATENT DOCUMENTS

CN 1744871 A 3/2006
CN 1764798 A 4/2006
(Continued)

*Primary Examiner* — Robert J Utama
*Assistant Examiner* — Hamza A Darb
(74) *Attorney, Agent, or Firm* — Wesley Nicolas

(57) ABSTRACT

A flow communication unit (240, 540, 640, 740, 840, 940, 1040, 1140, 1240) for establishing flow communication from a multi-use drug delivery device adapted for extended use, to a flow conducting device, wherein the drug delivery device comprises a reservoir comprising multiple doses of a liquid drug formulation, wherein the reservoir is adapted to pressurize the liquid drug formulation, wherein the flow conducting device (230) is adapted for conducting the drug to the subcutaneous tissue of a subject, wherein the flow communication unit is adapted for being in an unconnected and a connected configuration, whereby the flow communication unit (240, 540, 640, 740, 840, 940, 1040, 1140, 1240) is adapted to enable the extended use of the multi-use drug delivery device.

14 Claims, 27 Drawing Sheets

(51) Int. Cl.
*A61M 5/34* (2006.01)
*A61M 39/24* (2006.01)

(58) Field of Classification Search
CPC .... A61M 2005/3106; A61M 2005/312; A61M 2005/3128; A61M 2039/242; A61J 1/062; A61J 1/201; A61J 1/2037
See application file for complete search history.

(56) References Cited

U.S. PATENT DOCUMENTS

| | | | |
|---|---|---|---|
| 4,919,658 | A | 4/1990 | Badia |
| 5,340,359 | A | 8/1994 | Segura Badia |
| 6,010,485 | A | 1/2000 | Buch-Rasmussen et al. |
| 6,871,838 | B2 | 3/2005 | Raines et al. |
| 7,291,133 | B1 | 11/2007 | Kindler et al. |
| 7,981,081 | B2 | 7/2011 | Marsh et al. |
| 8,066,692 | B2 | 11/2011 | Simpson et al. |
| 8,863,993 | B2 | 10/2014 | Donnette et al. |
| 8,863,998 | B2 | 10/2014 | Painchaud et al. |
| 9,241,828 | B2 | 1/2016 | Pardes et al. |
| 9,408,971 | B2 | 8/2016 | Carlyon |
| 10,112,018 | B2 | 10/2018 | Cowe |
| 2004/0158204 | A1 | 8/2004 | Reboul |
| 2005/0043684 | A1 | 2/2005 | Basta et al. |
| 2005/0113750 | A1 | 5/2005 | Targell |
| 2009/0152306 | A1* | 6/2009 | Pardes .............. A61M 15/0016 137/846 |
| 2011/0168170 | A1 | 7/2011 | Patton et al. |
| 2011/0208128 | A1 | 8/2011 | Wu et al. |
| 2013/0018323 | A1 | 1/2013 | Boyd et al. |
| 2014/0303601 | A1* | 10/2014 | Fangrow .............. A61M 39/10 604/537 |
| 2016/0001014 | A1* | 1/2016 | Eilertsen ............. A61M 5/3291 604/198 |
| 2020/0246547 | A1 | 8/2020 | Glenting et al. |
| 2021/0077727 | A1 | 3/2021 | Bengtsson et al. |

FOREIGN PATENT DOCUMENTS

| | | |
|---|---|---|
| CN | 2910250 Y | 6/2007 |
| CN | 104703640 A | 6/2015 |
| CN | 102844073 | 11/2015 |
| EP | 0716860 A3 | 11/1996 |
| EP | 0795342 A2 | 9/1997 |
| EP | 1948523 A1 | 7/2008 |
| EP | 2704773 A1 | 3/2014 |
| GB | 706150 A | 3/1954 |
| GB | 739753 A | 11/1955 |
| JP | 2001501504 A | 2/2001 |
| WO | 2007056233 A1 | 5/2007 |
| WO | 2012152703 A1 | 11/2012 |
| WO | 2013112486 A1 | 8/2013 |
| WO | 2014009444 A1 | 1/2014 |
| WO | 2014064100 A1 | 5/2014 |
| WO | 2014125067 A1 | 8/2014 |
| WO | 2015155229 A1 | 10/2015 |
| WO | 2015173151 A1 | 11/2015 |
| WO | 2015177082 A1 | 11/2015 |
| WO | 2016061062 A1 | 4/2016 |
| WO | 2016131954 A1 | 8/2016 |
| WO | 2017032599 A1 | 3/2017 |
| WO | 2017050694 | 3/2017 |
| WO | 2017129314 | 8/2017 |
| WO | 2018085952 | 5/2018 |

* cited by examiner

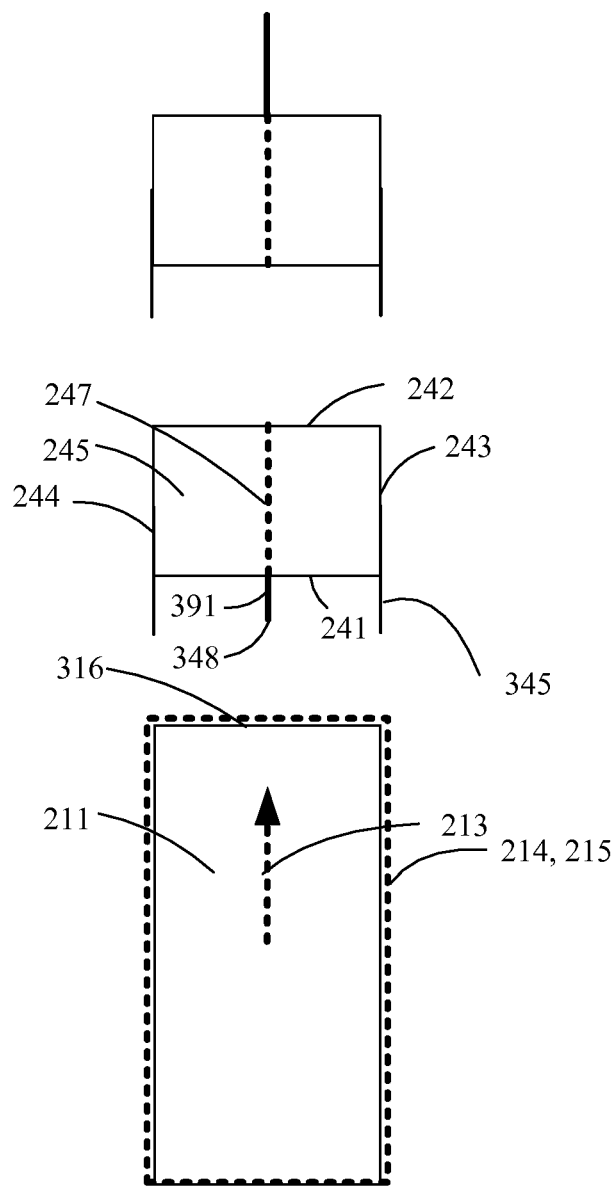
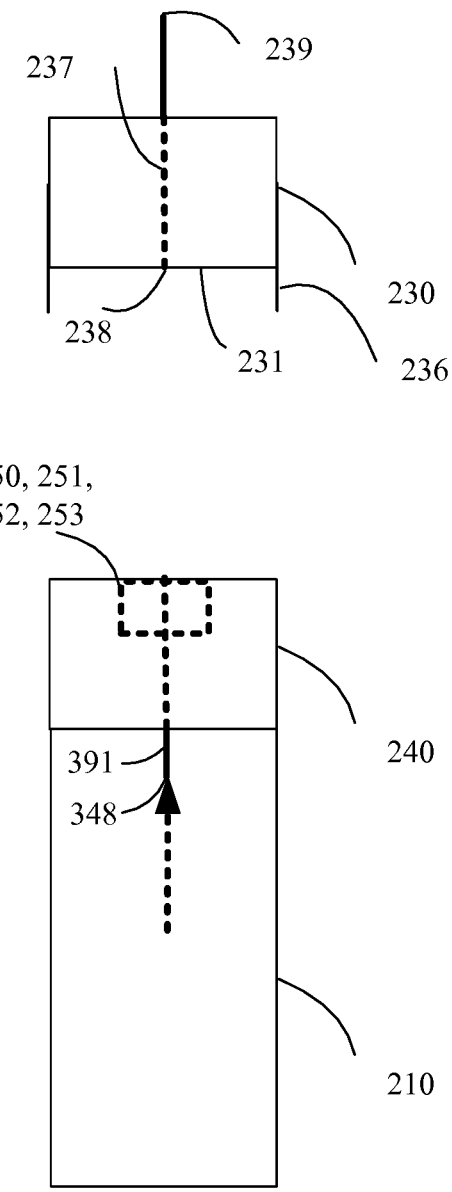
Fig. 3A
Fig. 3B

700

700

800

800

1200

1200

1200

FLOW COMMUNICATION UNIT WITH UNCONNECTED AND CONNECTED CONFIGURATION

CROSS-REFERENCE TO RELATED APPLICATIONS

This application is a 35 U.S.C. § 371 National Stage application of International Application PCT/EP2019/050555 (published as WO 2019/197061), filed Jan. 10, 2019, which claims priority to European Patent Application 18167233.8, filed Apr. 13, 2018, the contents of all above-named applications are incorporated herein by reference.

TECHNICAL FIELD

The present invention relates to a flow communication unit for establishing flow communication from a multi-use drug delivery device adapted for extended use, to a flow conducting device, wherein the drug delivery device comprises a pressurizeable reservoir comprising multiple doses of a drug formulation, and wherein the drug formulation allows microbial growth upon introduction of microorganisms into the reservoir during extended use, and wherein the flow conducting device is adapted for conducting the drug to the subcutaneous tissue of a subject comprising. In a further aspect the present invention relates to a flow communication unit for closing containers comprising multiple doses, and for permitting the withdrawal of the contents without removal or destruction of the flow communication unit. In a further aspect the present invention relates to a flow communication unit for comprising an unconnected and a connected configuration.

BACKGROUND OF THE INVENTION

In the disclosure of the present invention reference is mostly made to the treatment of diabetes by delivery of liquid insulin formulation, however, this is only an exemplary use of the present invention.

Drug delivery devices in the form of drug injection devices have greatly improved the lives of patients who must self-administer liquid drugs and biological agents. Drug injection devices may take many forms, including simple disposable devices that are little more than an ampoule with an injection means or they may be highly sophisticated electronically controlled instruments with numerous functions. Some devices are intended for single-use and may come with an integrated needle, e.g. comprising a so-called pre-filled syringe. However, in case the drug delivery device is intended to be used for multiple injections, it will typically be designed for use with a replaceable needle or cannula unit which ideally is to be replaced for each injection of a dose of drug. Regardless of their form, they have proven to be great aids in assisting patients to self-administer injectable drugs and biological agents. They also greatly assist care givers in administering injectable medicines to those incapable of performing self-injections.

In particular pen-style injection devices have proven to provide an accurate, convenient, and often discrete, way to administer drugs and biological agents, such as insulin. While pen-style injection devices are typically cylindrically shaped with a mounted needle protruding from the most distal portion of one end of the device, some devices have other shapes with the needle no longer protruding from the most distal part of an end of the device, e.g. Innovo® and InnoLet® from Novo Nordisk A/S, Bagsvaerd, Denmark.

Typically, injection devices use a pre-filled cartridge containing the liquid medication of interest, e.g. 1.5 or 3.0 ml of insulin or growth hormone formulation. The cartridge is typically in the form of a generally cylindrical transparent glass cylinder having a distal bottle neck portion with a distal opening closed by a needle pierceable septum and an opposed proximal opening in which an elastomeric piston is received, the piston being arranged to be moved by the dosing mechanism of the injection device. The injection devices generally are of two types: "Durable" devices and "disposable" devices. A durable device is designed to allow a user to replace one cartridge with another cartridge, typically a new cartridge in place of an empty cartridge. In contrast, a disposable device is provided with an integrated cartridge which cannot be replaced by the user; when the cartridge is empty the entire device is discarded.

As described above, a drug delivery device intended to be used for multiple injections is typically designed to be used in combination with a replaceable needle unit comprising a proximal needle portion adapted to be inserted into the drug-filled cartridge through a needle-penetrable septum seal and a distal needle portion adapted to be introduced subcutaneously, this allowing a given dose amount of liquid drug formulation to be injected subcutaneously through the hollow needle. Since the proximal needle portion penetrates the seal of the cartridge and provides a flow path from the inside of the cartridge to the outside, a risk of contamination of the cartridge contents is introduced.

Drug delivery devices can also be in the form of infusion systems comprising a pump with the above mentioned cartridge, and an infusion set conducting liquid drug from the reservoir of the cartridge to an infusion site on a subject.

The risk of contamination is primarily related to removal of the needle unit or the infusion set after use. As long as the cannula is penetrating the cartridge seal, it provides access from surroundings to the drug formulation and should thus be removed immediately after injection. However, after injection but prior to removal of the needle, the small volume of drug formulation inside the needle itself may be contaminated either from body fluids or from bacteria in the surroundings when the cannula is extracted from the skin of the subject. When the cannula is removed from the cartridge, some of the remaining fluid in the cannula may be sucked into the cartridge, thereby contaminating the drug formulation in the cartridge.

Therefore, drug formulations for use in multi dose injection devices must contain a sufficient level of preservatives to insure biostatic conditions during the expected in-use time of the cartridge to counter such contamination, i.e., to ensure conditions wherein growth of microorganisms are inhibited. This requirement is included in chapters on injectable drug formulations in current versions of international pharmacopeia.

The different national and international pharmacopoeias are issued by officially recognized authorities and provide common quality standards throughout the pharmaceutical industry. The standards for product quality tests of parenteral drug products, which include injections, is a part of the pharmacopoeia and some of the requirements are described in the following. Parenteral drug products are injected through the skin or other external boundary tissue, to allow the direct administration of the active drug substance(s) into blood vessels, organs, tissues, or lesions. Injections may exist as either immediate- or extended-release dosage forms. Routes of administration for parenteral drug products include intravenous, intraventricular, intra-arterial, intra-articular, intramuscular, intrathecal, intracisternal, intraocular and subcutaneous. Parenteral dosage forms include solutions, suspensions, emulsions, sterile powders for solutions and suspensions (including liposomes), and products that consist of both a drug and a device such as drug-eluting stents.

A regulatory requirement to drug delivery devices is that the packaging system should not interact physically or chemically with the preparation to alter its strength, quality, or purity beyond the official or established requirements. The packaging system should be closed or sealed in such a manner as to prevent contamination or loss of contents. Validation of container integrity must demonstrate no penetration of microbial contamination or gain or loss of any chemical or physical parameter deemed necessary to protect the product.

The above mentioned drug delivery devices are more than just a packaging system, as they have additional functions to ease administration. Such drug delivery devices may be referred to as dual function container-closure systems.

According to the pharmacopoeias, dual function container-closure systems are characterized by the addition of one or more intended functions to that of a container and require special consideration for integrity evaluation. Frequently, one compartment of the dual container-closure system, a container compartment, is designed to contain the drug or solution prior to use or activation. Another compartment, a delivery compartment, different in function and design, either directly delivers the product from the system-product containment compartment to a fluid pathway for direct injection of the patient or communicates with a sterile pathway of another access device. For example, a prefilled syringe contains a solution (the container compartment) and a device component (the delivery compartment) physically separated from the container compartment and used to directly administer the drug to the patient.

Therefore, dual container-closure systems typically have at least two compartments that require microbial barrier properties, and packaging integrity after sterilization and/or aseptic filling should be demonstrated for both compartments. In many cases, different portions of the dual system require different integrity testing methods. The selection of the integrity testing method is determined primarily on the basis of the intended objectives or performance requirements of the particular compartment. For example, the solution or drug-containing container compartment of the dual container-closure system must be enclosed or sealed in a manner that precludes leakage of product or microbial ingress during and following the manufacturing process. On the other hand, the delivery portion (the portion comprising the delivery compartment) of the dual container-closure system frequently contains a fluid pathway that is empty during the sterilization or aseptic filling process and is intended to remain dry until the product container portion is activated prior to use. A covering, a sheath, or perhaps a cap designed to vent during sterilization and storage protects the delivery compartment from airborne microbial ingress throughout the life of the article. However, this portion of the device is frequently not designed to prevent liquid ingress. Liquid ingress can be precluded by secondary packaging or by the physical design of the system itself.

Closures for multiple-dose containers permit the withdrawal of the contents without removal or destruction of the closure. The closure permits penetration by a needle and, upon withdrawal of the needle, closes at once, protecting the container against contamination. Validation of the multiple-dose container integrity must include verification that such a package prevents microbial contamination or loss of product contents under anticipated conditions of multiple entry and use.

For example, for testing prefilled syringes without attached sterile needles, the test includes expelling and transferring the content to a culture medium. At intervals during the incubation period and at its conclusion, examine the media for macroscopic evidence of microbial growth. If no evidence of microbial growth is found, the product to be examined complies with the test for sterility In multiple-dose containers the liquid drug is preserved with preservatives in order to prevent microbial growth during the extended use, i.e., small doses over an extended in-use time as in continuous delivery or larger doses over an extended in-use time. The use of preservatives may in some cases reduce the efficacy of the drug and in some cases be incompatible with the drug, which means that such type of drug formulations cannot be used with a multi-dose injection device. For example, the necessary preservatives would destroy the drug substance in the cartridge by precipitating the drug substance or chemically react with it.

WO 2015/1770821 discloses a medical cartridge for multiple doses of a medical drug, which allows the waste of medical drug to be minimised, without requiring the use of preservatives in the medical drug. The medical cartridge is provided with a one way valve, arranged in an interior part 5 of the medical cartridge at a position near an outlet end. The one way valve is arranged to allow a fluid flow from the interior of the medical cartridge towards the outlet end, and to prevent a fluid flow from the outlet end towards the interior of the medical cartridge. An injection needle can be mounted via a needle adapter at the outlet end of the cartridge, and extends through a septum, at the outlet end of the cartridge. It is an advantage that the one way valve is arranged in an interior part of the cartridge, because thereby the one way valve can be designed in a manner which reduces a dead volume inside the cartridge. By arranging the one way valve in the interior part of the cartridge, no additional or exterior interface between the outlet end of the cartridge and the one way valve is required, and thereby the risk of leaks at such an interface is eliminated, or at least considerably reduced. The description of a different embodiment indicates that the one way valve may replace a passive septum of the medical cartridge. According to such an embodiment, the one way valve is arranged inside the cartridge, immediately adjacent to the outlet end, and in immediate contact with an injection needle connected to the outlet end of the cartridge. This design may even further reduce the dead volume inside the cartridge, thereby even further reducing the waste of medical drug.

For such systems it is important that there is no leakage during use, and it is furthermore important that impurities are restricted in entering the drug delivery device for example across the immediate contact interface between the valve and the injection needle.

DISCLOSURE OF THE INVENTION

In the disclosure of the present invention, embodiments and aspects will be described which will address one or more of the above objects or which will address objects apparent from the below disclosure as well as from the description of exemplary embodiments. Thus, in a general aspect of the invention a flow communication unit for establishing flow communication from a multi-use drug delivery device adapted for extended use, to a flow conducting device, wherein the drug delivery device comprises a reservoir comprising multiple doses of a liquid drug formulation, wherein the reservoir is adapted to pressurize the liquid drug formulation, wherein the flow conducting device is adapted for conducting the drug to the subcutaneous tissue of a subject, wherein the flow communication unit comprises:

an inlet surface for interfacing a drug delivery device,
an outlet surface configured for being in: (i) a connected configuration, wherein the outlet surface allows the flow communication unit and the flow conducting device to be connected, and wherein the outlet surface is adapted for interfacing the flow conducting device, (ii) an unconnected configuration, wherein the outlet surface allows the flow communication unit and the flow conducting device to be unconnected, and wherein the outlet surface is adapted for reducing the entrance of contaminations into the interior space of the flow communication unit;
intermediate surfaces extending between the inlet surface and the outlet surface, wherein the inlet surface, the outlet surface and the intermediate surfaces define an outer surface and confines an interior space of the flow communication unit, for the outlet surface being in any of the connected and the unconnected configurations,
an outlet sealing member providing a portion of the outlet surface, for the outlet surface being in the connected configuration, wherein the outlet sealing member is adapted for contacting the flow conducting device to establish a fluid tight channel seal,
a first flow channel comprising a channel inlet adapted for providing flow communication with the drug delivery device, and a channel outlet adapted for providing flow communication with the flow conducting device,
a first outlet valve member
an outlet barrier comprising a second outlet valve member adapted to cooperate with the first outlet valve member, wherein the outlet barrier provides a portion of the outlet surface, and wherein the outlet barrier is configured for being in:
(i) a closed configuration, wherein the outlet surface is in the unconnected configuration, wherein the second outlet valve member is adapted to cooperate with the first outlet valve member to provide an outlet barrier seal, and wherein the outlet barrier seal is adapted to reduce the entrance of contaminations through the channel outlet and into the first channel, and
(ii) a flow configuration, wherein the outlet surface is in the connected configuration, wherein the second outlet valve member is adapted to cooperate with the first outlet valve member to allow a drug contained in the first channel to flow downstream from the channel inlet and out of the channel outlet, in response to the pressure in the first channel being above a first threshold;

wherein the flow communication unit is further adapted for being in:
(i) an unconnected configuration, in response to disconnecting the flow communication unit from the flow conducting device, wherein the outlet surface is in the unconnected configuration, and wherein the outlet barrier is in the closed configuration, and
(ii) a connected configuration, in response to connecting the flow communication unit to the flow conducting device, wherein the outlet surface is in the connected configuration, wherein the outlet barrier is in the flow configuration, wherein the outlet sealing member is arranged to be able to contact the flow conducting device to provide the channel seal downstream to the channel outlet of the first flow channel, and thereby adapted to allow flow communication between the channel outlet and the flow conducting device, wherein the channel outlet is arranged at the outlet surface of the flow communication unit; and wherein a combined flow channel can be provided between the drug delivery device, the first flow channel and the flow conducting device with the channel seal arranged downstream to the channel outlet, in response to the channel inlet being arranged in flow communication with the drug delivery device and the flow communication unit being connected to the flow conducting device;

whereby the flow communication unit is adapted to enable the extended use of the multi-use drug delivery device, and whereby the flow communication unit is adapted to inhibit microbial entrance in the multi-use drug delivery device during the extended use.

Hereby is provided a flow communication unit allowing extended use of a drug formulation which does not contain preservatives to a degree where it inhibits microbial growth, i.e., the drug formulation allows microbial growth upon introduction of microorganisms into the reservoir during extended use. A multiple-dose drug delivery device combined with the flow communication unit according to the present disclosure will enable extended use without destruction or removal of a closure of the multiple-dose drug delivery device.

In a further aspect, the outlet barrier provides the channel outlet, whereby the barrier can regulate the flow out of the drug delivery device and restrict the entrance of contamination into the first flow channel, in the connected and the unconnected configuration of the first channel.

In a further aspect, the flow communication unit further comprises a unidirectional valve arranged along the first channel and adapted for guiding the flow downstream and inhibiting upstream flow towards the drug delivery device. A forced unidirectional flow contributes to the reduction of contaminations through the channel outlet and into the first channel, and making the unidirectional valve a part of the flow communication unit enables the provision of a self-contained flow communication unit, wherein unidirectional flow is ensured. The valve can e.g. be a part of the outlet barrier but it can be arranged at all positions along the first flow channel.

In a further aspect, the flow communication unit further comprises a proximal piercing needle extending from the inlet surface in an extended configuration, wherein the proximal needle comprises a proximal open end providing the channel inlet. In this way the flow communication unit is adapted for piercing a septum, and thereby establish fluid communication with a multiple-dose drug reservoir.

In a further aspect, the flow communication unit further comprises a proximal piercing needle actuator adapted to change the proximal piercing needle from a retracted configuration to the extended configuration, in response to connecting the flow communicating unit with the flow conducting device. In this way, the risk of needle injuries can be reduced, and a protecting skirt portion of the flow communication unit can be avoided.

In a further aspect the flow communication unit further comprises a proximal valve member, adapted to allow a flow from the inlet towards the outlet and for preventing a reverse flow.

In a further aspect, the proximal valve member provides a portion of the inlet surface for interfacing the drug delivery device.

In a further aspect, the proximal valve member provides a portion of the intermediate surfaces extending between the inlet surface and the outlet surface.

In a further aspect, the portion of the intermediate surfaces is soft and provides a device sealing surface to seal against the drug delivery device.

In a further aspect, the proximal valve member provides the channel inlet 548, 648, 748, 848.

In a further aspect, a distal support member comprises a distal end and a distal portion adapted to support the outlet barrier, and wherein
- the distal support member further comprises a barrier operating member adapted to cooperate with the outlet barrier in regulating the tightness of the outlet barrier seal,
- wherein the outlet barrier comprises an actuator portion providing the outlet sealing member and movably arranged between a first position and a second position relative to the barrier operating member, and adapted to be configured in an:
  (i) unconnected configuration, wherein the outlet barrier is in the closed configuration, wherein the closed configuration of the outlet barrier further comprises the actuator portion being in the first position relative to the barrier operating member, whereby the second outlet valve member is adapted to cooperate with the first outlet valve member to provide the outlet barrier seal adapted to allow a drug contained in the first channel to flow downstream from the channel inlet and out of the channel outlet, in response to the pressure in the first channel being above a second threshold, wherein the second threshold defines the tightness of the outlet barrier seal in the unconnected configuration and is larger than the first threshold,
  (ii) a connected configuration, wherein the outlet barrier is in the flow configuration, wherein the flow configuration of the outlet barrier further comprises the actuator portion is in the second position relative to the barrier operating member, whereby the second outlet valve member is adapted to cooperate with the first outlet valve member to provide the outlet barrier seal adapted allow a drug contained in the first channel to flow downstream from the channel inlet and out of the channel outlet, in response to the pressure in the first channel being above the first threshold, wherein the first threshold defines the tightness of the outlet barrier seal in the connected configuration.

In a further aspect, the actuator portion is adapted to be manipulated from the first position to the second position, by the flow conducting device upon connection.

In a further aspect, the flow communication unit is further adapted for being in:
  (i) the unconnected configuration, wherein the tightness of the barrier seal is defined by a second threshold, and
  (ii) the connected configuration, wherein the tightness of the barrier seal is defined by the first threshold.

In some embodiments and a further aspect, the flow communication unit further comprises a proximal support member comprising a proximal end and a proximal portion adapted to support the proximal valve member.

In a further aspect, the proximal support member is rigid, and wherein the proximal portion of the proximal support member comprises a surface portion defining a proximal valve seat adapted to provide a proximal seat sealing surface, wherein the proximal valve member comprises a surface portion adapted to provide a proximal valve sealing surface, and wherein a proximal fluid tight seal can be provided between the proximal valve sealing surface and the proximal seat sealing surface.

In a further aspect, the proximal support member is rigid and provides a proximal portion of the first channel.

In a further aspect, the proximal portion of the first channel provided by the proximal support member extends from the proximal end of the proximal support member.

In a further aspect, the proximal valve member comprises a surface portion providing a portion of the inlet surface for interfacing the drug delivery device, and wherein the proximal valve member is flexible and can be changed from a normal configuration to a forced configuration, in response to a fluid pressure on the inlet surface.

In a further aspect, the flow communication unit comprises a normally closed configuration, wherein the proximal valve member is in the normal configuration, and thereby provides the proximal fluid tight seal.

In a further aspect, the proximal support member comprises an enlarged channel portion adapted to accommodate an accommodative portion of the proximal valve member, wherein the accommodative portion of the proximal valve member comprises the proximal valve sealing surface, wherein the flow communication unit comprises an open configuration, wherein the enlarged channel portion accommodates the accommodative portion of the proximal valve member in the forced configuration, and wherein the proximal fluid tight seal is not provided.

In a further aspect, the proximal support member further comprises a support portion adapted to be supported by the drug delivery device, and thereby provide support for the flow communication unit in relation to the drug delivery device.

In some embodiments and in a further aspect, the flow communication unit comprises an intermediate valve member.

In a further aspect, the proximal support member comprises a distal end and a distal portion adapted to support the intermediate valve member.

In a further aspect, the proximal support member is rigid, and wherein the distal portion of the proximal support member comprises a surface portion defining an intermediate valve seat adapted to provide an intermediate seat sealing surface, wherein the intermediate valve member comprises a surface portion adapted to provide an intermediate valve sealing surface, and wherein an intermediate fluid tight seal (597.8) can be provided between the intermediate valve sealing surface and the intermediate seat sealing surface.

In a further aspect, the proximal portion of the first channel provided by the proximal support member extends from the proximal end to the distal end.

In a further aspect, the intermediate valve member comprises a proximal surface portion for interfacing the proximal support member, and wherein the intermediate valve member is flexible and can be changed from a normal configuration to a forced configuration, in response to a fluid pressure on the proximal surface.

In a further aspect, the normally closed configuration of the flow communication unit further comprises, the intermediate valve member being in the normal configuration and provides the intermediate fluid tight seal.

In some embodiments and in a further aspect, the flow communication unit comprises a distal support member.

In a further aspect the distal support member is rigid and provides a distal portion of the first channel.

In a further aspect, the distal support member comprises an enlarged channel portion adapted to receive a portion of a flexible portion of the intermediate valve member, wherein the flexible portion of the intermediate valve member comprises the intermediate valve sealing surface, wherein the open configuration of the flow communication unit further comprises the enlarged channel portion receiving the portion of the flexible portion of the intermediate valve member in the forced configuration, wherein the intermediate fluid tight seal is not provided.

In a further aspect, the distal support member further comprises a support portion adapted to be supported by the proximal support member, and thereby provide stability to the flow communication unit.

In a further aspect, the distal support member and the proximal support member are adapted to clamp a portion of the intermediate valve member, and whereby the clamped portion is fixed and the unclamped portion adapted to be moved between the normal and the forced configuration.

In a further aspect, the distal support member further comprises a support portion adapted to be supported by the drug delivery device, and thereby provide support for the flow communication unit in relation to the drug delivery device.

In some embodiments and in a further aspect the distal support member comprises a distal end and a distal portion adapted to support the outlet barrier.

In a further aspect, the distal support member is rigid, and wherein the distal portion of the distal support member comprises a surface portion defining the first outlet valve member adapted to provide a seat sealing surface, wherein the outlet barrier comprises a surface portion defining the second outlet valve member adapted to provide a valve sealing surface, and wherein the outlet barrier seal can be provided between the valve sealing surface and the seat sealing surface.

In a further aspect the outlet barrier comprises a proximal surface portion for interfacing the distal support member, and wherein the outlet barrier is flexible and can be changed from a normal configuration to a forced configuration, in response to the pressure in the first channel and on the proximal surface portion being above the first threshold.

In a further aspect the normally closed configuration of the flow communication unit further comprises, the outlet barrier being in the normal configuration and provides the outlet barrier seal.

In a further aspect, the flow conducting device comprises an enlarged channel inlet adapted to receive a portion of a flexible portion of the outlet barrier, wherein the flexible portion of the outlet barrier comprises the valve sealing surface, wherein the open configuration of the flow communication unit further comprises the enlarged channel inlet receiving the portion of the flexible portion of the outlet barrier in the forced configuration, wherein the outlet barrier seal is not provided.

In a further aspect the outlet barrier provides the outlet sealing member, whereby the number of components can be reduced.

In some embodiments and in a further aspect, the distal support member comprises a distal end and a distal portion adapted to support the outlet barrier, and wherein the distal support member further comprises a spacing member adapted to separate the supported outlet barrier from the distal support member, whereby a space is provided between the distal support member and the outlet barrier, wherein the outlet barrier comprises an actuator portion providing the outlet sealing member and movably arranged between a first position and a second position relative to the spacing member, and adapted to be configured in an:

(i) unconnected configuration, wherein the outlet barrier is in the closed configuration, wherein the closed configuration of the outlet barrier further comprises the actuator portion being in the first position relative to the spacing member, whereby the second outlet valve member is adapted to cooperate with the first outlet valve member to provide the outlet barrier seal adapted to allow a drug contained in the first channel to flow downstream from the channel inlet and out of the channel outlet, in response to the pressure in the first channel being above a second threshold, wherein the second threshold defines the tightness of the outlet barrier seal and is larger than the first threshold, (ii) a connected configuration, wherein the outlet barrier is in the flow configuration, wherein the flow configuration of the outlet barrier further comprises the actuator portion is in the second position relative to the spacing member, whereby the second outlet valve member is adapted to cooperate with the first outlet valve member to provide the outlet barrier seal adapted allow a drug contained in the first channel to flow downstream from the channel inlet and out of the channel outlet, in response to the pressure in the first channel being above the first threshold, wherein the first threshold defines the tightness of the outlet barrier seal.

In a further aspect, the actuator portion, is adapted to be manipulated from the first position to the second position, by the flow conducting device upon connection.

In a further aspect, the flow communication unit is further adapted for being in:

(i) the unconnected configuration, wherein the tightness of the barrier seal is defined by a second threshold, and (ii) the connected configuration, wherein the tightness of the barrier seal is defined by the first threshold.

In a further aspect, the flow conducting device comprises sealing members adapted to cooperate with the outlet sealing members of the flow conducting device.

In some embodiments and in a further aspect, the flow communication unit further comprises a support member comprising a proximal end and a proximal portion adapted to support the proximal valve member.

In a further aspect, the support member is rigid, wherein the proximal valve member is a self-contained valve comprising a first valve member comprising a surface portion adapted to provide a first proximal valve sealing surface, and a second valve member comprising a surface portion adapted to provide a second proximal valve sealing surface, wherein a proximal fluid tight seal can be provided between the first and the second proximal valve sealing surface.

In a further aspect, the support member is rigid, and wherein the proximal portion of the support member comprises a proximal valve housing adapted to accommodate an accommodative portion of the self-contained valve.

In a further aspect, the support member provides a portion of the first channel.

In a further aspect, the portion of the first channel, extends from the proximal end of the support member.

In a further aspect, the self-contained valve comprises a surface portion providing a portion of the inlet surface for interfacing the drug delivery device, and wherein the self-contained valve is flexible and can be changed from a normal configuration to a forced configuration, in response to a fluid pressure on the inlet surface.

In a further aspect, the flow communication unit comprises a normally closed configuration, wherein the self-contained valve is in the normal configuration, and thereby provides the proximal fluid tight seal.

In a further aspect, the flow communication unit comprises an open configuration, wherein the self-contained valve is in the forced configuration, and wherein the proximal fluid tight seal is not provided.

In a further aspect, the proximal valve housing comprises an enlarged channel portion adapted to accommodate the accommodative portion, wherein the accommodative portion of the self-contained valve comprises the first and the second proximal valve sealing surface, wherein the accommodative portion radially expands as the self-contained valve changes from the normal to the forced configuration, and wherein the proximal valve housing is adapted to provide a stop for the radial expansion, and thereby define the maximum expansion.

In a further aspect, the support member further comprises a support portion adapted to be supported by the drug delivery device, and thereby provide support for the flow communication unit in relation to the drug delivery device.

In some embodiments and in a further aspect, the support member comprises a distal end and a distal portion adapted to support the outlet barrier.

In a further aspect, the distal portion comprises a surface portion defining the first outlet valve member adapted to provide a seat sealing surface, wherein the outlet barrier comprises a surface portion defining the second outlet valve member adapted to provide a valve sealing surface, and wherein the outlet barrier seal can be provided between the valve sealing surface and the seat sealing surface.

In a further aspect, the outlet barrier comprises a proximal surface portion for interfacing the distal portion, and wherein the outlet barrier is flexible and can be changed from a normal configuration to a forced configuration, in response to a fluid pressure on the proximal surface.

In a further aspect, the normally closed configuration of the flow communication unit further comprises, the outlet barrier being in the normal configuration and provides the outlet barrier seal.

In a further aspect, the flow conducting device comprises an enlarged channel inlet adapted to accommodate a portion of a flexible portion of the outlet barrier, wherein the flexible portion of the outlet barrier comprises the valve sealing surface, wherein the open configuration of the flow communication unit further comprises the enlarged channel inlet accommodating the portion of the flexible portion of the outlet barrier in the forced configuration, wherein the outlet barrier seal is not provided.

In some embodiments and in a further aspect, the flow communication unit further comprises a proximal support member comprising a proximal end and a proximal portion adapted to support the proximal valve member.

In a further aspect, the proximal valve member is a self-contained valve comprising a first valve member comprising a surface portion adapted to provide a first proximal valve sealing surface, and a second valve member comprising a surface portion adapted to provide a second proximal valve sealing surface, wherein a proximal fluid tight seal can be provided between the first and the second proximal valve sealing surface.

In a further aspect, the proximal support member is rigid, and wherein the proximal valve member comprises a skirt portion adapted to surround and fixedly engage the proximal portion of the proximal support member.

In a further aspect, the self-contained valve comprises a surface portion providing a portion of the inlet surface for interfacing the drug delivery device, and wherein the self-contained valve is flexible and can be changed from a normal configuration to a forced configuration, in response to a fluid pressure on the inlet surface.

In a further aspect, the flow communication unit comprises a normally closed configuration, wherein the self-contained valve is in the normal configuration, and thereby provides the proximal fluid tight seal.

In a further aspect, the flow communication unit comprises an open configuration, wherein the self-contained valve is in the forced configuration, and wherein the proximal fluid tight seal is not provided.

In a further aspect, the proximal portion of the proximal support member comprises an enlarged channel portion adapted to receive a portion of a flexible portion of the self-contained valve, wherein the flexible portion comprises a portion of the first and the second proximal valve sealing surface, wherein the flexible portion axially deflects into the enlarged channel portion, in response to the self-contained valve changes from the normal to the forced configuration, and wherein the proximal portion is adapted to provide a stop for the axial deflection, and thereby define the maximum deflection.

In a further aspect, the proximal support member further comprises a support portion adapted to be supported by the drug delivery device, and thereby provide support for the flow communication unit in relation to the drug delivery device.

In some embodiments and in a further aspect, the proximal support member comprises a distal end and a distal portion adapted to support the outlet barrier.

In a further aspect, the proximal support member is rigid, and wherein the distal portion of the proximal support member comprises a surface portion defining the first outlet valve member adapted to provide a seat sealing surface, wherein outlet barrier comprises a surface portion defining the second outlet valve member adapted to provide a valve sealing surface, and wherein the outlet barrier seal can be provided between the valve sealing surface and the seat sealing surface.

In a further aspect, the outlet barrier comprises an inner surface portion for interfacing the distal portion of proximal support member, and wherein the outlet barrier is flexible and can be changed from a normal configuration to a forced configuration, in response to a fluid pressure on the inner surface portion.

In a further aspect, the normally closed configuration of the flow communication unit further comprises, the outlet barrier being in the normal configuration and provides the outlet barrier seal.

In a further aspect, the proximal support member provides a proximal portion of the first channel.

In a further aspect, the proximal portion of the first channel extends from the proximal end to an intermediate position.

In a further aspect, a distal portion of the first channel is provided between the distal portion and the outlet barrier, and wherein the distal portion of the first channel extends from the intermediate position to the outlet.

In some embodiments and in a further aspect, the outlet barrier provides an intermediate valve member.

In a further aspect, the distal portion of the proximal support member is adapted to support the intermediate valve member.

In a further aspect, the distal portion of the proximal support member comprises a surface portion defining an intermediate valve seat adapted to provide an intermediate seat sealing surface, wherein the intermediate valve member comprises a surface portion adapted to provide an intermediate valve sealing surface, and wherein an intermediate fluid tight seal can be provided between the intermediate valve sealing surface and the intermediate seat sealing surface.

In a further aspect, the intermediate valve member comprises an inner surface portion for interfacing the proximal support member, and wherein the intermediate valve member is flexible and can be changed from a normal configuration to a forced configuration, in response to a fluid pressure on the inner surface portion.

In a further aspect, the normally closed configuration of the flow communication unit further comprises, the intermediate valve member being in the normal configuration and provides the intermediate fluid tight seal.

In a further aspect, the intermediate valve member is positioned in the distal portion of the first channel.

In some embodiments and in a further aspect, the flow communication unit further comprises a distal support member.

In a further aspect, the distal support member comprises a tubular portion adapted to accommodate an accommodative portion of the outlet barrier, wherein the accommodative portion radially expands as the outlet barrier changes from the normal to the forced configuration, and wherein the tubular portion is adapted to provide a stop for the radial expansion, and thereby define the maximum expansion.

In a further aspect, the accommodative portion of the outlet barrier comprises the second outlet valve member, wherein the open configuration of the flow communication unit further comprises the outlet barrier being in the forced configuration, and wherein the outlet barrier seal is not provided.

In a further aspect, the accommodative portion of the outlet barrier comprises the intermediate valve member, wherein the open configuration of the flow communication unit further comprises the outlet barrier being in the forced configuration, and wherein the intermediate fluid tight seal is not provided.

In a further aspect, wherein the distal support member further comprises a support portion adapted to be supported by the proximal support member, and thereby provide stability to the flow communication unit.

In some embodiments and in a further aspect, the flow communication unit further comprises a distal sealing member providing the outlet sealing member.

In some embodiments and in a further aspect, the distal support member is adapted to support the distal sealing member.

In some embodiments and in a further aspect, the proximal valve member further comprises a support portion adapted to be supported by the drug delivery device (210), and thereby provide support for the flow communication unit in relation to the drug delivery device (210).

In a further aspect, the proximal valve member is adapted to fit into an adapter top having a retaining member on an inner surface, wherein the proximal valve member comprises a planar distal surface, and a recess adapted to receive the retaining member when the proximal valve member is inserted into the adaptor top, and whereby the distal surface remains planar to allow close contact with another planar surface.

In some embodiments and in a further aspect, the flow communication unit further comprises a proximal support member comprising a proximal end and a proximal portion adapted to support the proximal valve member.

In a further aspect, the proximal support member is rigid, wherein the proximal valve member is a self-contained valve comprising a first valve member comprising a surface portion adapted to provide a first proximal valve sealing surface, and a second valve member comprising a surface portion adapted to provide a second proximal valve sealing surface, wherein a proximal fluid tight seal can be provided between the first and the second proximal valve sealing surface.

In a further aspect, the proximal support member is rigid with a planar proximal surface, and wherein the self-contained valve comprises a substantially planar distal surface, and wherein the proximal support member is adapted to transfer a compression force to the self-contained valve, and wherein the self-contained valve is adapted to transfer a compression force to the drug delivery device.

In a further aspect, the proximal support member is rigid, and wherein the proximal support member is adapted to fit into an adaptor top having a retaining member on an inner surface, and wherein the proximal support member comprises a planar proximal surface adapted to be supported by the retaining member, and whereby the proximal surface can be retained in close contact with a distal planar surface of the self-contained valve (898), when the proximal support member and the self-contained valve are inserted into the adaptor top.

In a further aspect, the proximal support member is rigid and provides a proximal portion of the first channel.

In a further aspect, the proximal portion of the first channel provided by the proximal support member extends from the proximal end of the proximal support member.

In a further aspect, the self-contained valve comprises a surface portion providing a portion of the inlet surface for interfacing the drug delivery device, and wherein the self-contained valve is flexible and can be changed from a normal configuration to a forced configuration, in response to a fluid pressure on the inlet surface.

In a further aspect, the flow communication unit comprises a normally closed configuration, wherein the self-contained valve is in the normal configuration, and thereby provides the proximal fluid tight seal.

In a further aspect, the flow communication unit comprises an open configuration, wherein the self-contained valve is in the forced configuration, and wherein the proximal fluid tight seal is not provided.

In a further aspect, the proximal portion of the proximal support member comprises an enlarged channel portion adapted to receive a portion of a flexible portion of the self-contained valve, wherein the flexible portion comprises a portion of the first and the second proximal valve sealing surface, wherein the portion of the flexible portion axially deflects into the enlarged channel portion, in response to the self-contained valve changes from the normal to the forced configuration, and wherein the proximal portion is adapted to provide a stop for the axial deflection, and thereby define the maximum deflection.

In some embodiments and in a further aspect, the flow communication unit further comprises an intermediate valve member.

In a further aspect, the proximal support member comprises a distal end and a distal portion adapted to support the intermediate valve member.

In a further aspect, the proximal support member is rigid, and wherein the distal portion of the proximal support member comprises a surface portion defining an intermediate valve seat adapted to provide an intermediate seat sealing surface, wherein the intermediate valve member comprises a surface portion adapted to provide an intermediate valve sealing surface, and wherein an intermediate fluid tight seal can be provided between the intermediate valve sealing surface and the intermediate seat sealing surface.

In a further aspect, the proximal portion of the first channel extends from the proximal end to the distal end.

In a further aspect, the intermediate valve member comprises a proximal surface portion for interfacing the distal portion of the proximal support member, and wherein the intermediate valve member is flexible and can be changed from a normal configuration to a forced configuration, in response to a fluid pressure on the proximal surface.

In a further aspect, the normally closed configuration of the flow communication unit further comprises, the intermediate valve member being in the normal configuration and provides the intermediate fluid tight seal.

In some embodiments and in a further aspect, the flow communication unit further comprises a distal support member.

In a further aspect, the distal support member is rigid and provides a distal portion of the first channel.

In a further aspect, the distal support member comprises an enlarged channel portion adapted to receive a portion of a flexible portion of the intermediate valve member, wherein the flexible portion of the intermediate valve member comprises the intermediate valve sealing surface, wherein the open configuration of the flow communication unit further comprises the enlarged channel portion receiving the portion of the flexible portion of the intermediate valve member in the forced configuration, wherein the intermediate fluid tight seal is not provided.

In a further aspect, the proximal support member, the intermediate valve member the distal support member provides a unit, wherein a portion of the intermediate valve member is clamped between the support members, and wherein the support members are welded together by ultrasound.

In a further aspect, the clamped portion is fixed and the unclamped portion is flexible and adapted to be moved between the normal and the forced configuration.

In some embodiments and in a further aspect, the distal support member comprises a distal end and a distal portion adapted to support the outlet barrier.

In a further aspect, the distal support member is rigid, wherein the outlet barrier is a self-contained valve comprising a first valve member comprising a surface portion adapted to provide a first proximal valve sealing surface, and a second valve member comprising a surface portion adapted to provide a second proximal valve sealing surface, wherein a proximal fluid tight seal can be provided between the first and the second proximal valve sealing surface.

In a further aspect, the self-contained valve comprises a proximal surface portion for covering the first channel, and wherein the self-contained valve is flexible and can be changed from a normal configuration to a forced configuration, in response to a fluid pressure in the first channel, and thereby on the proximal surface portion of the self-contained valve.

In a further aspect, the normally closed configuration of the flow communication unit comprises the self-contained valve is in the normal configuration, and thereby provides the proximal fluid tight seal.

In a further aspect, the open configuration of the flow communication unit comprises the self-contained valve is in the forced configuration, and wherein the proximal fluid tight seal is not provided.

In a further aspect, the proximal portion of the proximal support member comprises an enlarged channel portion adapted to receive a portion of a flexible portion of the self-contained valve, wherein the flexible portion comprises a portion of the first and the second proximal valve sealing surface, wherein the portion of the flexible portion axially deflects into the enlarged channel portion, in response to the self-contained valve changes from the normal to the forced configuration, and wherein the proximal portion is adapted to provide a stop for the axial deflection, and thereby define the maximum deflection.

In a further aspect, the distal support member is rigid with a planar distal surface, and wherein the self-contained valve comprises a substantially planar proximal surface, and wherein the distal support member is adapted to transfer a compression force to the outlet barrier, and wherein the outlet barrier is adapted to transfer a compression force to an adaptor top.

In a further aspect, the proximal support member is rigid, and wherein the proximal support member, the intermediate valve member, the distal support member and the outlet barrier are adapted to fit into an adaptor top having a retaining member on an inner surface, and wherein the proximal support member comprises a planar proximal surface adapted to be supported by the retaining member, and whereby the proximal surface can be retained in close contact with a the distal planar surface of the proximal valve member, when all members are inserted into the adaptor top.

In a further aspect, the proximal support member, the intermediate valve member and the distal support member provides a unit, wherein a portion of the intermediate valve member is clamped between the support members, and wherein the unit is adapted to be fitted into an adaptor top having a unit retaining member adapted to retain the unit in a compressed state.

In a further aspect, the outlet barrier and the unit are adapted to be retained in a compressed state in the adaptor top, wherein the retaining member can transfer a compression force to the unit, and the unit can transfer the compression force to a retaining surface of the adaptor top.

In a further aspect, the outlet barrier and the unit are adapted to be retained in a compressed state in the adaptor top, wherein the proximal valve member is adapted to be fitted into the adaptor top in a compressed state, and wherein the adaptor top comprises a device retaining member on an inner surface, wherein the device retaining member is adapted to connect the adaptor top to the drug retaining device, wherein the proximal valve member is supported by the drug delivery device in a compressed state.

In a further aspect, the flow conducting device comprises an enlarged channel inlet adapted to receive a portion of a flexible portion of the self-contained valve, wherein the flexible portion of the self-contained valve comprises a portion of the outlet barrier seal, wherein the open configuration of the flow communication unit further comprises the enlarged channel inlet receiving the portion of the flexible portion of the outlet barrier in the forced configuration, wherein the outlet barrier seal is not provided.

In a further aspect, the outlet barrier provides the outlet sealing member.

In a further aspect, distal support member comprises a distal end and a distal portion adapted to support the outlet barrier, wherein the distal support member further comprises a spacing member adapted to separate the supported outlet barrier from the distal support member, whereby a space is provided between the distal support member and the outlet barrier, and wherein the outlet barrier comprises an actuator portion providing the outlet sealing member and movably arranged between a first position and a second position relative to the spacing member, and adapted to be configured in an:

(i) unconnected configuration, wherein the outlet barrier is in the closed configuration, wherein the closed configuration of the outlet barrier further comprises the actuator portion being in the first position relative to the spacing member, whereby the second outlet valve member is adapted to cooperate with the first outlet valve member 854 to provide the outlet barrier seal adapted to allow a drug contained in the first channel to flow downstream from the channel inlet and out of the channel outlet, in response to the pressure in the first channel being above a second threshold, wherein the second threshold defines the tightness of the outlet barrier seal and is larger than the first threshold, (ii) a connected configuration, wherein the outlet barrier is in the flow configuration, wherein the flow configuration of the outlet barrier further comprises the actuator portion is in the second position relative to the spacing member, whereby the second outlet valve member is adapted to cooperate with the first outlet valve member to provide the outlet barrier seal adapted allow a drug contained in the first channel to flow downstream from the channel inlet and out of the channel outlet, in response to the pressure in the first channel being above the first threshold, wherein the first threshold defines the tightness of the outlet barrier seal, whereby the actuator portion, is adapted to be manipulated from the first position to the second position, by the flow conducting device upon connection.

In a further aspect, the flow communication unit is further adapted for being in:

(i) the unconnected configuration, wherein the tightness of the barrier seal is defined by a second threshold, and (ii) the connected configuration, wherein the tightness of the barrier seal is defined by the first threshold.

In a further aspect the flow conducting device comprises sealing members adapted to cooperate with the outlet sealing members of provided on the outlet barrier.

In a further aspect the outlet barrier is stretched by the sealing members of the flow conducting device, wherein the first and the second outlet sealing members are pulled away from each other, and thereby decreases the strength of the fluid tight outlet seal.

In some embodiments and in a further aspect, the proximal valve member provides the channel inlet in a normal configuration, wherein the valve is closed.

In a further aspect, the proximal valve member provides a channel passage in a forced configuration, wherein the valve is open.

In a further aspect, the proximal valve member comprises a distal surface portion for interfacing a movable channel member, and wherein the proximal valve member is flexible and can be changed from a normal configuration to a forced configuration, in response to a pressure from the movable channel member on the distal surface portion.

In some embodiments and in a further aspect, the flow communication unit further comprises a proximal support member comprising a proximal end and a proximal portion adapted to support the proximal valve member.

In a further aspect, the proximal support member is rigid, and the proximal valve member is a self-contained valve comprising a first valve member comprising a surface portion adapted to provide a first proximal valve sealing surface, and a second valve member comprising a surface portion adapted to provide a second proximal valve sealing surface, wherein a proximal fluid tight seal can be provided between the first and the second proximal valve sealing surface.

In a further aspect, the proximal support member is rigid, and wherein the self-contained valve comprises a skirt portion adapted to surround and/or be surrounded by the proximal portion of the proximal support member, whereby the self-contained valve and the proximal support member are fixedly engaged to each other.

In a further aspect, the self-contained valve comprises a proximal surface portion providing a portion of the inlet surface for interfacing the drug delivery device, and a distal surface portion for interfacing a movable channel member, wherein the self-contained valve is flexible and (i) wherein the self-contained valve can be changed from a normal configuration to a forced configuration, in response to a pressure from the movable channel member on the distal surface portion, and (ii) wherein the movable channel member supports the self-contained valve in the normal configuration, in response to a fluid pressure on the inlet surface, and whereby the fluid tight seal remains tight.

In a further aspect, the flow communication unit comprises a normally closed configuration, wherein the self-contained valve is in the normal configuration, and thereby provides the proximal fluid tight seal.

In a further aspect, the flow communication unit comprises an open configuration, wherein the self-contained valve is in the forced configuration and the channel inlet is provided by the movable channel member, and wherein the proximal fluid tight seal is not provided.

In a further aspect, the proximal portion of the proximal support member is adapted to receive a portion of the self-contained valve defining a channel seat portion, wherein the channel seat portion is adapted to provide a seat for a proximal portion of the movable channel member in a distal position, and wherein the self-contained valve is in the forced configuration.

In a further aspect, the proximal portion of the proximal support member is adapted to receive a portion of the self-contained valve defining a channel seat portion, wherein the channel seat portion is adapted to provide a seat for a distal portion of the movable channel member in a proximal position, wherein the movable channel member extends across the self-contained valve, wherein the self-contained valve provides a seal around the movable channel member, and wherein the self-contained valve is in the forced configuration.

In a further aspect, the proximal support member further comprises a support portion adapted to be supported by the drug delivery device, and thereby provide support for the flow communication unit in relation to the drug delivery device.

In some embodiments and in a further aspect, the proximal support member comprises a distal end and a distal portion adapted to support the outlet barrier.

In some embodiments and in a further aspect the flow communication unit further comprises a distal support member.

In a further aspect the proximal support member comprises a tubular portion adapted to accommodate the distal support member, wherein the distal support member is movably arranged within the tubular portion, and wherein the distal support member is adapted to be moved between a distal position and a proximal position.

In a further aspect, the distal support member comprises a proximal end and a proximal portion comprising a movable channel member.

In a further aspect, the distal support member comprises a distal end and a distal portion adapted to support the outlet barrier.

In a further aspect, the distal support member is rigid, and wherein the distal portion of the distal support member comprises a surface portion defining the first outlet valve member adapted to provide a seat sealing surface, wherein outlet barrier comprises a surface portion defining the second outlet valve member adapted to provide a valve sealing surface, and wherein the outlet barrier seal can be provided between the valve sealing surface and the seat sealing surface.

In a further aspect, the outlet barrier comprises an inner surface portion for interfacing the distal portion of the distal support member, and wherein the outlet barrier is flexible and can be changed from a normal configuration to a forced configuration, in response to a fluid pressure on the inner surface portion.

In a further aspect, the normally closed configuration of the flow communication unit further comprises, the outlet barrier being in the normal configuration and provides the outlet barrier seal.

In a further aspect, the proximal portion of the distal support member provides a proximal portion of the first channel.

In a further aspect, the proximal portion of the first channel extends from the proximal end to an intermediate position.

In a further aspect, a distal portion of the first channel is arranged between the distal portion and the outlet barrier, and wherein the distal portion of the first channel extends from the intermediate position to the outlet.

In a further aspect, the flow communication unit further comprises a biasing member adapted to bias the distal support member towards the distal position.

In a further aspect, the biasing member is positioned between a distal surface of the proximal support member and a proximal surface of the distal support member (993).

In a further aspect, the biasing member is a compression spring.

In some embodiments and in a further aspect, the outlet barrier provides an intermediate valve member.

In a further aspect, the distal portion of the distal support member is adapted to support the intermediate valve member.

In a further aspect, the distal portion of the distal support member comprises a surface portion defining an intermediate valve seat adapted to provide an intermediate seat sealing surface, wherein the intermediate valve member comprises a surface portion adapted to provide an intermediate valve sealing surface, and wherein an intermediate fluid tight seal can be provided between the intermediate valve sealing surface and the intermediate seat sealing surface.

In a further aspect, the intermediate valve member comprises an inner surface portion for interfacing the distal support member, and wherein the intermediate valve member is flexible and can be changed from a normal configuration to a forced configuration, in response to a fluid pressure on the inner surface portion.

In a further aspect, the normally closed configuration of the flow communication unit further comprises, the intermediate valve member being in the normal configuration and provides the intermediate fluid tight seal.

In a further aspect, the intermediate valve member is positioned in the distal portion of the first channel, and provides additional safety.

In some embodiments and in a further aspect, the outlet sealing member is provided by the outlet barrier.

In some embodiments and in a further aspect the flow communication unit further comprises:
  a central portion extending from the inlet surface to the outlet surface, wherein the central portion provides a portion of the inlet surface and the outlet surface, and wherein the central portion comprises the first flow channel, the central portion further comprises a side surface extending in a direction between the inlet and the outlet surface, wherein the channel outlet and the first outlet valve member is provided in the side surface, and wherein the first outlet valve member surrounds the channel outlet,
  wherein the outlet barrier surrounds the central portion and provides the second outlet valve member, wherein the outlet barrier is movably arranged and can be moved between a distal position and a proximal position,
  wherein the outlet surface can be arranged in the connected configuration, when the outlet barrier is positioned in the proximal position,
  wherein the outlet surface can be arranged in the unconnected configuration, when the outlet barrier is positioned in the distal position,
  wherein a circumferential portion connected to the central portion, provides the intermediate surfaces extending between the inlet surface and the outlet surface, wherein the circumferential portion comprises a portion of the inlet and the outlet surface,
  wherein the inlet surface, the outlet surface and the intermediate surfaces define the outer surface and confines the interior space of the flow communication unit, for the outlet surface being in any of the connected and the unconnected configurations, wherein the outlet barrier is positioned proximally or distally,
  wherein the outlet sealing member is provided in the side surface of the central portion, and wherein the outlet sealing member surrounds the channel outlet, whereby the outlet sealing member provides a portion of the outlet surface in the connected configuration,
  wherein the outlet barrier provides a portion of the outlet surface,
  wherein the outlet surface provided by the outlet barrier is flush with the outlet portions provided by the central and the circumferential portion, when the outlet surface is in the unconnected configuration, whereby it is easier to keep the outlet surface clean, and
  wherein the outlet surface provided by the outlet barrier is depressed relative to outlet surface portions provided by the central and the circumferential portion, when the outlet surface is in the connected configuration,
  wherein the second outlet valve member is adapted to cooperate with the first outlet valve member to provide an outlet barrier seal, wherein the outlet barrier is adapted for being in:
  (i) a closed configuration, wherein the outlet surface is in the unconnected configuration, whereby the outlet barrier is in the distal position, and whereby the outlet barrier seal is adapted to reduce the entrance of contaminations, and (ii) a flow configuration, wherein the outlet surface is in the connected configuration, whereby the outlet barrier is in the proximal position, whereby the outlet barrier is adapted to allow a drug contained in the first channel to flow downstream from the channel inlet and out of the channel outlet, in response to the pressure in the first channel being above the first threshold;

wherein the flow communication unit is further adapted for being in:

(i) the unconnected configuration, in response to disconnecting the flow communication unit from the flow conducting device, and wherein the outlet barrier is allowed to be in the closed configuration, and (ii) the connected configuration, in response to connecting the flow communication unit to the flow conducting device, wherein the outlet barrier is allowed to be in the flow configuration, wherein the outlet sealing member is arranged to be able to contact the flow conducting device to provide the channel seal downstream to the channel outlet to allow flow communication between the channel outlet and the flow conducting device, wherein the channel outlet for the first channel is arranged at the outlet surface of the flow communication unit; and wherein a combined flow channel can be provided between the drug delivery device, the first channel and the flow conducting device with the channel seal arranged downstream to the channel outlet, when the channel inlet is arranged in flow communication with the drug delivery device and the flow communication unit is in the connected configuration;

whereby the flow communication unit is adapted to enable the extended use of the multi-use drug delivery device, and whereby the flow communication unit is adapted to inhibit microbial entrance in the multi-use drug delivery device during the extended use.

In a further aspect, the flow communication unit further comprises an outlet barrier locking member adapted to be released by the flow conducting device upon connection, wherein the outlet barrier is further adapted for being in:

(i) the closed configuration, wherein the outlet surface is in the unconnected configuration, wherein the outlet barrier is locked by the outlet barrier locking member in the distal position, and (ii) a flow configuration, wherein the outlet surface is in the connected configuration, wherein the outlet barrier is released and allowed to be moved to the proximal position.

In a further aspect, the flow communication unit comprises a closure for the multi-use drug delivery device adapted to permit withdrawal of the drug formulation without removal or destruction of the closure.

In a further aspect, the barrier locking member is further adapted for being released by a connecting member of the flow conducting device.

In some embodiments and in a further aspect, a drug delivery system comprises the flow communication unit according to the present disclosure, the drug delivery device and the flow conducting device.

In a further aspect, the drug delivery system further comprises a cap for integrating the flow communication unit with the drug delivery device.

In a further aspect, the distal support member and the cap are adapted to clamp a portion of the outlet barrier, and whereby the clamped portion is fixed and the unclamped portion adapted to be moved between the normal and the forced configuration.

BRIEF DESCRIPTION OF THE DRAWINGS

In the following embodiments of the invention will be described with reference to the drawings:

FIG. 1E shows an infusion set which can be used in combination with embodiments of the present disclosure.

FIGS. 3A-3C illustrate in cross-sections a further embodiment of a drug delivery system in different assembly states according to the present disclosure, wherein the system comprises a flow conducting device, flow communication unit with a piercing needle to establish fluid communication with a drug delivery device, and the drug delivery device.

In the figures like structures are mainly identified by like reference numerals.

DESCRIPTION OF EXEMPLARY EMBODIMENTS

Figure 1A:
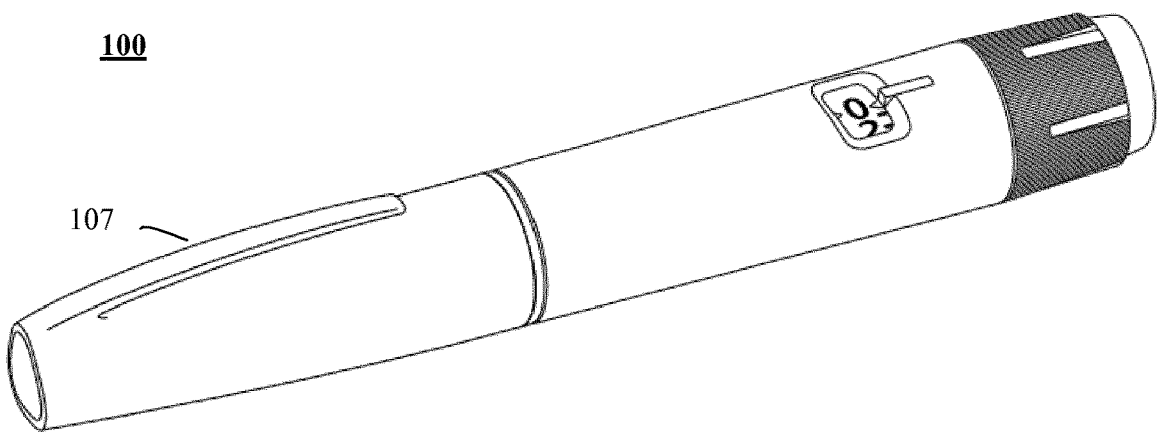
FIGS. 1A, 1B show an example of a drug delivery device in the form of an injection device. The injection device is shown with and without a protecting cap.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member is used for a given component it can be used to define a unitary component or a portion of a component, having a one or more functions.

Before turning to embodiments of the present invention per se, an example of an automatic drug delivery device in the form of an automatic injection device for multiple injection, and a drug delivery device in the form of continuous infusion device will be described. The described drug delivery devices provide the basis for the exemplary embodiments of the present invention.

The automatic drug delivery device is a prior art resettable dial-up/dial down automatic drug delivery device will be described. The pen device 100 comprises a cap part 107 and a main part having a proximal body or drive assembly portion with a housing 101 in which a drug expelling mechanism is arranged or integrated, and a distal cartridge holder portion 110 in which a drug-filled transparent cartridge 120 with a distal needle-penetrable septum is arranged and retained in place by a cartridge holder attached to the proximal portion, the cartridge holder having a pair of opposed openings 111 allowing a portion of the cartridge to be inspected. Distal coupling means 115 allows a needle assembly to be releasably mounted in fluid communication with the cartridge interior. The cartridge is provided with a piston driven by a piston rod forming part of the expelling mechanism and may for example contain an insulin, GLP-1 or growth hormone formulation. A proximal-most rotatable dose setting member 140 serves to manually set a desired dose of drug shown in display window 102 and which can then be expelled when the button 190 is actuated. Depending on the type of expelling mechanism embodied in the drug delivery device, the expelling mechanism may comprise a torsion spring as in the shown embodiment which is strained during dose setting and then released to drive the piston rod when the release button is actuated. More specifically, during dose setting a drive member to which the spring is connected is rotated to a rotational position corresponding to the set dose, the drive member thereby being in an energized state. A scale drum with dose size numerals is coupled to the drive member such that the size of the currently set dose is shown in the display window, e.g. by means of a threaded connection with the housing. To prevent the drive member from rotating the dose setting mechanism is provided with a holding mechanism, which in the exemplary embodiment is in the form of a ratchet mechanism (not shown on figure). When the user desires to expel the set dose the button is actuated whereby the drive member is brought into engagement with the piston rod drive mechanism and the holding mechanism subsequently released.

Figure 1B:
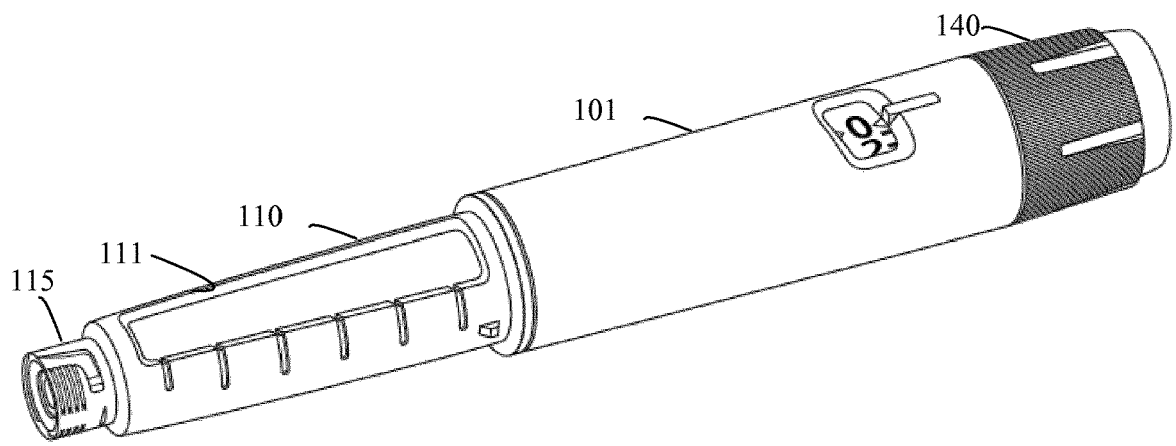
Figure 1C:
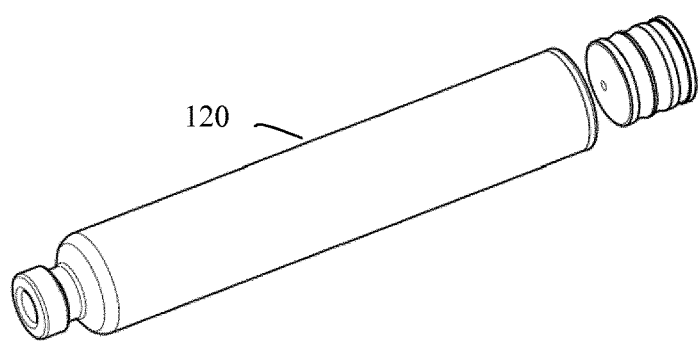
FIG. 1C shows a pressurizable drug reservoir in the form of a cartridge, which can be inserted into the drug delivery device shown in FIGS. 1A and 1B

Although FIGS. 1A, 1B and 1C show a drug delivery device of the pre-filled type, i.e. it is supplied with a pre-mounted cartridge and is to be discarded when the cartridge has been emptied, in alternative embodiments the drug delivery device may be a durable device designed to allow a cartridge assembly to be replaced, e.g. in the form of a cartridge assembly comprising a cartridge mounted in a cartridge holder. Such an assembly may further be provided with a pre-mounted piston rod.

Figure 1D:
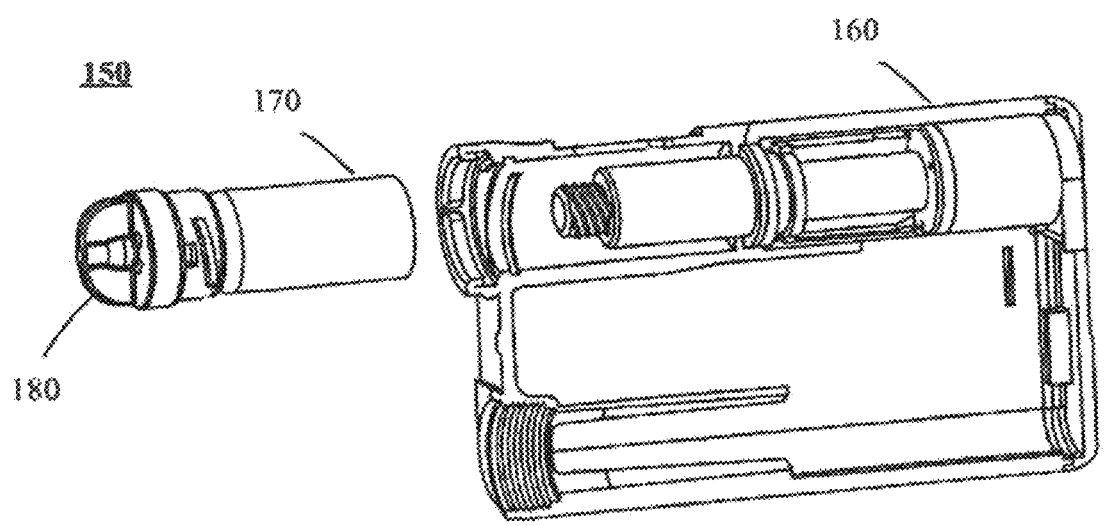
FIG. 1D shows an example of a drug delivery device in the form of an infusion pump. The drug delivery device is shown with a pump cartridge which is to be inserted into the drug delivery device.

FIG. 1D shows a drug delivery device 150 in the form of a continuous infusion pump, as disclosed by Medtronic Minimed in U.S. Pat. No. 6,248,093. The figure shows a pump housing 160, a pump cartridge 170, and a hub 180 for an infusion set. FIG. 1E shows an infusion set with a hub 180.

Preservatives are normally needed to prevent microbial or bacterial growth in drug formulations for extended or multiple. In products from Novo Nordisk A/S, one or both of the preservatives phenol and m-cresol are used to ensure that minor microbial contaminations will not grow during the expected lifetime of a multi dosed injectable. However, phenol and m-cresol are toxic (which is required for them to work as intended) and may therefore as a side effect cause injection site reactions, or in some cases allergic reactions. This also means that additional restrictions applies to the selection of new protein/peptide drugs, since they are required to be preservative stabile, especially when the drug product is intended for daily or weekly use. Thus, it would in some cases be preferred to be able to reduce or omit the addition of preservatives to a given drug. It should be noted that substances that are regarded as preservatives may be added in lower amounts with the purpose of acting as stabilizer of the drug substance, e.g., insulin substances.

To ensure antimicrobial requirements can be met without adding preservatives to the drug itself, two major issues must be addressed. Firstly, it must be ensured that a contaminated needle or cannula cannot be inserted in the cartridge and introduce microbial contamination of the cartridge. Secondly, it must be ensured that backflow through the cannula is not possible which would introduce a risk of microbial contamination through backflow of body fluids from the user. This concept should not be confused with known arrangements in which preservative-filled reservoirs are provided to allow a subcutaneous needle to safely be used more than once, e.g. as disclosed in U.S. Pat. No. 3,354,881 and WO 2014/064100.

Flow Communication Unit

With reference to FIGS. 2-4 exemplary embodiment of the drug delivery system are illustrated for the purpose of describing the different assembly states of the system according to the present disclosure, and for describing common features. The drug delivery system 200, 300, 400 is adapted for subcutaneous delivery of a drug during extended use, the drug delivery system comprises the components: (i) a multi-use drug delivery device 210 comprising a reservoir 211 comprising a drug formulation allowing microbial growth upon introduction of microorganisms into the reservoir during extended use, (ii) a flow conducting device 230, and (iii) a flow communication unit 240 adapted to be connected to the multi-use drug delivery device and the flow conducting device, and adapted to enable a fluid flow from the drug delivery device to the flow conducting device and to restrict the entrance of contaminations into the drug reservoir. In other words, the flow communication unit is adapted to promote bacteriostatic conditions for a drug formulation, wherein the drug formulation, in itself, may allow microbial growth and may comprise insufficient concentrations of preservatives to preserve the drug formulation, if the drug formulation is contaminated with microorganisms. More specific, the flow communication unit is adapted to promote bacteriostatic conditions by preventing the introduction of microorganisms, which can be achieved by the features described in present disclosure.

The illustrated drug delivery device 210 comprises the reservoir 211, wherein the reservoir comprises a volume of liquid drug with no preservatives or a small concentration of preservatives, and the volume of liquid drug can be delivered during extended use. Delivery during extended use can be used to describe a medical treatment regimen or mode of delivery, wherein the drug is to be delivered by infusion or multiple injections using a drug delivery device adapted for the purpose. For example and more specific, a medical regimen prescribing delivery during extended use may comprise (i) the delivery of a plurality of smaller volumes (smaller volume) in a near continuous delivery by infusion, (ii) the delivery of a plurality of larger volumes (larger volume) of bolus deliveries by infusion or (iii) the delivery of a plurality of larger volumes (larger volume) of bolus deliveries by multiple injections.

In this context, the volume of a smaller volume can be understood as being smaller than the volume of a larger volume, wherein the drug, as an example, can be U100 insulin, and whereby the reservoir comprises 3 ml of 300 units. In this case the volume of each unit is 0.01 ml. Depending on the incremental step size of the dose setting mechanism or the stroke volume of the drug delivery device, the volume of a smaller volume can, as an example, be 0.001 ml or 0.01 ml, or a volume within the interval between the two examples. Similarly the volume of a larger volume can be 0.01 ml or 0.10 ml, or a volume within the interval between the two examples.

Also in this context, near continuous delivery of the drug, can be the delivery of a plurality of the smaller volumes within short delivery intervals (short delivery interval), e.g. 5 seconds, 60 seconds, or 300 seconds, and the extended use can be over a longer period (longer period), e.g. a plurality of calendar days, e.g. 3 calendar days. In this case, the flow conducting device may comprise an infusion set or catheter enabling subcutaneous delivery to a subject.

Also in this context, bolus deliveries of the drug, can be the delivery of a plurality of the larger volumes within large delivery intervals (large delivery interval), e.g. an hour or a calendar day, the extended use can be over a longer period, e.g. a plurality of calendar days, e.g. 3 calendar days. In this case, the flow conducting device may comprise an infusion needle or catheter enabling subcutaneous delivery to a subject.

Also in this context, multiple injections of the drug, can be the delivery of a plurality of the larger volumes within large delivery intervals (large delivery interval), e.g. 1 hour, a calendar day or a week, the extended use can be over a longer period, e.g. a plurality of calendar days, e.g. 3, or a plurality of weeks, e.g. 5, and the flow conducting device may comprise an injection needle for subcutaneous delivery to a subject.

Figures 2A, 2B:
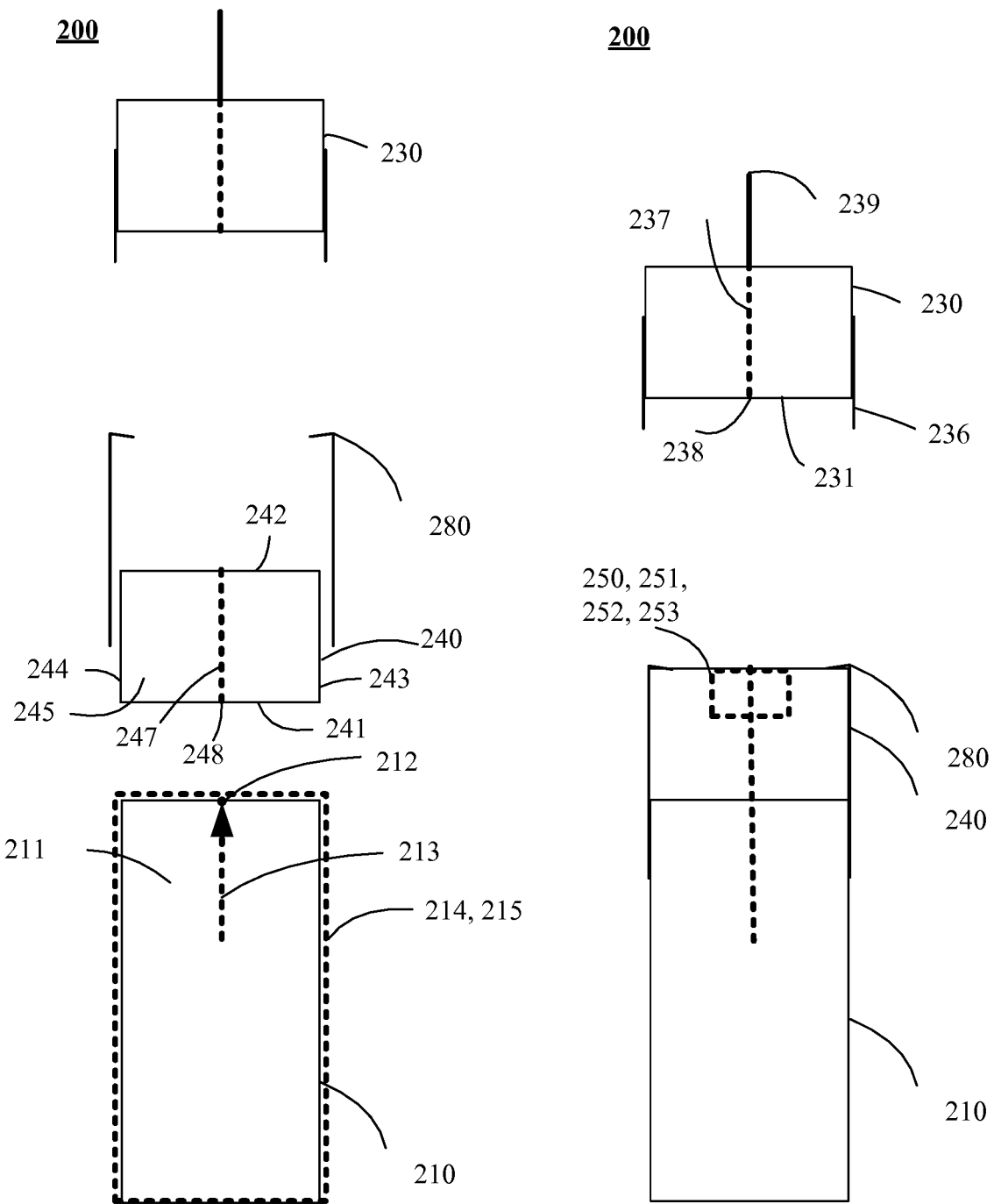
FIGS. 2A-2C illustrate in cross-sections an embodiment of a drug delivery system in different assembly states according to the present disclosure, wherein the system comprises a flow conducting device, flow communication unit with a needle less interface for interfacing the drug delivery device, and the drug delivery device.
Figure 3C:
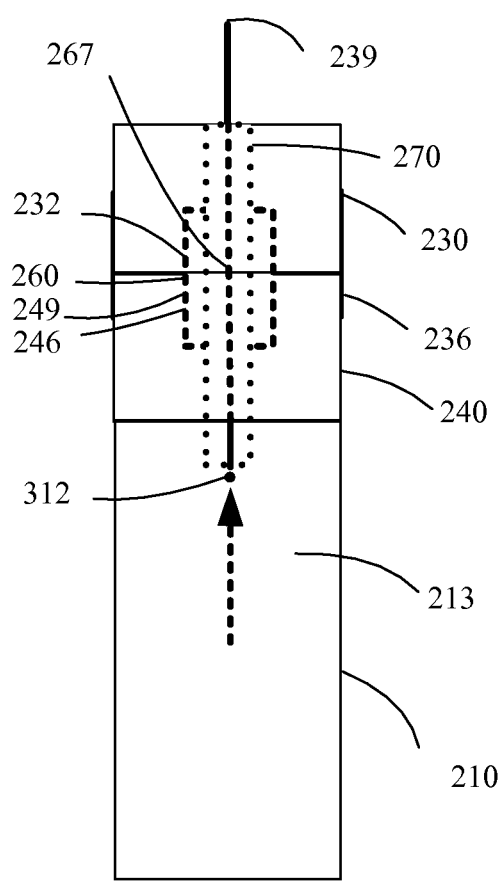
Figures 4A, 4B:
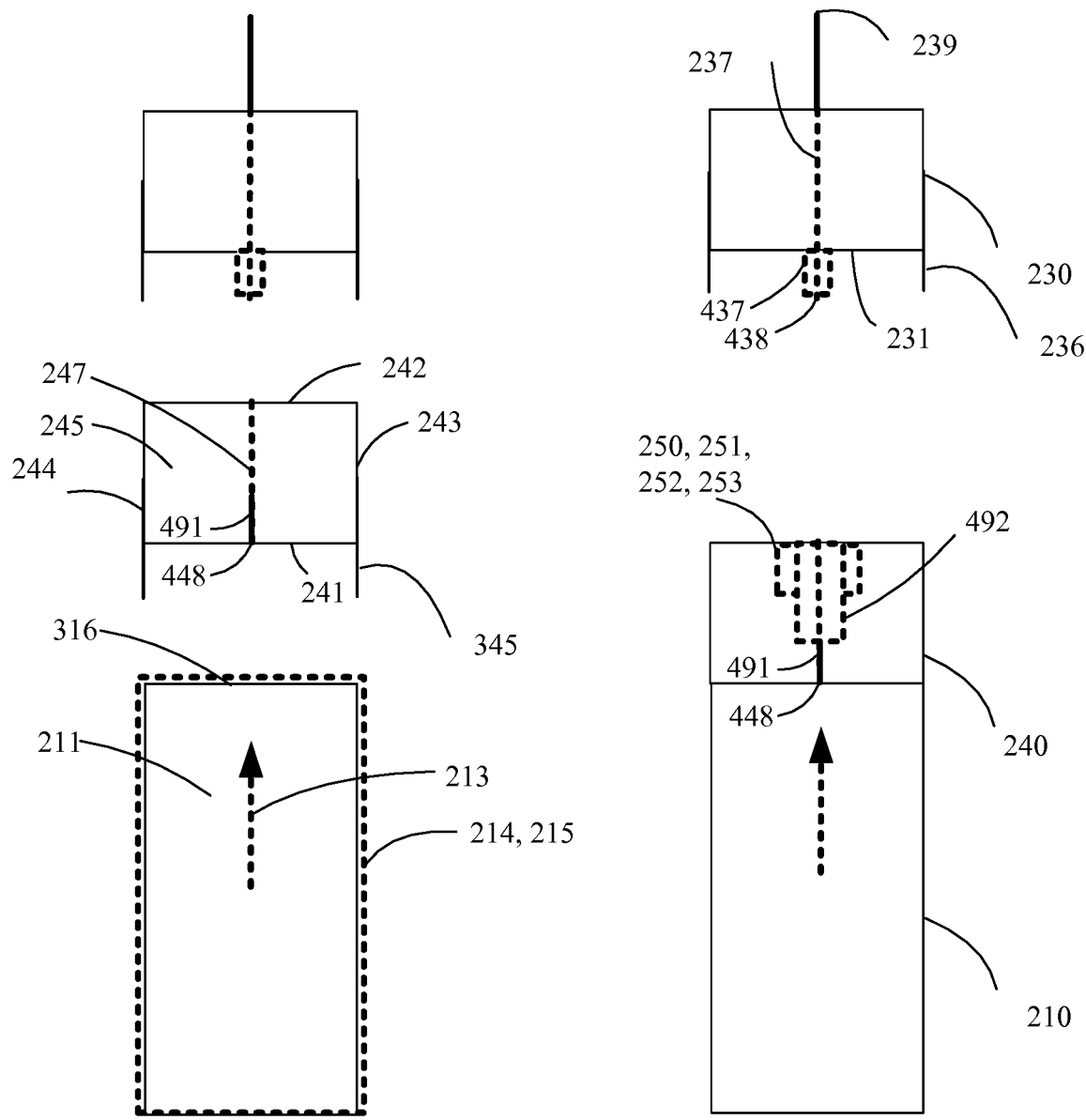
FIGS. 4A-4C illustrate in cross-sections a further embodiment of a drug delivery system in different assembly states according to the present disclosure, wherein the system comprises a flow conducting device, flow communication unit with an actuatable piercing needle to establish fluid communication with a drug delivery device, and the drug delivery device.
Figure 5A:
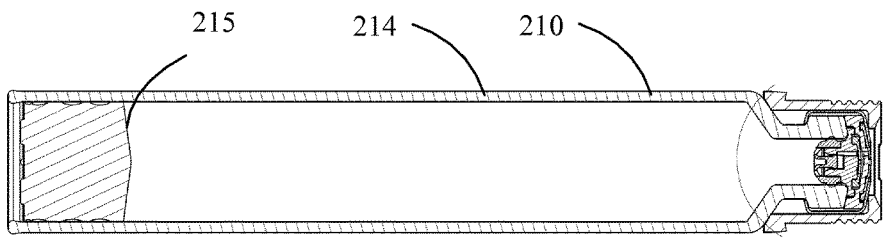
FIG. 5A shows in cross-section an embodiment of a drug delivery system according to the present disclosure, wherein the flow communication unit is connected with the drug delivery.
Figure 5B:
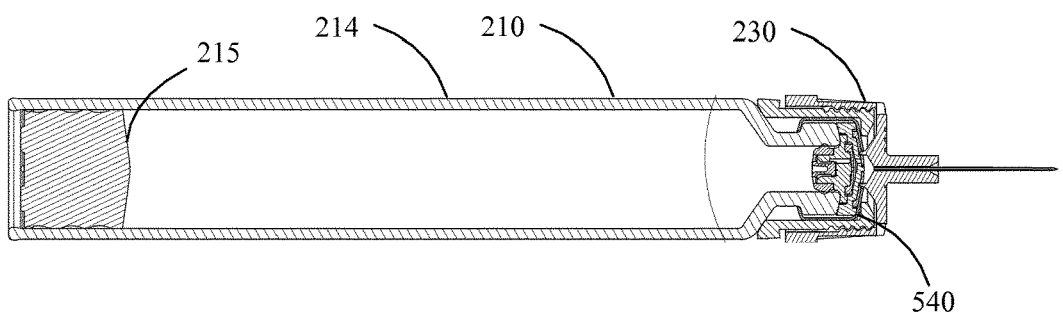
FIG. 5B shows in cross-section the drug delivery system of FIG. 5A, wherein the flow communication unit is connected with the drug delivery device and the flow conducting device.
Figure 5C:
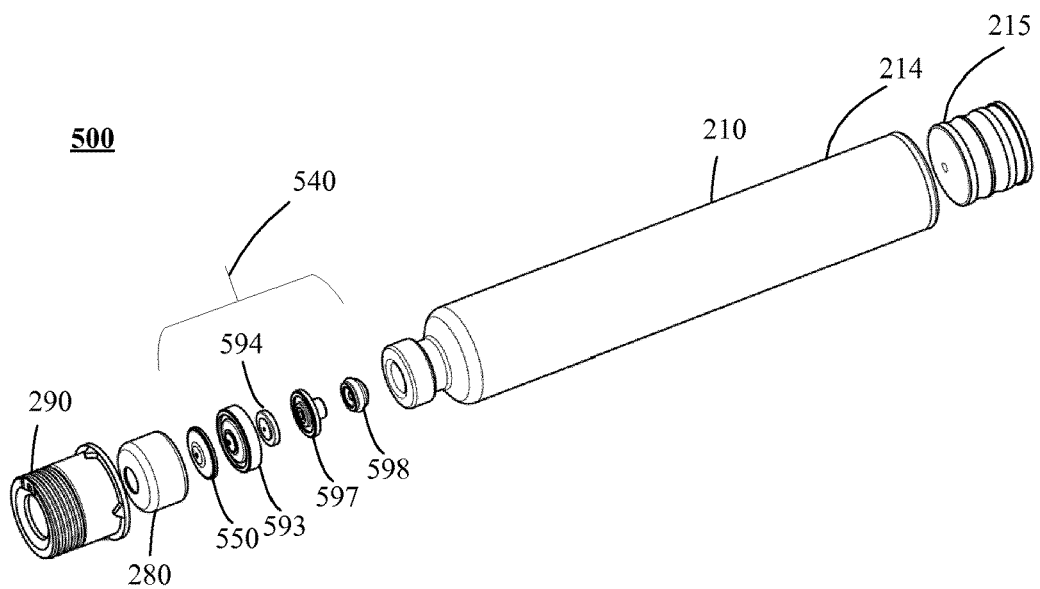
FIG. 5C shows an exploded view of the drug delivery system of FIG. 5A.
Figure 5D:
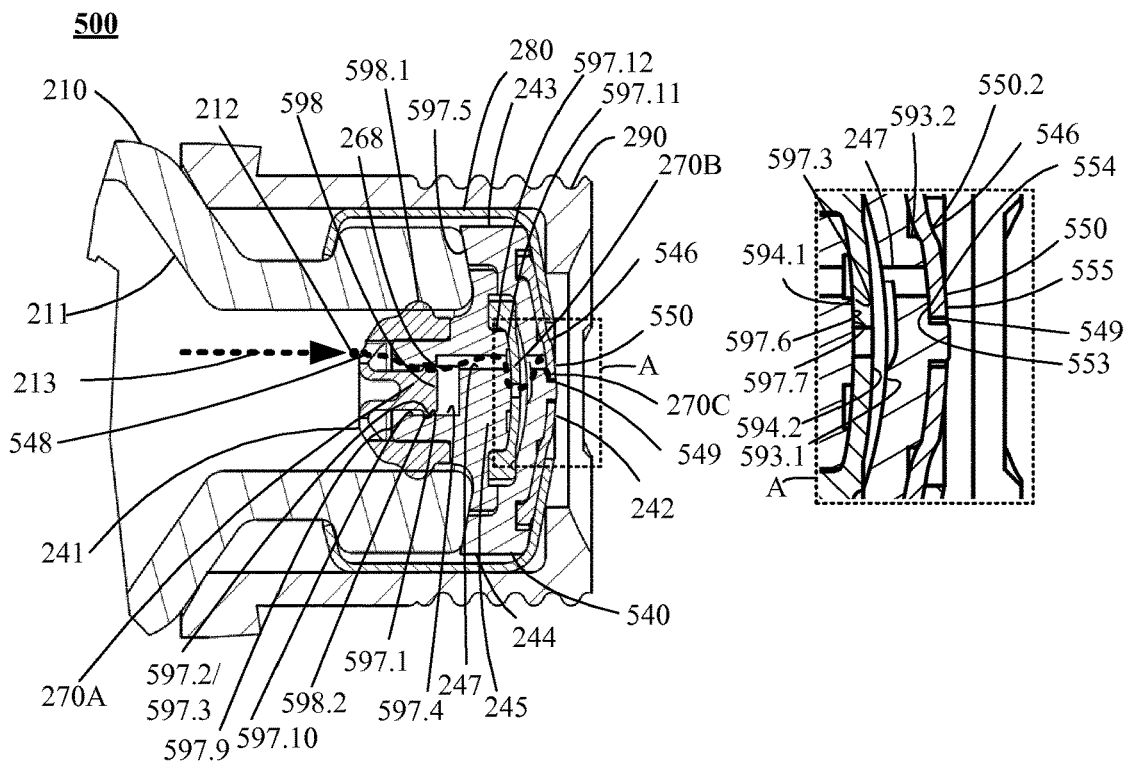
FIG. 5D left panel shows a close-up of the drug delivery system of FIG. 5A, and the right panel shows details of the left panel.
Figure 5E:
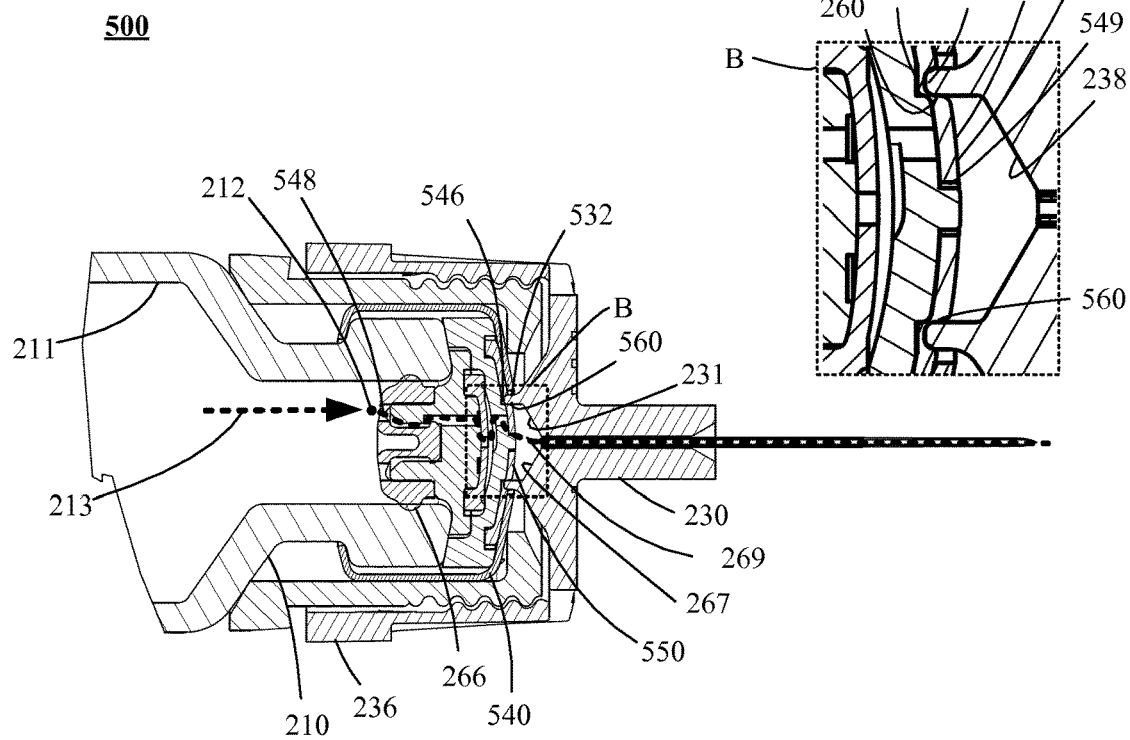
FIG. 5E left panel shows a close-up of the drug delivery system of FIG. 5B, and the right panel shows details of the left panel.
Figure 6A:
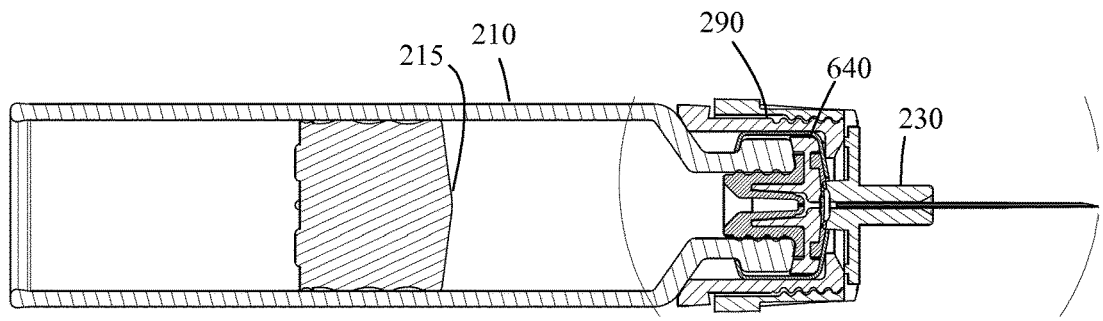
FIG. 6A shows in cross-section an embodiment of a drug delivery system according to the present disclosure, wherein the flow communication unit is connected with the drug delivery device and the flow conducting device.
Figure 6B:
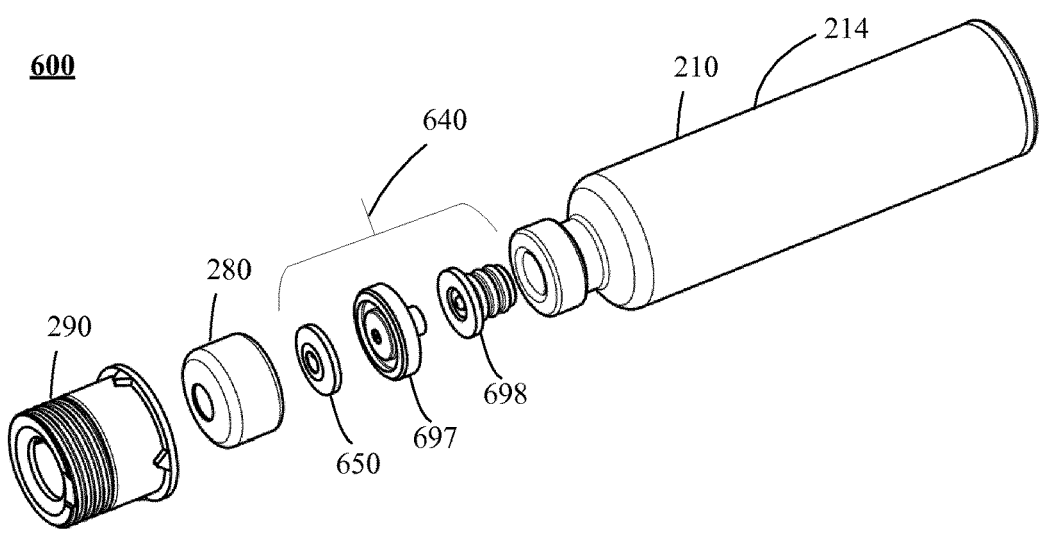
FIG. 6B shows an exploded view of the drug delivery system of FIG. 6A without the flow conducting device.
Figure 6C:
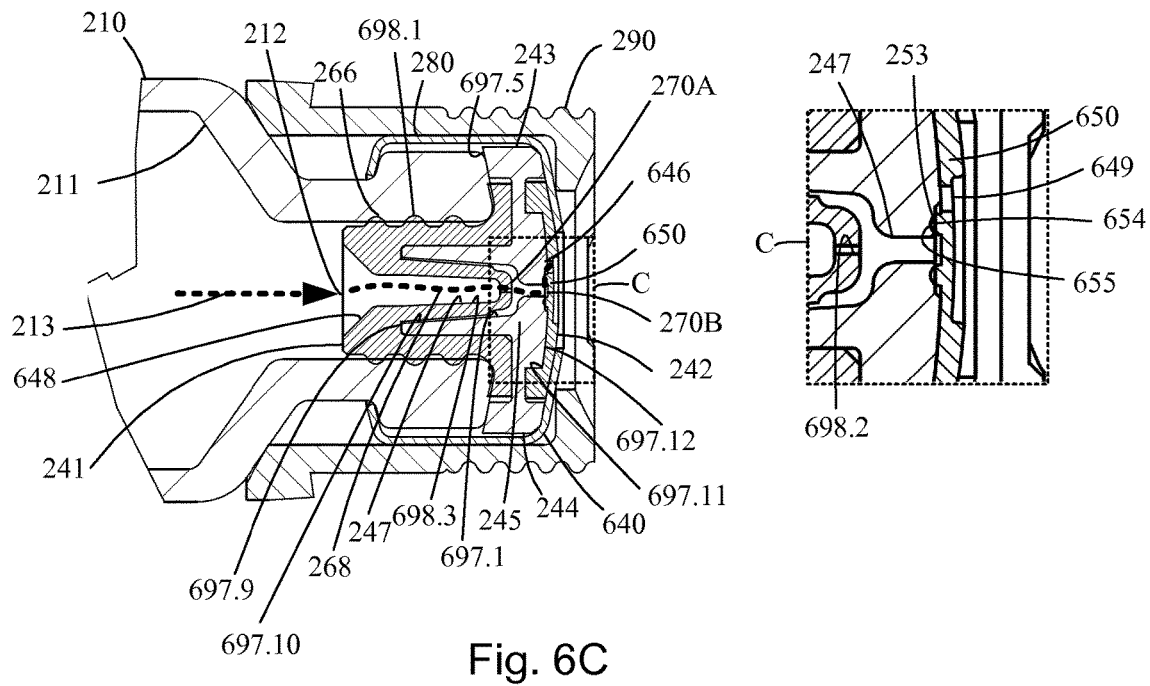
FIG. 6C left panel shows a close-up of the drug delivery system of FIG. 6A without the flow conducting device, and the right panel shows details of the left panel.
Figure 6D:
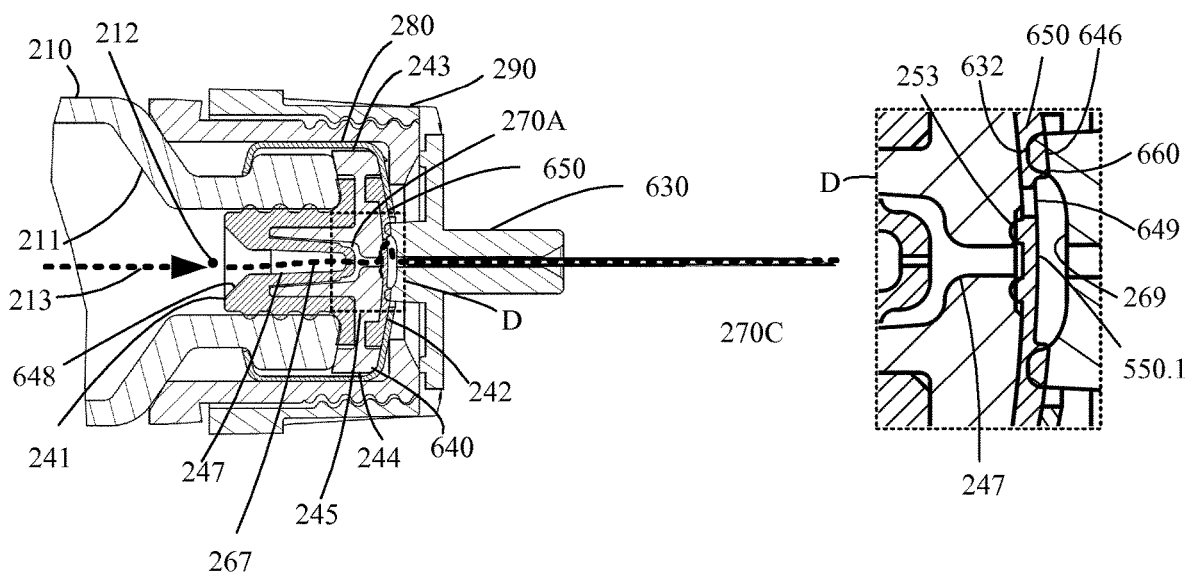
FIG. 6D left panel shows a close-up of the drug delivery system of FIG. 6A, and the right panel shows details of the left panel.
Figure 6E:
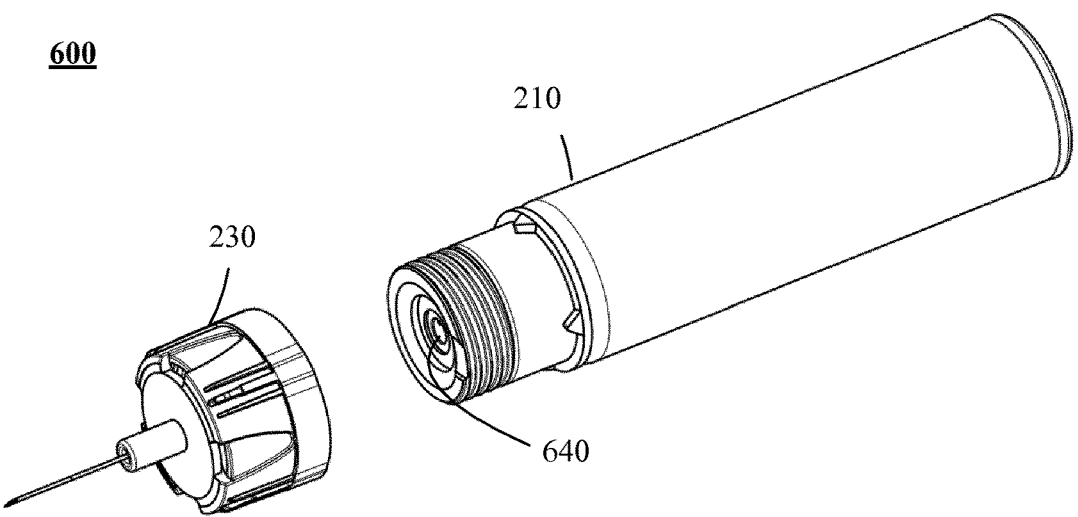
FIG. 6E shows a perspective view of the drug delivery system of FIG. 6A.
Figure 6F:
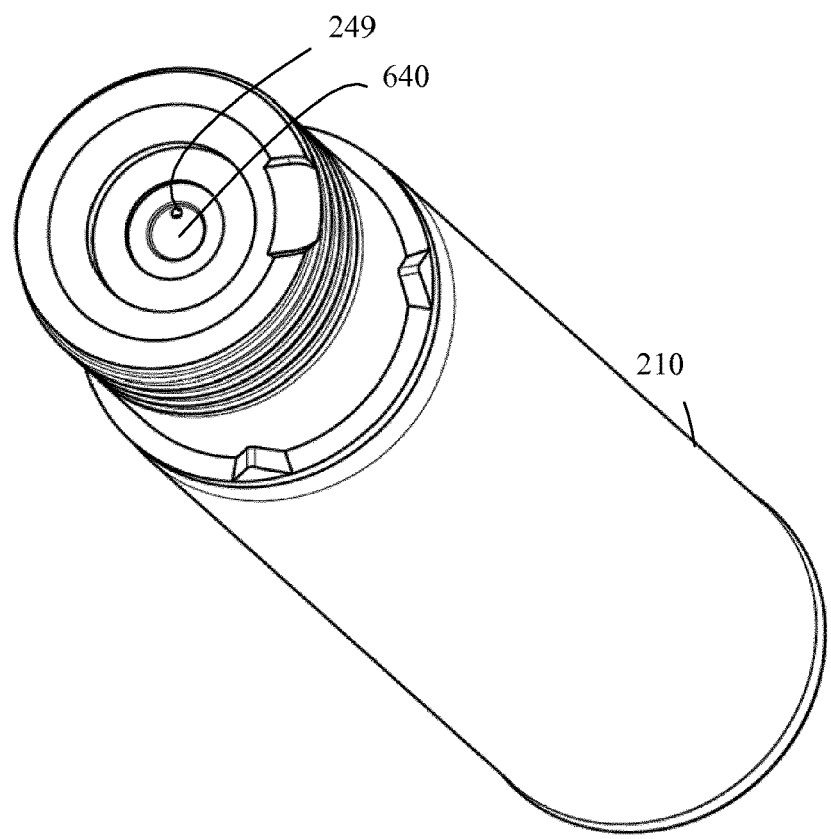
FIG. 6F shows a perspective view of the drug delivery system of FIG. 6A, and further illustrates details of the acentric position of the channel outlet.
Figure 7A:
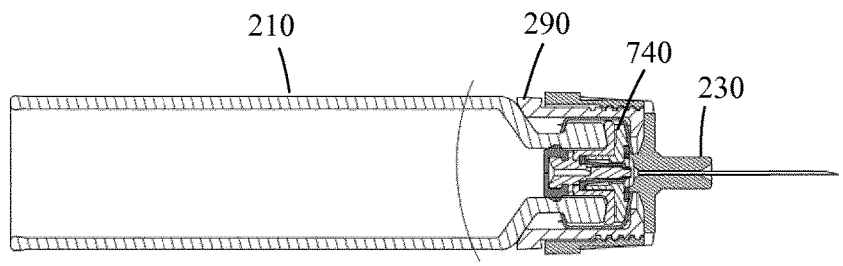
FIG. 7A shows in cross-section an embodiment of drug delivery system according to the present disclosure, wherein the flow communication unit is connected with the drug delivery device and the flow conducting device.
Figure 7B:
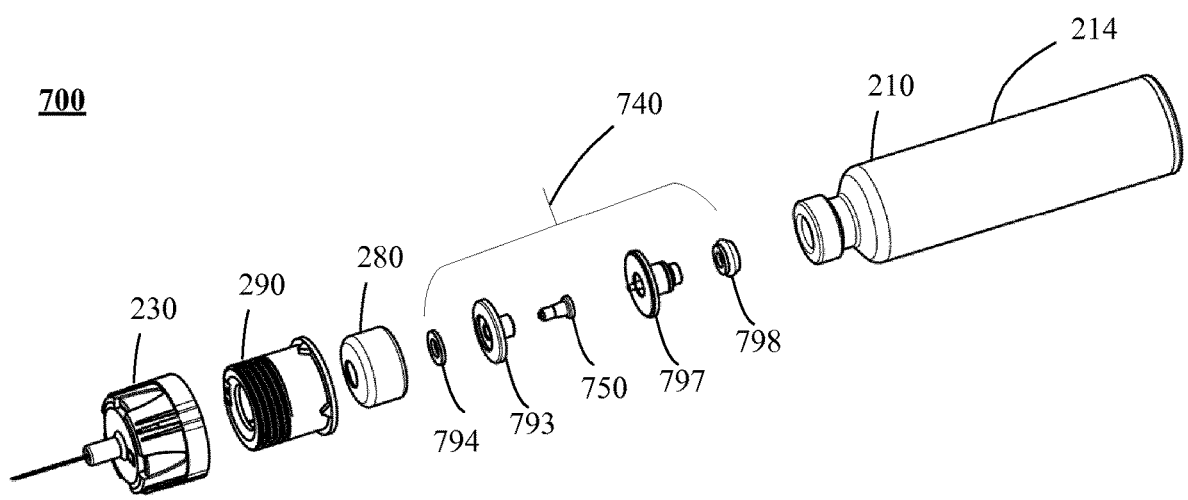
FIG. 7B shows an exploded view of the drug delivery system of FIG. 7A.
Figure 7C:
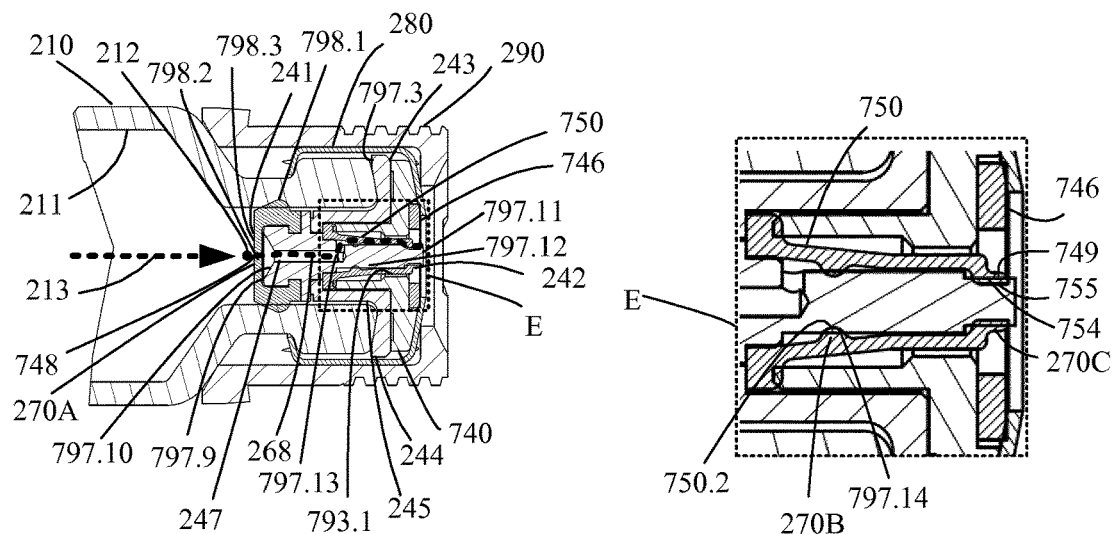
FIG. 7C left panel shows a close-up of the drug delivery system of FIG. 7A without the flow conducting device, and the right panel shows details of the left panel.
Figure 7D:
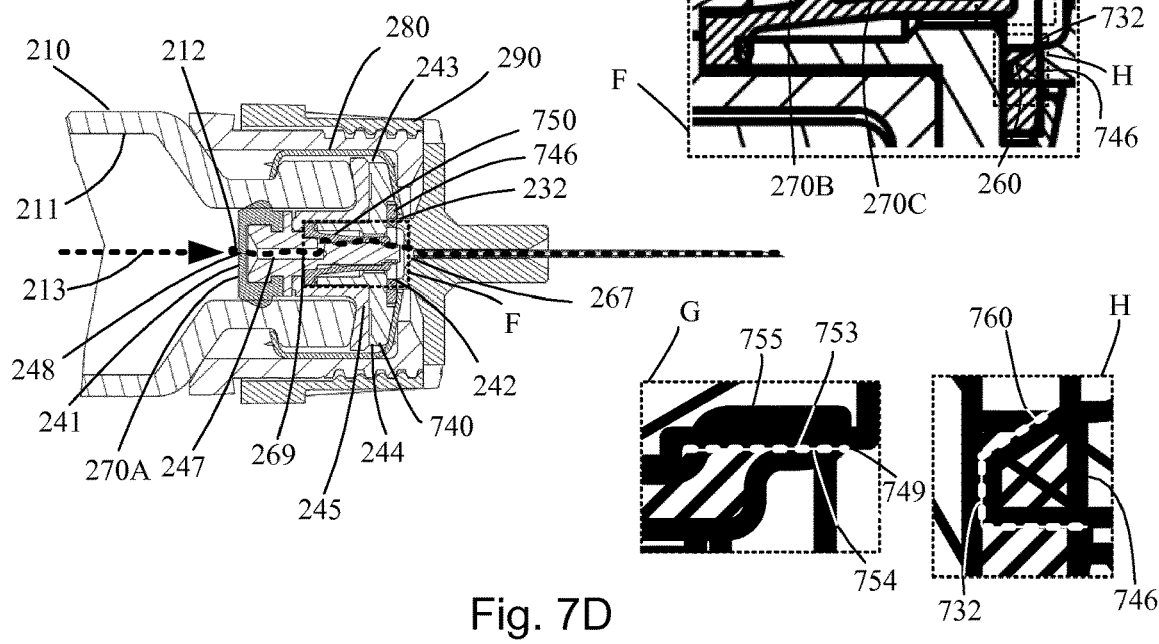
FIG. 7D left panel shows a close-up of the drug delivery system of FIG. 7A, and the right panel shows details of the left panel.
Figure 8A:
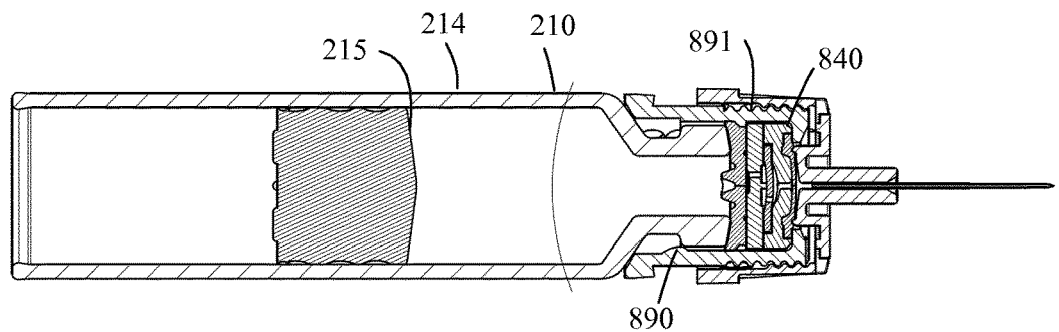
FIG. 8A shows in cross-section an embodiment of a drug delivery system according to the present disclosure, wherein the flow communication unit is connected with the drug delivery device and the flow conducting device.
Figure 8B:
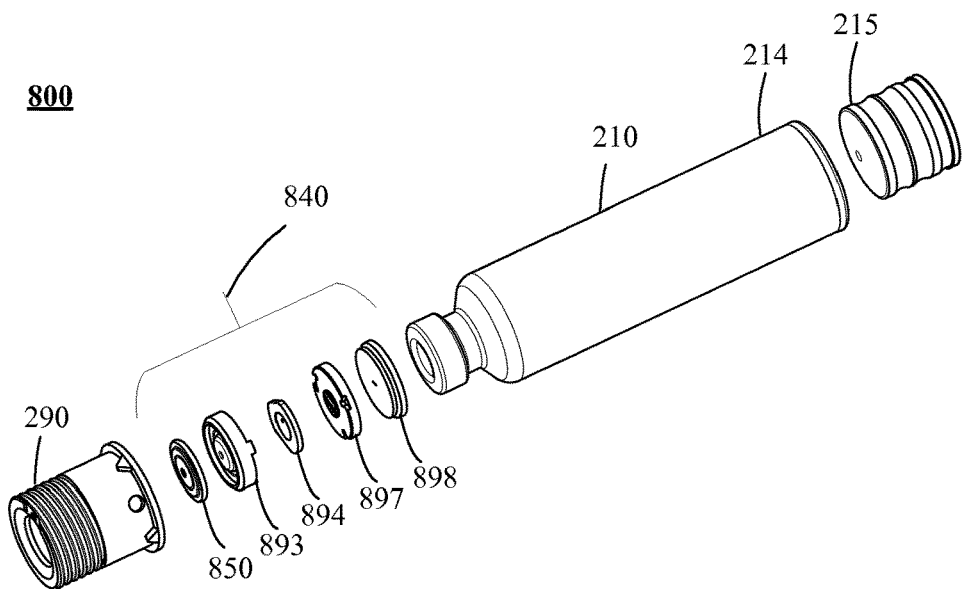
FIG. 8B shows an exploded view of the drug delivery system of FIG. 8A.
Figure 8C:
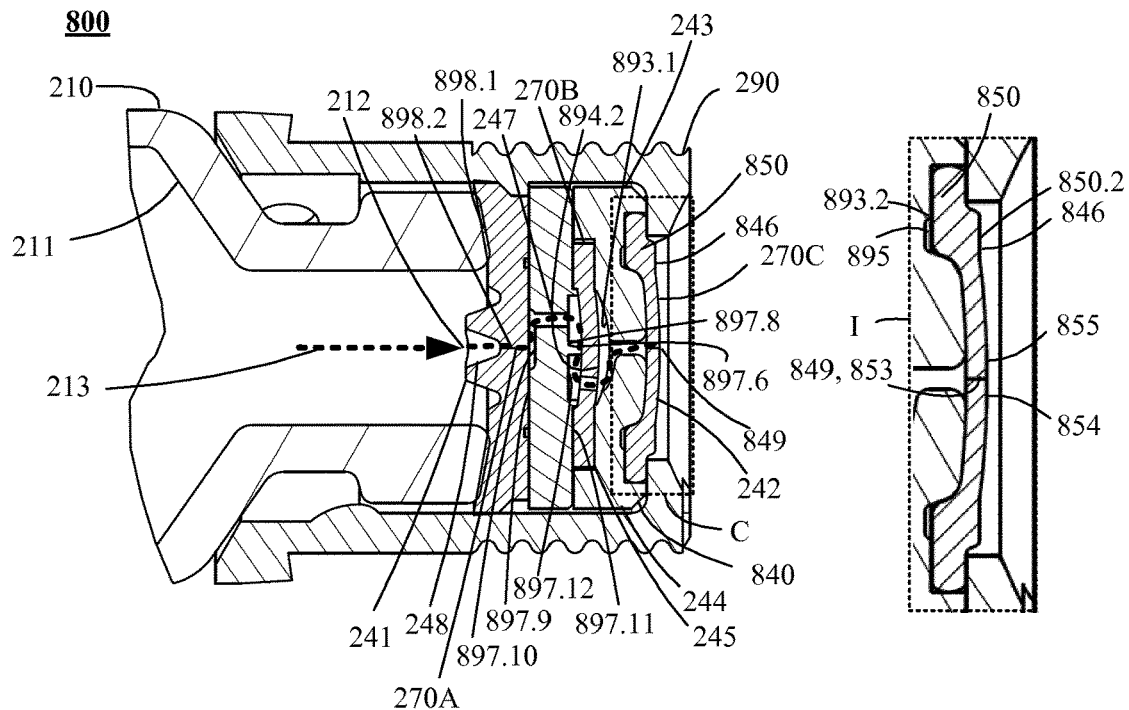
FIG. 8C left panel shows a close-up of the drug delivery system of FIG. 8A without the flow conducting device, and the right panel shows details of the left panel.
Figure 8D:
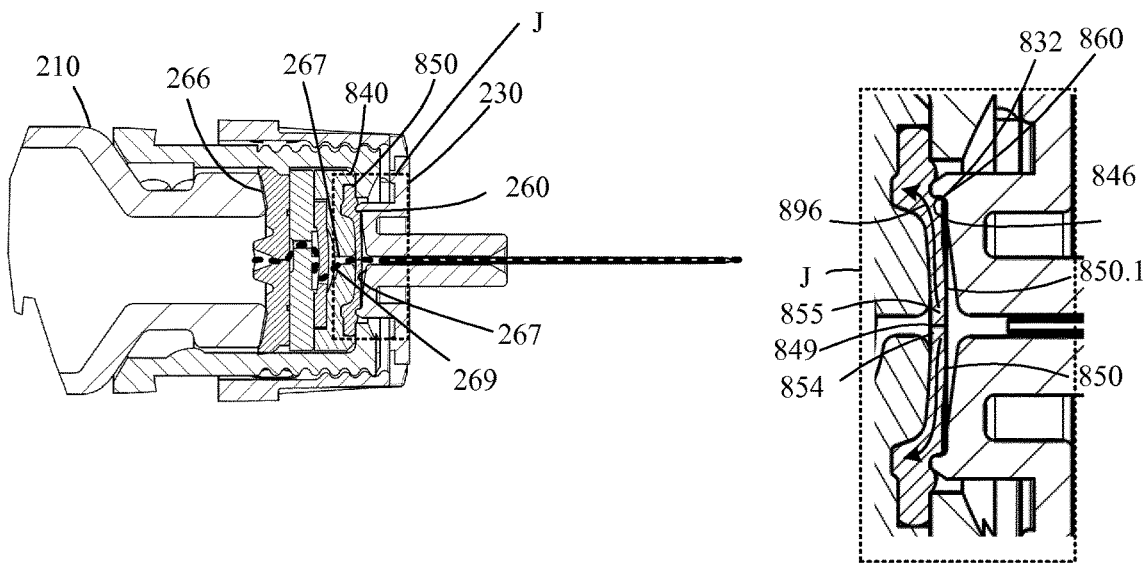
FIG. 8D left panel shows a close-up of the drug delivery system of FIG. 8A, and the right panel shows details of the left panel.
Figure 8E:
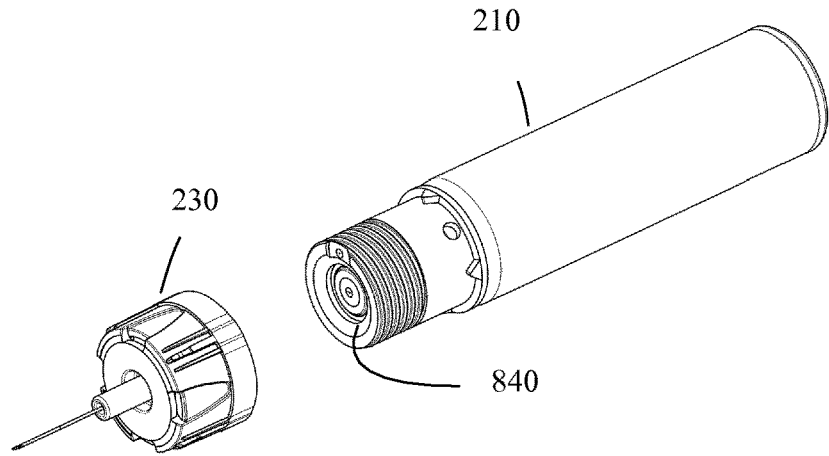
Figure 8F:
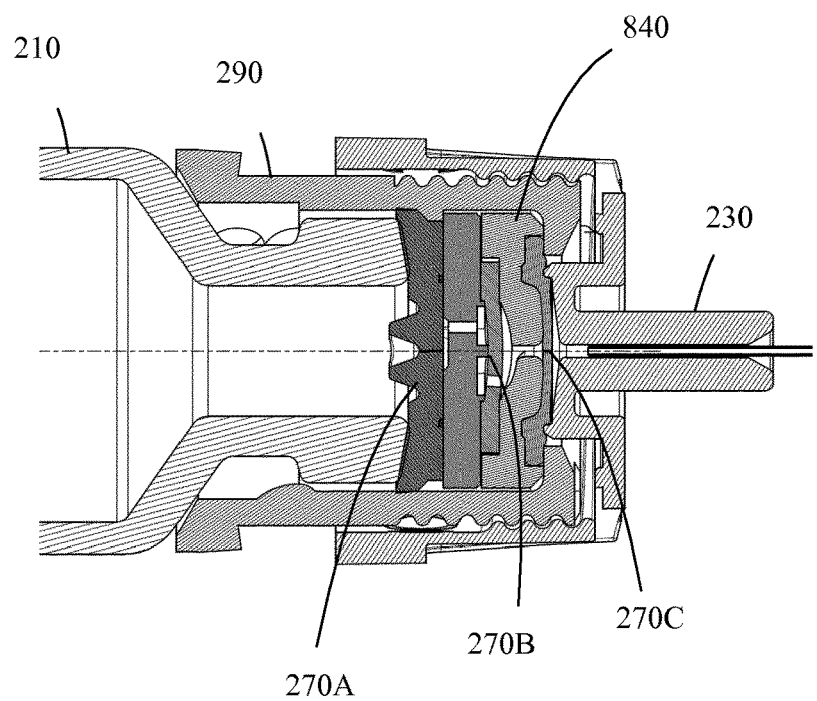
Figure 9A:
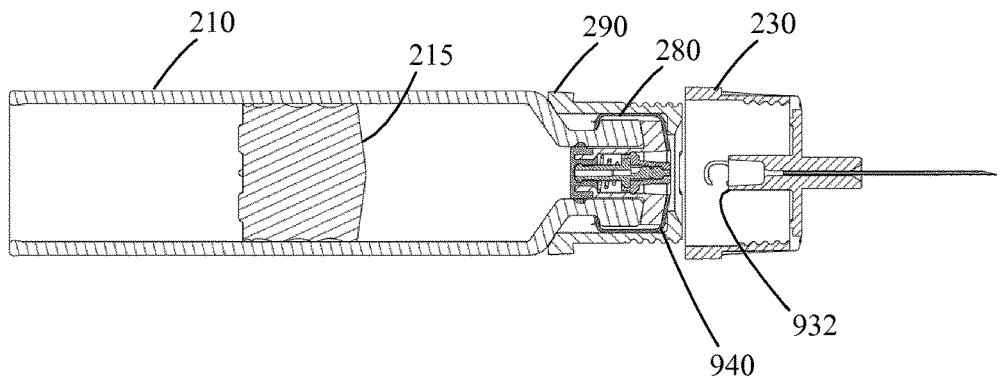
FIG. 9A shows in cross-section an embodiment of a drug delivery system according to the present disclosure, wherein the flow communication unit is connected with the drug delivery device. The figure also illustrates a flow conducting device.
Figure 9B:
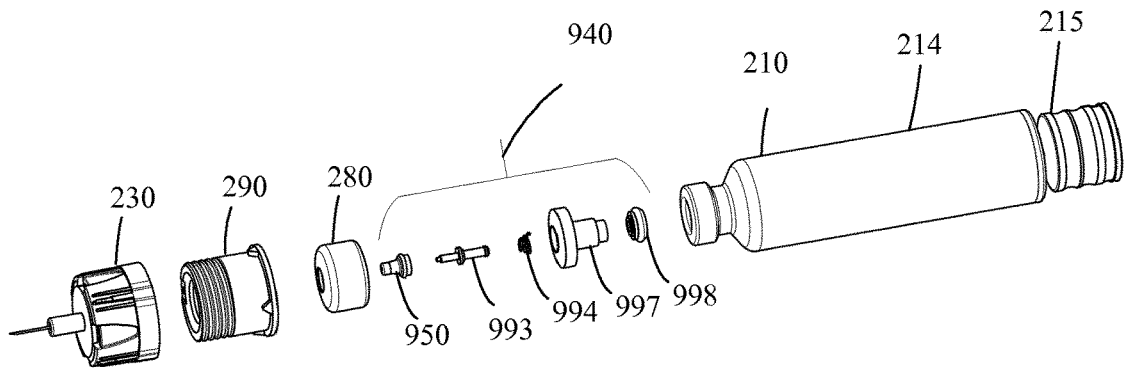
FIG. 9B shows an exploded view of the drug delivery system of FIG. 9A.
Figure 9C:
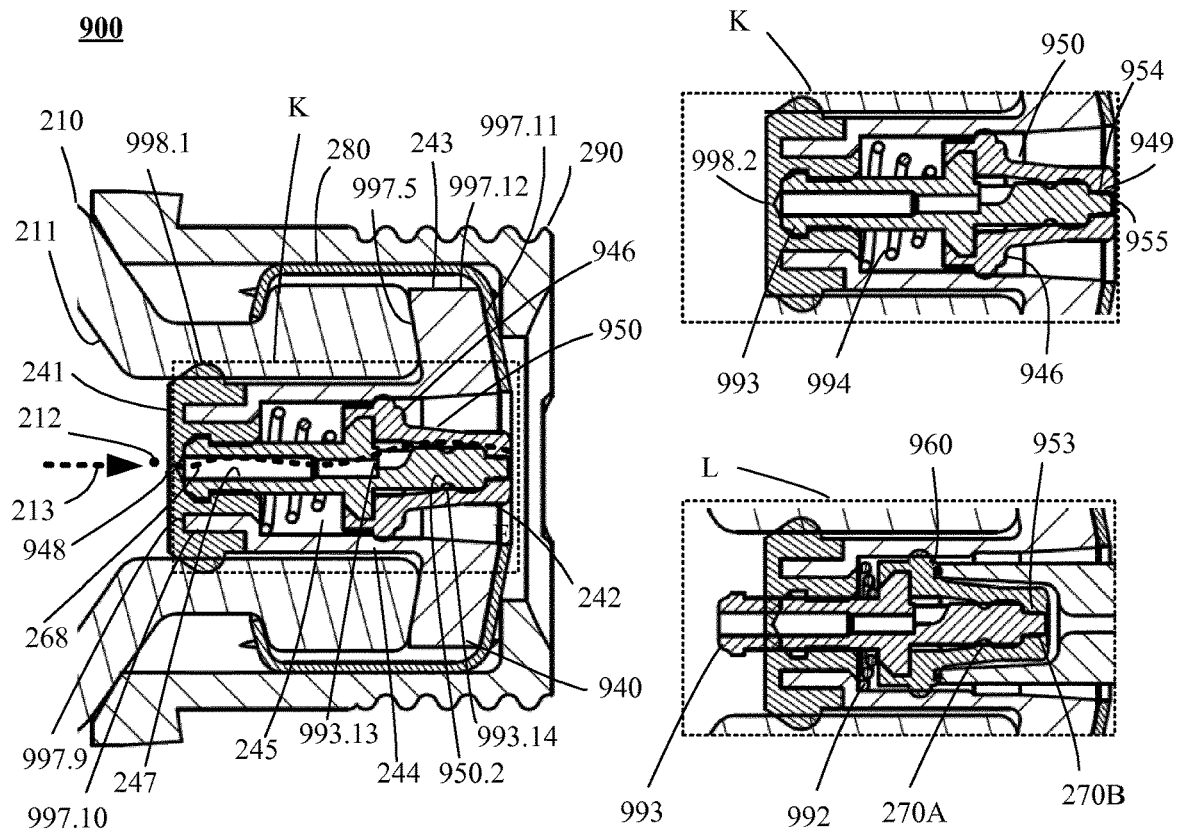
FIG. 9C left panel shows a close-up of the drug delivery system of FIG. 9A without the flow conducting device, and the right panel shows details of the left panel.
Figure 9D:
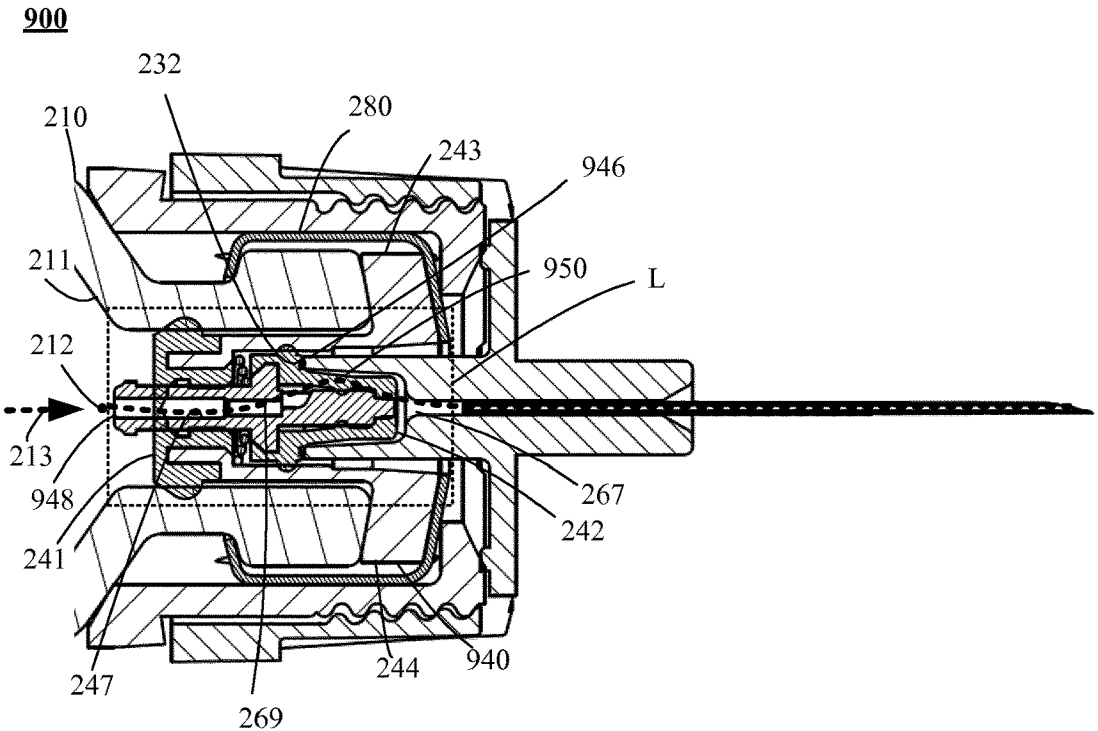
FIG. 9D left panel shows a close-up of the drug delivery system of FIG. 9A, and the right panel shows details of the left panel.
Figure 10A:
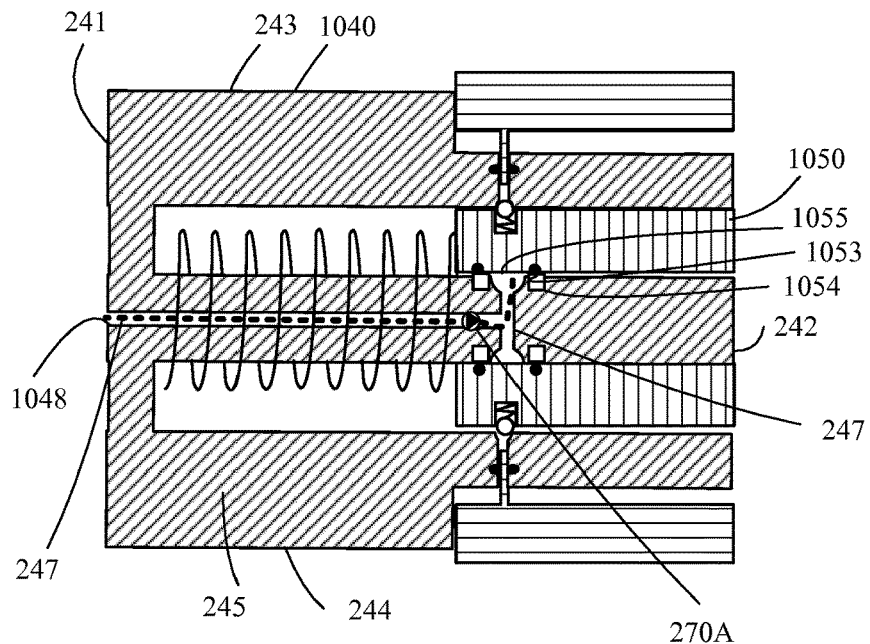
FIG. 10A illustrates in cross-section an embodiment of a drug delivery system according to the present disclosure, wherein the outlet barrier is locked in a distal position.
Figure 10B:
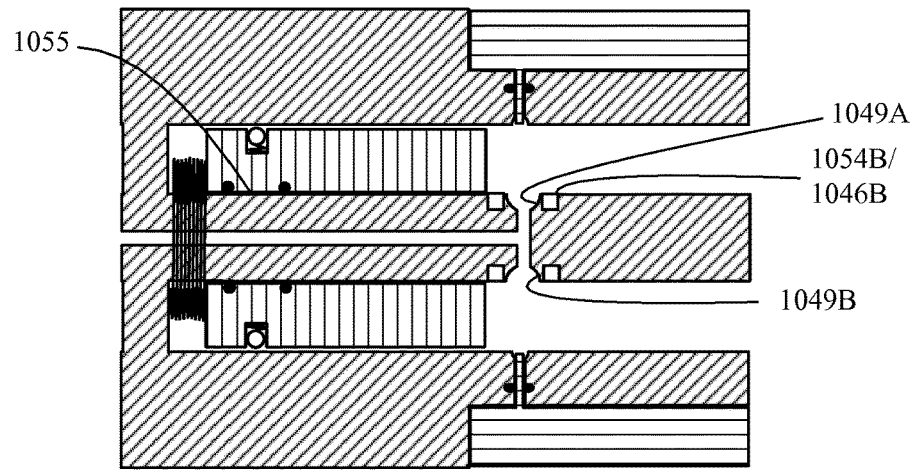
FIG. 10B illustrates in cross-section the drug delivery system of FIG. 10A, wherein the outlet barrier the lock is released and the outlet barrier is moved to a proximal position.
Figure 10C:
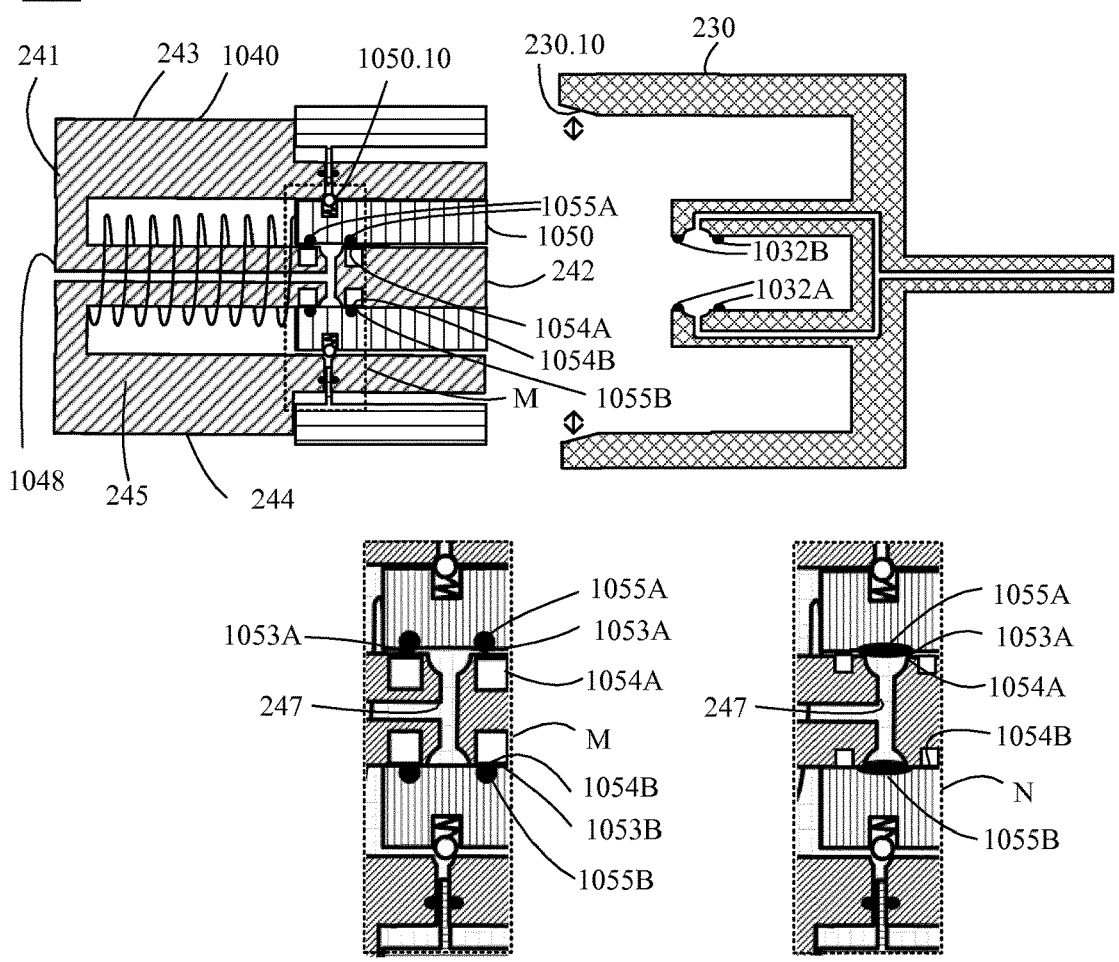
FIG. 10C upper portion illustrates in cross-section the drug delivery system of FIG. 10A, wherein the outlet barrier is locked in a distal position. The figure further illustrates a mating flow conducing device. The lower portion illustrates details.
Figure 10D:
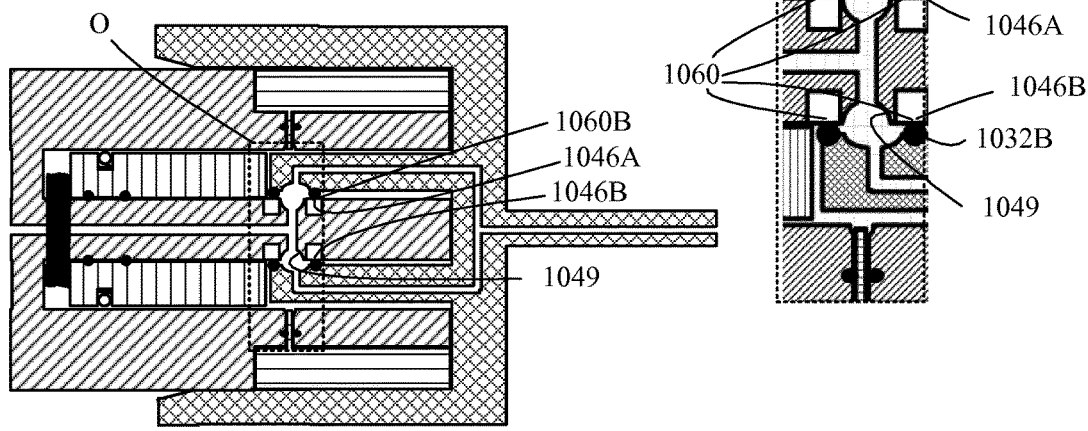
FIG. 10D left panel illustrates in cross-section the drug delivery system of FIG. 10A, wherein the outlet barrier the lock is released and the outlet barrier is moved to a proximal position. The right panel illustrates details.
Figure 10E:
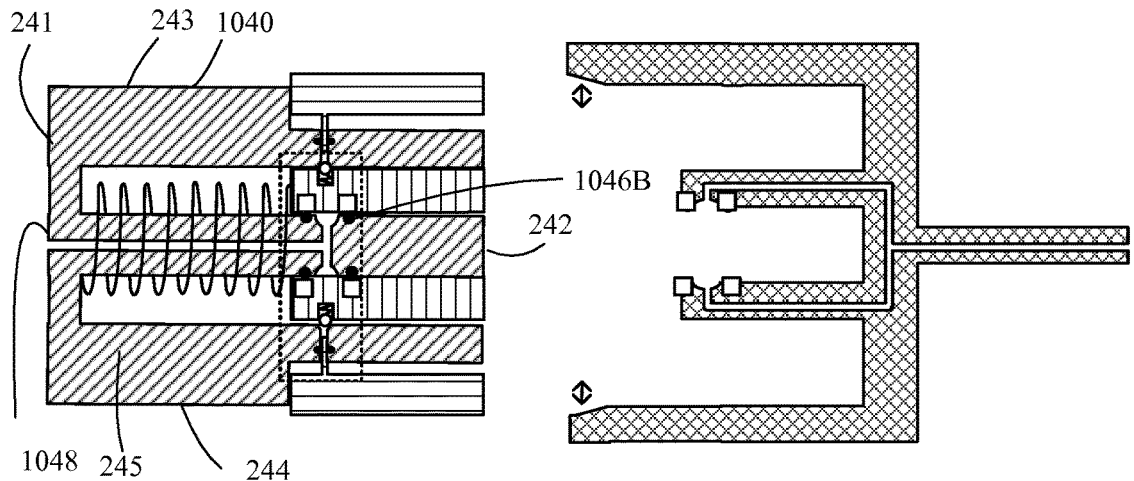
FIG. 10E illustrates the delivery system of FIG. 10A in an unconnected configuration.
Figure 10F:
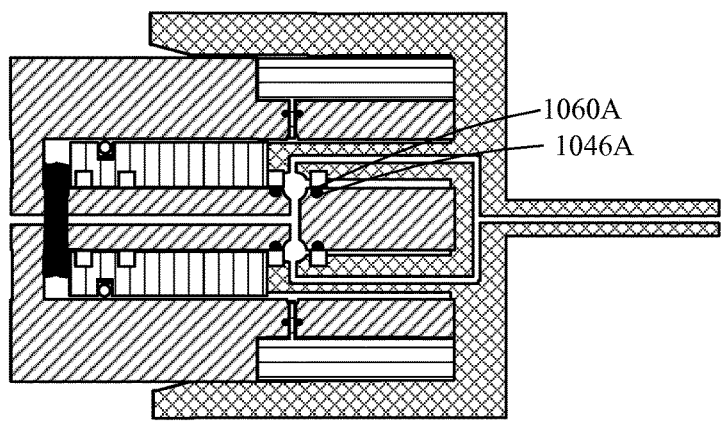
FIG. 10F illustrates the delivery system of FIG. 10A in an connected configuration.
Figure 10G:
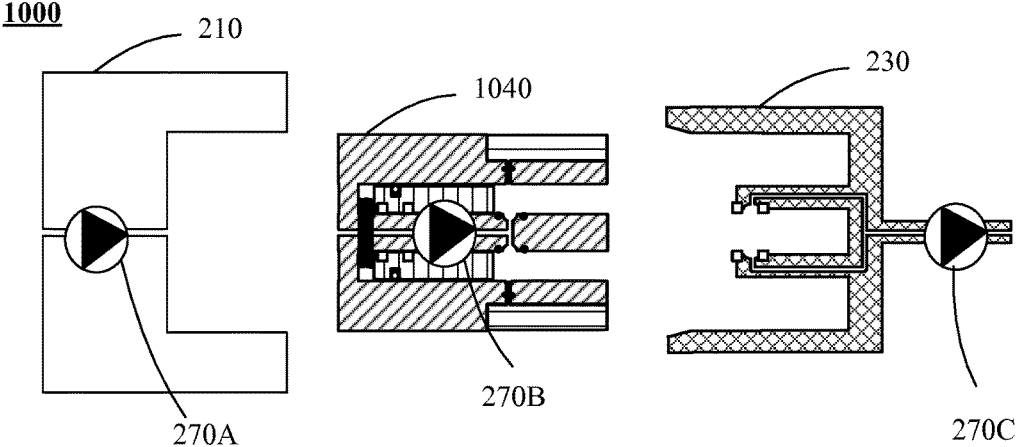
FIG. 10G illustrates the delivery system of FIG. 10 in an assembly state with a drug delivery device and a flow conducting device. All components flow communication unit, drug delivery device and flow conducting device can be provided with a unidirectional valve.
Figure 11A:
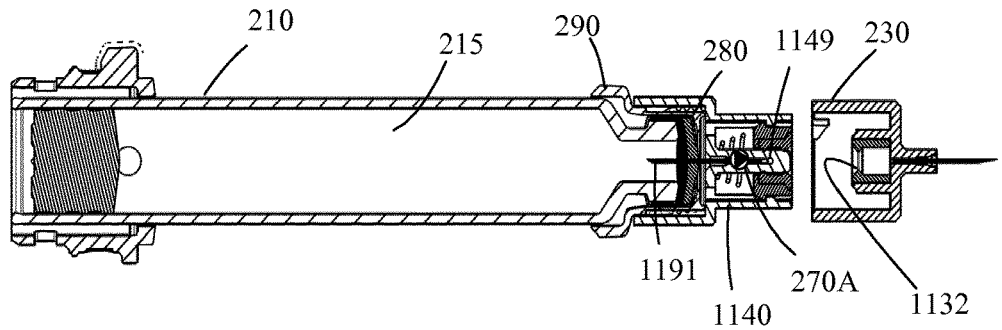
FIG. 11A shows in cross-section an embodiment of a drug delivery system according to the present disclosure, wherein the flow communication unit is connected with the drug delivery device. The cross-section is parallel with a longitudinal axis between two channel outlets. The figure further illustrates the flow conducting device.
Figure 11B:
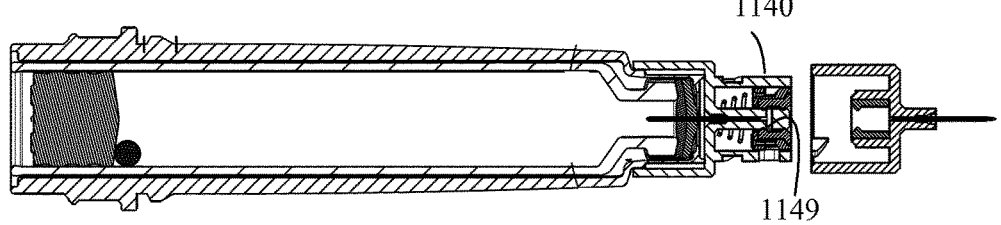
FIG. 11B shows in cross-section an embodiment of a drug delivery system according to the present disclosure, wherein the flow communication unit is connected with the drug delivery device. The cross-section is parallel with a radial axis of a channel outlet. The figure further illustrates the flow conducting device.
Figure 11C:
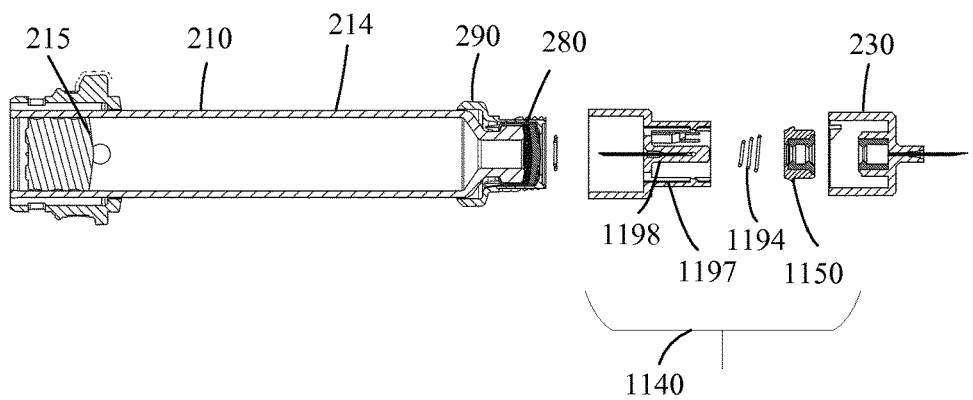
FIG. 11C shows an exploded view of the drug delivery system of FIG. 11A.
Figure 11D:
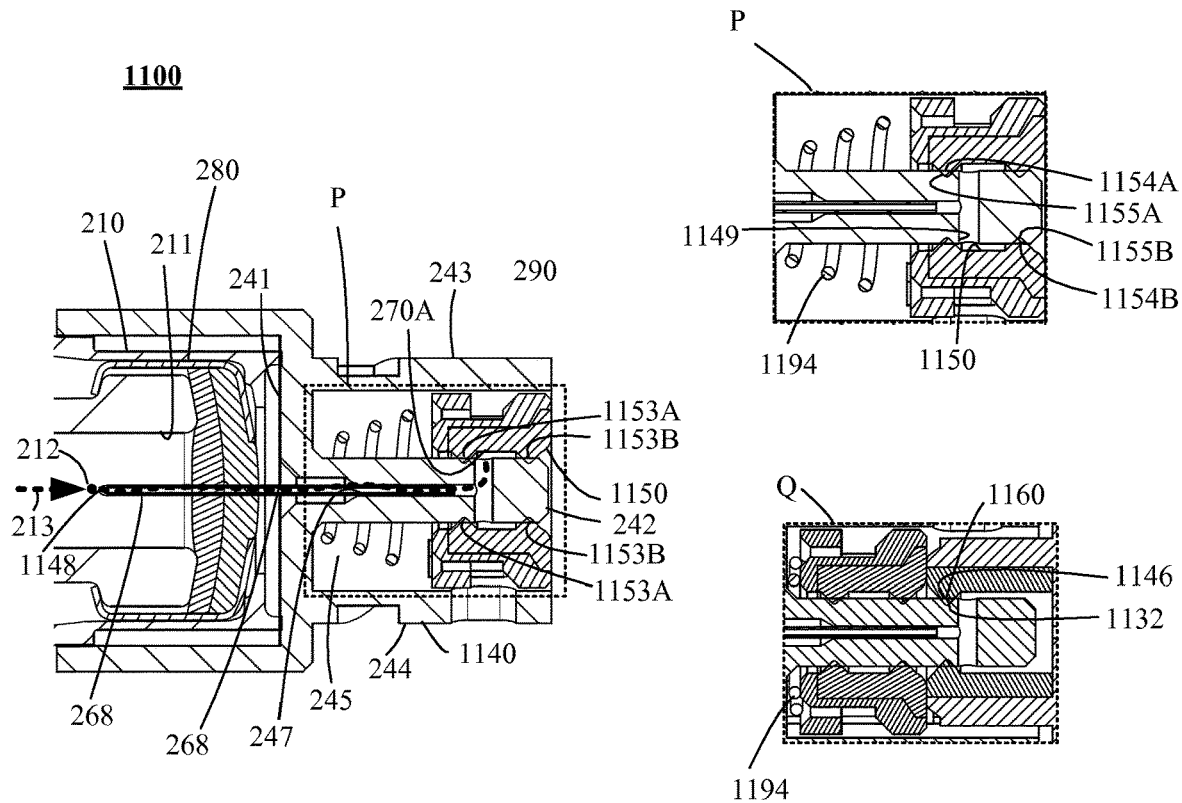
FIG. 11D left panel shows a close-up of the drug delivery system of FIG. 11A without the flow conducting device, and the right panel shows details of the left panel.
Figure 11E:
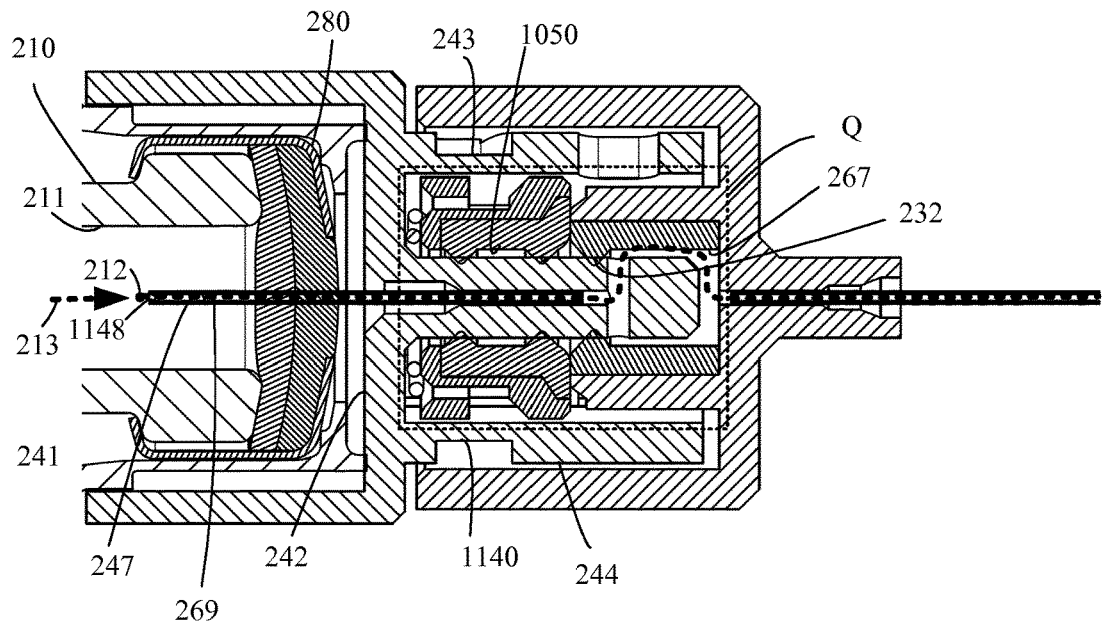
FIG. 11E shows a close-up of the drug delivery system of FIG. 11A.
Figure 12A:
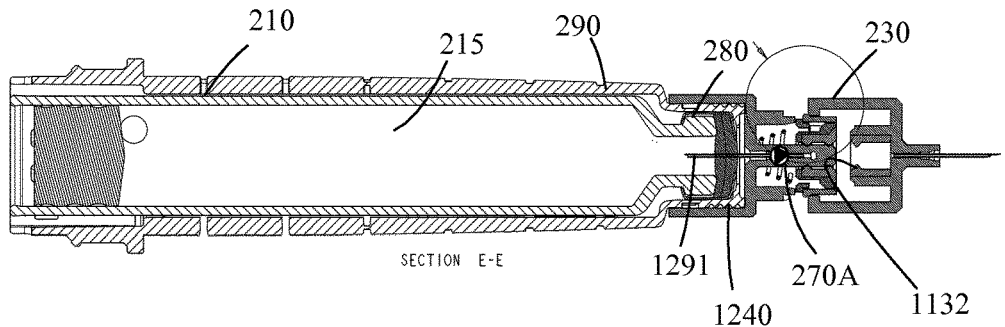
FIG. 12A shows in cross-section an embodiment of a drug delivery system according to the present disclosure, wherein the flow communication unit is connected with the drug delivery device. The cross-section is parallel with a radial axis of a channel outlet. The figure further illustrates the flow conducting device.
Figure 12B:
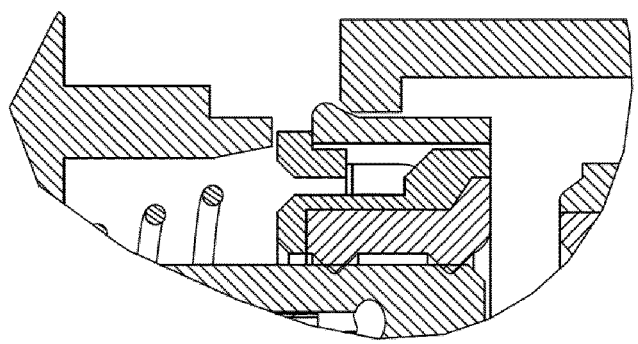
FIG. 12B show details of the drug delivery system of FIG. 12A, the details are marked with a circle.
Figure 12C:
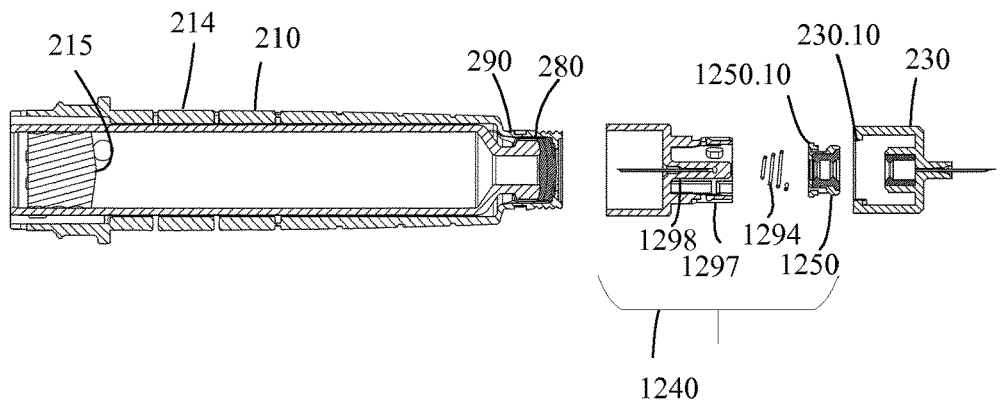
FIG. 12C shows an exploded view of the drug delivery system of FIG. 12A.
Figure 12D:
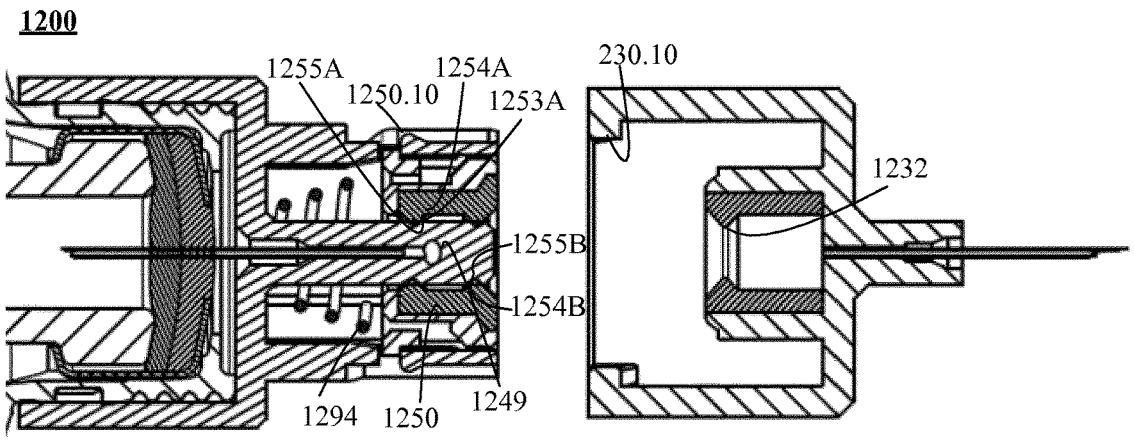
FIG. 12D shows a close-up of the drug delivery system of FIG. 12A.
Figure 12E:
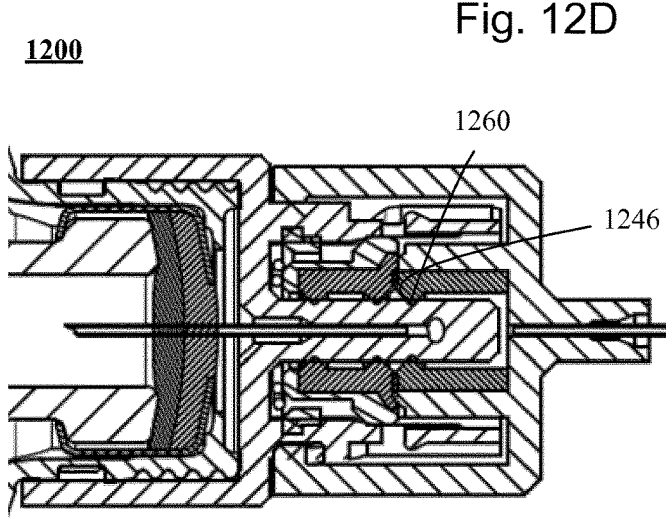
FIG. 12E shows a close-up of the drug delivery system of FIG. 12A, and connected with the flow conducting device.
Figure 12F:
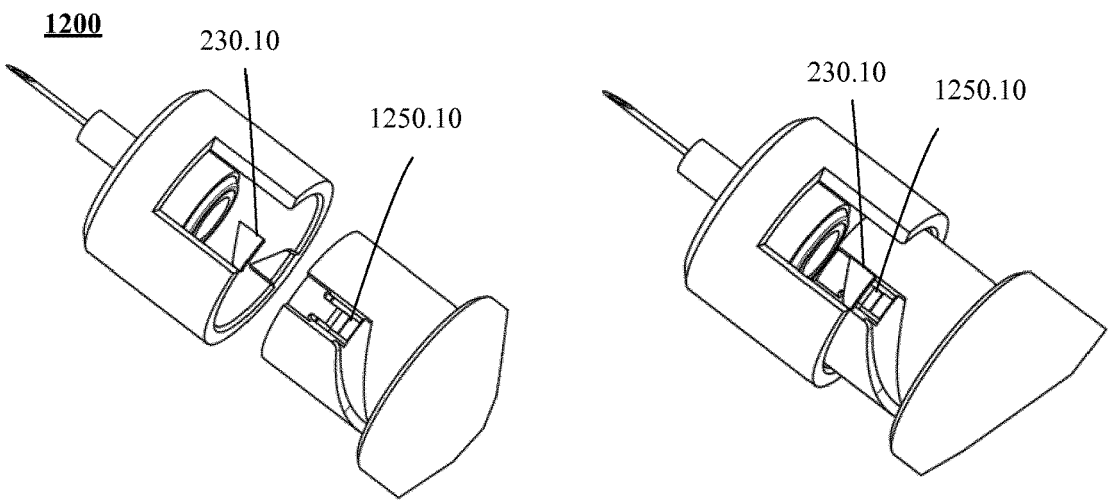
FIG. 12F left panel shows a perspective view of drug delivery system of FIG. 12A before connection with the flow conducting device, and the right panel shows a perspective view of drug delivery system of FIG. 12A during connection with the flow conducting device, and just before the outlet barrier lock is released.

The drug delivery device further comprises a pressure mechanism 214, 215 adapted to enable the application of a pressure on the liquid drug in the reservoir. As the primary purpose of FIGS. 2A, 3A and 4A is to illustrate the assembly state before assembly and common features, the pressure mechanism is only indicated on the figures as a dashed rectangle 214, 215. However, as an example the pressure mechanism may be embodied as a compressible reservoir comprising a cylinder 214 and a piston 215, as illustrated on FIG. 5A. By controlling the pressure mechanism the reservoir can be (i) in a pressurized state, wherein the pressure mechanism pressurizes the liquid drug, and (ii) an unpressurized state. The unpressurized state defines a state, wherein the pressure mechanism does not pressurize the liquid drug, and wherein the pressure of the drug is the same as the pressure outside the reservoir, i.e., the atmospheric pressure or the pressure of the surroundings. In both states the pressure mechanism prevents backflow into the reservoir, as the pressure in the reservoir is the same or above the pressure in the surroundings. Therefore, in order to prevent backflow the injection device can be operated in the pressurized state and the unpressurized state as described above. Alternatively, the backflow can be prevented by arranging a unidirectional valve in the injection device, the flow communication unit or the flow conducting device.

Figure 2C:
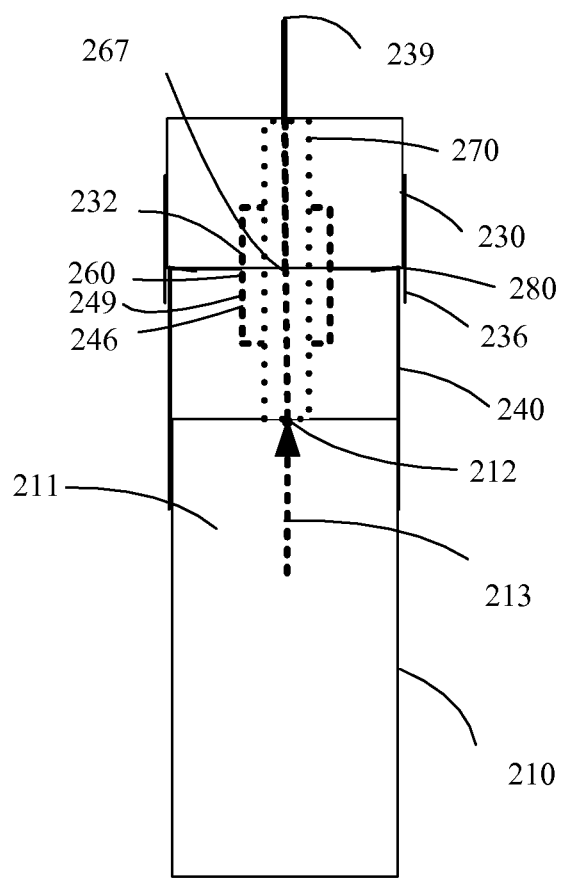
Figure 4C:
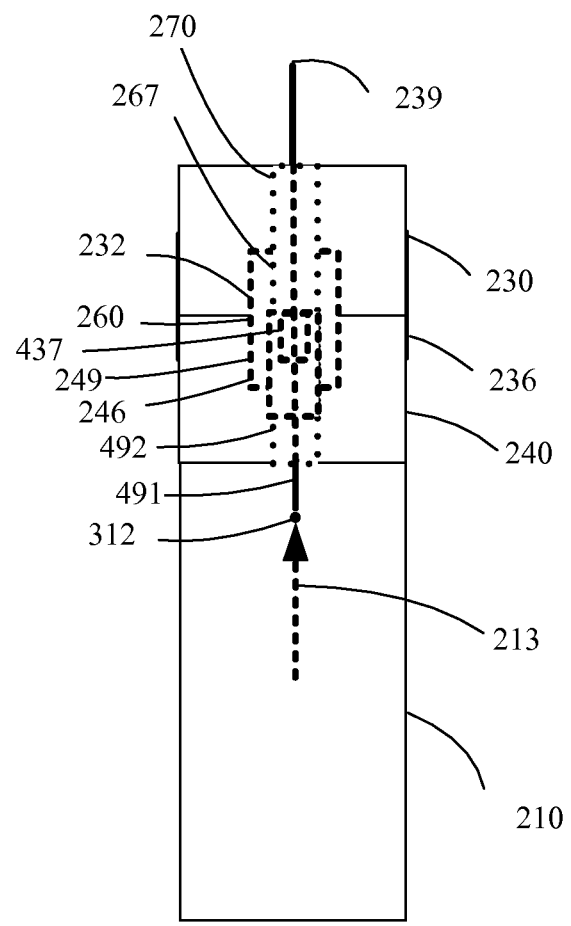

The drug delivery device further comprises a reservoir outlet 212 for drug flowing from the reservoir. The outlet is indicated on FIGS. 2A, 2C, 3C and 4C as a solid dot 212, 312. The dashed arrow 213 indicates the direction of flow out of the reservoir. The actual location or arrangement of the outlets 212, 312 depend on the interface with the flow communication unit, and how fluid communication is to be established. FIGS. 2A and 2C illustrate an embodiment wherein the flow communication unit functions as a closure and wherein the reservoir of the drug delivery device is open before assembly (FIG. 2A) and closed after assembly (FIG. 2C). Upon assembly, the flow communication unit is connected to the drug delivery device and the reservoir via a cap 280 (for example a metal cap), and fluid communication is established in the interface. Thus the reservoir outlet is also provided on the interface. This is different from the embodiment illustrated in 3A and 4A, wherein the reservoir of the flow conducting device may be covered and sealed by a membrane (septum), and wherein the flow communication unit does not function as a primary closure. In these embodiments, the flow communication unit comprises a piercing needle 391, 491 for piercing the membrane sealing the reservoir, and thereby establishing fluid communication. For these embodiments the outlet is arranged internally in the reservoir and not on the interface. The piercing needle 391 illustrated on FIG. 3 is fixedly mounted, wherein the piercing needle 491 illustrated on FIG. 4 is configurable between a retracted position (FIGS. 4A and 4B) and an extended configuration (FIG. 4C), and wherein a needle actuator 437 can change the piercing needle between the two configurations.

The flow communication unit comprises an inlet surface 241 for interfacing the drug delivery device 210, and the inlet surface is indicated on FIGS. 2A, 3A and 4A. FIGS. 2A and 2B schematically illustrate an embodiment of assembly states before assembly and after assembly, respectively, wherein the flow communication unit is assembled with the drug delivery device via a cap 280. Thereby, the flow communication unit interfaces the drug delivery device. Alternatively the cap could be substituted with an adapter top or code top, which also connects the flow communication unit to the drug delivery device, but further comprises a connector to connect with the flow conducting device. FIGS. 3A, 4A schematically illustrate the assembly state before assembly. FIGS. 3B and 4B schematically illustrate the assembly state after assembly, wherein the flow communication unit is connected with the drug delivery device using connector 345. The connector 345 of the flow communication unit is adapted to cooperate with a corresponding connector on the drug delivery device. The connector on the drug delivery device is not shown on the figure. Connector 345 may be a tread or bayonet connector.

In such an embodiment, a drug delivery system is modified by connecting a flow communication unit between the needle unit and the drug delivery device. This enables production of the same device for use both with and without preservatives in the drug. In products where preservatives can be added without drawbacks, the flow communication unit can simply be omitted.

The outlet surface can be changed between a connected and an unconnected configuration. The connected configuration is illustrated in FIGS. 2C, 3C and 4C and the unconnected configuration is illustrated in FIGS. 2A, 2B, 3A, 3B, 4A and 4B. The connected configuration is defined as the assumed configuration of the outlet surface, upon connection with the flow conducting device. In the connected configuration, the outlet surface allows connection between the flow communication unit and the flow conducting device, and the outlet surface is adapted for interfacing the flow conducting device 230. FIG. 2C illustrates schematically the flow communication unit connected to the flow conducing device via connectors 236 on the flow conducting device, and corresponding connectors on the flow communication unit or drug delivery device, which are not shown on the figure. The connector 236 may be a thread or bayonet connector. Thus the outlet surface allows connection, by not obstructing or hindering contact between the connectors, which is achieved by the outlet surface being adapted to interface the inlet surface of the flow conducting device. Therefore, the shape or form of the outlet surface, in the connected configuration, can be observed in the assembly state, wherein the flow conducting device is connected to the flow conducting device. The flow communication unit can also be observed in the connected configuration by manipulating the outer surface in a way resembling the manipulation of a connected flow conducting device. For some embodiments, the shape of the outlet surface in the connected configuration is close to the shape in the unconnected configuration, and, for other embodiments, the difference in shape is clearly visible, i.e., the shape is clearly modified upon connection. This aspect will be discussed later. In the unconnected configuration, the outlet surface is adapted for reducing the entrance of contaminations into the interior space 245 of the flow communication unit. This particular adaptation is not shown on FIGS. 2 to 4, but could be embodied as a barrier covering the channel outlet, as will be explained in details later. The unconnected configuration of the outlet surface is defined as the actual configuration, when the flow communication unit and the flow conducting device are not connected, which also includes the actual configuration in response to disconnecting the flow communication unit from the flow conducting device. The shape of the outlet surface in the unconnected configuration can thus be observed when the flow communication unit and the flow conducting device are not connected. The shape of the outlet surface in the unconnected configuration can be readily inspected, whereas the shape in the connected configuration can be estimated or imagined by comparing the shape of the inlet surface of the flow conducting device, and by considering how the inlet surface may interact with the outlet surface upon connection. A direct way of observing the shape of the outlet surface in the connected configuration will be to connect the flow communication unit with a transparent flow conducting device. Thereby the outlet surface can be inspected through the flow conducting device.

The flow communication unit further comprises intermediate surfaces 243, 244 extending between the inlet surface and the outlet surface. The inlet surface, the outlet surface and the intermediate surfaces define an outer surface and confine an interior space 245 of the flow communication unit, when the outlet surface is in the connected configuration and when it is in the unconnected configuration.

The flow communication unit further comprises an outlet sealing member 246, which is indicated with a dashed rectangle in FIGS. 2C, 3C and 4C, which indicates that this is only an approximate position of the features. The outlet sealing member provides a portion of the outlet surface, for the outlet surface being in the connected configuration, and as the outlet surface can change configuration this allows some variation in the position of the outlet sealing member, which is better illustrated in the FIGS. 5 to 12, and which will be explained later.

The outlet sealing member provides a portion of the outlet surface 242, for the outlet surface being in the connected configuration. That is to say, the outlet sealing member can be identified on the outlet surface, when the flow communication unit is connected to the flow conducting unit, or where the outlet surface has, by other means, has been manipulated into the connected configuration.

The outlet sealing member 246 is adapted for contacting the flow conducting device to establish a fluid tight channel seal 260, and can thereby provide a fluid tight contact with the flow conducting device, which allows a leakage free communication between the flow communication unit and the flow conducting device. The channel seal 260 is also indicated by the dashed rectangle as the position may vary depending on the exact embodiment. This aspect will be described in further details with reference to FIGS. 5-12.

The flow communication unit further comprises a first flow channel 247 comprising a channel inlet 248, 348, 448 adapted for providing flow communication with the drug delivery device, and a channel outlet 249 adapted for providing flow communication with the flow conducting device. The channel outlet 249 is indicated with a dashed rectangle in FIGS. 2C, 3C and 4C, which indicates that this is only an approximate position of the features.

The flow communication unit further comprises a first outlet valve member, which is not illustrated on FIGS. 2-4, but this aspect will be described in further details with reference to FIGS. 5-12.

The flow communication unit further comprises an outlet barrier 250 comprising a second outlet valve member adapted to cooperate with the first outlet valve member. The outlet barrier 250 provides a portion of the outlet surface 242, and the barrier 250 is indicated as a dashed rectangle on FIGS. 2-4, as the position can vary. The outlet barrier is configured for being in: (i) a closed configuration, and (ii) a flow configuration.

When the outlet barrier is in the closed configuration, this implies that the outlet surface is in the unconnected configuration, and that the second outlet valve member is adapted to cooperate with the first outlet valve member to provide an outlet barrier seal 253 (indicated as dashed rectangle on FIG. 2-4). Furthermore, the outlet barrier seal is adapted to reduce the entrance of contaminations through the channel outlet and into the first channel.

When the outlet barrier is in the flow configuration, this implies the outlet surface is in the connected configuration, and that the second outlet valve member is adapted to cooperate with the first outlet valve member to allow a drug contained in the first channel 247 to flow downstream from the channel inlet and out of the channel outlet 249, in response to the pressure in the first channel 247 being above a first threshold.

In addition to the adaptations of the outlet surface, the flow communication unit is also adapted for being in: (i) an unconnected configuration and (ii) a connected configuration.

The unconnected configuration of the flow communication unit can be provided, in response to disconnecting the flow communication unit from the flow conducting device, whereby the outlet surface will be in the unconnected configuration, and the outlet barrier is in the closed configuration. When the communication unit is in the unconnected configuration, the outlet surface reduces the entrance of contaminations to the internal volume, and the outlet barrier seal reduces in particular contaminations into the channel outlet and further the first channel and the reservoir.

The connected configuration of the flow communication unit can be provided, in response to connecting the flow communication unit to the flow conducting device 230, whereby the outlet surface will be in the connected configuration, and the outlet barrier is in the flow configuration. In this configuration, the outlet sealing member 246 is arranged to be able to contact the flow conducting device to provide the channel seal 260 downstream to the channel outlet 249 of the first flow channel. The flow communication unit is thereby adapted to allow flow communication between the channel outlet 249 and the flow conducting device, and the channel outlet 249 is arranged at the outlet surface 242 of the flow communication unit. As the outlet sealing member provides a portion of the outlet surface, and as this portion is arranged downstream to the channel outlet arranged on the outlet surface, the flow communication unit is adapted to be connected with the flow conducting device, without entering the internal volume of the flow communication unit.

An example of a flow conducting device entering the internal volume of a drug delivery device is a conventional pen needle with a proximal piercing needle, which is adapted to penetrate a membrane covering the outlet of a drug reservoir.

By changing the flow communication to the connected configuration, a combined flow channel 267 can be provided between the drug delivery device 210, the first flow channel 247 and the flow conducting device 230 with the channel seal arranged downstream to the channel outlet, in response to the channel inlet being arranged in flow communication with the drug delivery device and response to the flow communication unit 240 being connected to the flow conducting device.

Hereby the flow communication unit 240 is adapted to enable the extended use of the multi-use drug delivery device without destruction or removal of a closure of the multiple-dose drug delivery device, and whereby the flow communication unit is adapted to inhibit microbial entrance in the multi-use drug delivery device during the extended use.

Flow Conducting Device

The flow conducting device 230 for conducting drug from the flow communication unit comprises a first connector 236 adapted for connecting the flow conducting device 230 to the flow communication unit 240, and an inlet surface 231 for interfacing and contacting the outlet surface 242 of the flow communication unit 240. The inlet surface 231 provides an outer surface of the flow conducting device 230.

The flow conducting device further comprises an inlet sealing portion 232 providing a portion of the inlet surface 231, and adapted for contacting the outlet sealing portion 246 of the flow communication unit 240. The inlet sealing portion is adapted to provide a fluid tight seal in the interface between the flow conducting device and the flow communication unit.

The flow conducting device further comprises a second channel 237 for conducting fluid having a channel inlet 238 positioned at the inlet surface 231, and a channel outlet 239.

The flow conducting device may be in the form of a pen needle comprising a hub and a needle cannula, or in the form of an infusion set comprising a hub and a catheter.

Drug Delivery System

The drug delivery system is adapted to be assembled in a connected configuration, wherein the flow communication unit is in the connected configuration, and connected to the flow conducting device 230. The outlet sealing portion 246 and the inlet sealing portion 232 are thereby brought in contact to provide the fluid tight channel seal 260 in the interface between the flow communication unit and the flow conducting device. The channel inlet 248 of the first channel 247 is arranged in fluid communication with the reservoir outlet 212, wherein the channel outlet 249 of the first channel 247 is arranged in fluid communication with the channel inlet 238 of the second channel 237, whereby a combined flow channel 267 is provided between the reservoir, the first channel and the second channel.

The channel seal 260 surrounds the combined flow channel and provides a portion of the combined flow channel, wherein the combined flow channel defines a well determined volume, whereby a well determined amount of drug can be delivered through the combined flow channel and to a subject. The combined flow channel comprises an inner surface adapted to be in direct contact with drug flowing in the combined flow channel, and the channel seal is also adapted to be in direct contact with the drug flowing in the combined flow channel.

To restrict a reverse flow from the flow conducting device towards the reservoir, when the flow communication unit is in the connected configuration, and in response to the pressure in the second channel being larger than the pressure in the first channel, the system may further comprise a unidirectional valve 270 positioned along the combined flow channel. The unidirectional valve is adapted to allow a flow from the reservoir to the flow conducting device in response to the reservoir 213 being in the pressurized state, whereby the pressure propagates from the reservoir to the first channel and to the second channel. Alternatively, reverse flow or back flow can be prevented by controlling the pressure mechanism. The reservoir can be (i) in a pressurized state, wherein the pressure mechanism pressurizes the liquid drug, and (ii) an unpressurized state. The unpressurized state defines a state, wherein the pressure mechanism does not pressurize the liquid drug, and wherein the pressure of the drug is the same as the pressure outside the reservoir, i.e., the atmospheric pressure or the pressure of the surroundings. In both states the pressure mechanism prevents backflow into the reservoir, as the pressure in the reservoir is the same or above the pressure in the surroundings. Therefore, in order to prevent backflow the injection device can be operated in the pressurized state and the unpressurized state as described above.

The system may further comprise a shell, wherein the shell is adapted for: (i) covering a portion of the outer surface of the flow communication module, (ii) retaining the flow communication module in contact with the drug delivery device. The shell may be in the form of a cap, adapter top or code top.

Embodiments of FIGS. 5-12

Embodiments of FIGS. 5-12 show a flow communication unit 540, 640, 740, 840, 940, 1040, 1140, 1240 for establishing flow communication from a multi-use drug delivery device 210 adapted for extended use, to a flow conducting device 230. The drug delivery device 210 comprises a reservoir with multiple doses of a liquid drug formulation. The drug formulation would allow microbial growth upon accidental introduction of microorganisms into the reservoir during extended use, or upon introduction of microorganisms for test purposes. The reservoir is adapted to pressurize the liquid drug formulation, and the flow conducting device 230 is adapted for conducting the drug to the subcutaneous tissue of a subject.

The flow communication unit comprises an inlet surface 241 for interfacing a drug delivery device 210, and an outlet surface 242. The outlet surface is configured for being in a connected and an unconnected configuration. In the connected configuration, the outlet surface allows the flow communication unit and the flow conducting device to be connected. The outlet surface is adapted for interfacing the flow conducting device 230, and thereby ensures that there is no physical hindrance in mating the two surfaces. In the unconnected configuration, the outlet surface allows the flow communication unit and the flow conducting device to be unconnected. The outlet surface is adapted for reducing the entrance of contaminations into the interior space 245 of the flow communication unit, and thereby ensures that the flow communication unit can be safely stored, either separately or as connected/integrated with a drug delivery device, without allowing entrance of contamination through the outlet surface.

The flow communication unit also comprises intermediate surfaces 243, 244 extending between the inlet surface and the outlet surface. The inlet surface, the outlet surface and the intermediate surfaces define an outer surface and confine an interior space 245 of the flow communication unit. The shape of the outer surface may be different depending on which of the two different configurations the outlet surface is configured in, in both configurations the outlet surface provides a portion of the outer surface.

The flow communication unit further comprises an outlet sealing member 546, 646, 746, 846, 946, 1046, 1146, 1246, which provides a portion of the outlet surface 242, when the outlet surface is the connected configuration. The outlet sealing member 546, 646, 746, 846, 946, 1046, 1146, 1246 is adapted for contacting the flow conducting device to establish a fluid tight channel seal 560, 660, 760, 860, 960, 1060, 1160, 1260. Therefore, the sealing member has to be provided on the outer surface. Otherwise, it would not be possible to contact another surface. The outlet sealing member is adapted to provide fluid tight contact with the flow conducting device.

The flow communication unit further comprises a first flow channel 247 comprising a channel inlet 348, 448, 548, 648, 748, 948, 1048, 1148, 1248 adapted for providing flow communication with the drug delivery device, and a channel outlet 549, 649, 749, 849, 949, 1049, 1149, 1249 adapted for providing flow communication with the flow conducting device.

The flow communication unit further comprises, a first outlet valve member 554, 654, 754, 854, 954, 1054, 1154, 1254, and an outlet barrier 550, 660, 760, 850, 950, 1050, 1150, 1250. The outlet barrier comprises a second outlet valve member 555, 655, 755, 855, 955, 1055, 1155, 1255 adapted to cooperate with the first outlet valve member 554, 654, 754, 854, 954, 1054, 1154, 1254. The outlet barrier 550, 650, 750, 850, 950, 1050, 1150, 1250 also provides a portion of the outlet surface 242. The outlet barrier provides a portion of the outer surface of the flow communication unit both in situations, when the outlet surface is in the connected and the unconnected configuration.

The outlet barrier is configured for being in a closed configuration and a flow configuration. The closed configuration is shown in FIGS. 5D, 6C, 7C, 8C, 9C, 10C, 11D and 12E, and the flow configuration is shown in FIGS. 5E, 6D, 7D, 8D, 9D, 10D, 11E and 12F.

In the closed configuration, the outlet barrier is closed, which is the normal configuration of the outlet barrier, when the flow communication unit is not manipulated, e.g., it is not manipulated into the flow configuration by the flow conducting device during connection. When the outlet barrier is in the closed configuration, the outlet surface is in the unconnected configuration, and the second outlet valve member 555, 655, 755, 855, 955, 1055, 1155, 1255 is adapted to cooperate with the first outlet valve member 554, 654, 754, 854, 954, 1054, 1154, 1254 to provide an outlet barrier seal 253, 553, 653, 753, 853, 953, 1053, 1153, 1253). In the closed configuration, the outlet barrier seal is adapted to reduce the entrance of contaminations through the channel outlet and into the first channel.

In the flow configuration, the outlet surface is in the connected configuration. The second outlet valve member 555, 655, 755, 855, 955, 1055, 1155, 1255 is adapted to cooperate with the first outlet valve member 554, 654, 754, 854, 954, 1054, 1154, 1254 to allow a drug contained in the first channel 247 to flow downstream from the channel inlet and out of the channel outlet 249, 549, 749, 849, 949, 1049, 1149, 1249, in response to the pressure in the first channel 247 being above a first threshold.

The flow communication unit is further adapted for being in an unconnected and a connected configuration. The closed configuration is shown in FIGS. 5D, 6C, 7C, 8C, 9C, 10C, 11D and 12E, and the flow configuration is shown in FIGS. 5E, 6D, 7D, 8D, 9D, 10D, 11E and 12F.

The unconnected configuration can be obtained in response to disconnecting the flow communication unit from the flow conducting device. The flow communication unit is also configured in the unconnected configuration prior to connecting the flow conducting device to the flow communication unit. For the flow communication unit being in the unconnected configuration, the outlet surface is in the unconnected configuration, and the outlet barrier is in the closed configuration.

The connected configuration can be obtained in response to connecting the flow communication unit to the flow conducting device 230, or simply when the unit is connected to the flow conducting device. In this configuration, the outlet surface is in the connected configuration, and the outlet barrier is in the flow configuration, wherein the outlet sealing member is arranged to be able to contact the flow conducting device to provide the channel seal downstream to the channel outlet 549, 649, 749, 849, 949, 1049, 1149 of the first flow channel. Thereby, the flow communication unit in the connected configuration, is adapted to allow flow communication between the channel outlet 549, 649, 746, 849, 949, 1049, 1149, 1249 and the flow conducting device, with the channel outlet 549, 649, 749, 849, 949, 1049, 1149, 1249 arranged at the outlet surface 242 of the flow communication unit.

The flow communication unit is adapted to provide a combined flow channel 267 between the drug delivery device 210, the first flow channel 247 and the flow conducting device 230 with the channel seal arranged downstream to the channel outlet, in response to the channel inlet being arranged in flow communication with the drug delivery device and the flow communication unit 540, 640, 740, 840, 940, 1040, 1140, 1240 being connected to the flow conducting device.

Hereby, the flow communication unit 540, 640, 740, 840, 940, 1040, 1140, 1240) is adapted to enable the extended use of the multi-use drug delivery device without destruction or removal of the flow communication unit or a closure of the multiple-dose drug delivery device. In this way, the flow communication unit is adapted to inhibit microbial entrance in the multi-use drug delivery device during the extended use.

Channel Outlet

In some embodiments of the flow communication unit according to the present disclosure, the outlet barrier 550, 650, 750, 850, 950 provides the channel outlet 549, 649, 749, 849, 949.

Outlet Sealing Member

In some embodiments of the flow communication unit according to the present disclosure, the outlet barrier 550, 650, 850, 950 provides the outlet sealing member 546, 646, 846, 946.

Unidirectional Valve

In some embodiments of the flow communication unit according to the present disclosure, the flow communication unit further comprises a unidirectional valve 270 arranged along the first channel 247. The valve is adapted for guiding the flow downstream and for inhibiting upstream flow towards the drug delivery device. Hereby a forced unidirectional flow contributes to the reduction of contaminations through the channel outlet and into the first channel.

Embodiments with Reference to FIGS. 3, 4, 11 and 12 —Proximal Piercing Needle In some embodiments of the flow communication unit according to the present disclosure, the flow communication unit further comprises a proximal piercing needle 391, 491, 1191, 1291 extending from the inlet surface in an extended configuration, wherein the proximal needle comprises a proximal open end providing the channel inlet 249.

In some embodiments of the flow communication unit according to the present disclosure, the flow communication unit further comprises a proximal piercing needle actuator 492 adapted to change the proximal piercing needle from a retracted configuration to the extended configuration, in response to connecting the flow communicating unit with the flow conducting device.

Embodiments with Reference to FIGS. 5, 6, 7, 8, and 9—Proximal Valve Member

In some embodiments of the flow communication unit according to the present disclosure, the flow communication unit further comprises a proximal valve member 598, 698, 798, 898, 998, adapted to allow a flow from the inlet towards the outlet and for preventing a reverse flow.

In some embodiments of the flow communication unit according to the present disclosure, the proximal valve member 598, 698, 798, 898, 998 provides a portion of the inlet surface 241 for interfacing the drug delivery device.

In some embodiments of the flow communication unit according to the present disclosure, the proximal valve member 598, 698, 798, 898, 998 provides a portion of the intermediate surfaces 243, 244 extending between the inlet surface 241 and the outlet surface 242.

In some embodiments of the flow communication unit according to the present disclosure, the portion of the intermediate surfaces 243, 244 is soft and provides a device sealing surface 598.1, 698.1, 798.1, 898.1, 998.1 to seal against the drug delivery device 210.

Embodiments with Reference to FIGS. 5, 6, 7, 8—Proximal Valve Member

In some embodiments of the flow communication unit according to the present disclosure, the proximal valve member provides the channel inlet 548, 648, 748, 848.

Embodiments with Reference to FIG. 5 —Proximal Support Member

In some embodiments of the flow communication unit according to the present disclosure, the flow communication unit further comprises a proximal support member 597 comprising a proximal end 597.9 and a proximal portion adapted 597.10 to support the proximal valve member 598.

In some embodiments of the flow communication unit according to the present disclosure, the proximal support member 597 is rigid, and the proximal portion of the proximal support member 597 comprises a surface portion defining a proximal valve seat 597.1 adapted to provide a proximal seat sealing surface 597.2. The proximal valve member 598 comprises a surface portion adapted to provide a proximal valve sealing surface 598.2, and a proximal fluid tight seal 597.3 is provided between the proximal valve sealing surface 598.2 and the proximal seat sealing surface 597.2.

In some embodiments of the flow communication unit according to the present disclosure, the proximal support member 597 is rigid and provides a proximal portion of the first channel 247.

In some embodiments of the flow communication unit according to the present disclosure, the proximal portion of the first channel 247 provided by the proximal support member extends from the proximal end 597.9 of the proximal support member 597. Doesn't it extend from the inlet?

In some embodiments of the flow communication unit according to the present disclosure, the proximal valve member 598 comprises a surface portion providing a portion of the inlet surface 241 for interfacing the drug delivery device 210. The proximal valve member 598 is flexible and can be changed from a normal configuration to a forced configuration, in response to a fluid pressure on the inlet surface 241.

In some embodiments of the flow communication unit according to the present disclosure, the flow communication unit 540 comprises a normally closed configuration, wherein the proximal valve member is in the normal configuration, and thereby provides the proximal fluid tight seal 597.3.

In some embodiments of the flow communication unit according to the present disclosure, the proximal support member 597 comprises an enlarged channel portion 597.4 adapted to accommodate an accommodative portion 598.3 of the proximal valve member, which comprises the proximal valve sealing surface 598.2. The flow communication unit 540 comprises an open configuration, wherein the enlarged channel portion 597.4 accommodates the accommodative portion of the proximal valve member, for the proximal valve member being in the forced configuration. In this configuration the proximal fluid tight seal 597.3 is not provided, and a flow can be guided through the valve.

In some embodiments of the flow communication unit according to the present disclosure, the proximal support member 597, 697 further comprises a support portion 597.5, 697.5 adapted to be supported by the drug delivery device 210, and thereby provide support for the flow communication unit in relation to the drug delivery device 210.

Embodiments with Reference to FIGS. 5 and 8

In some embodiments of the flow communication unit according to the present disclosure, a distal support member 593, 893 comprises a distal end and a distal portion adapted to support the outlet barrier 550, 850, and wherein the distal support member further comprises a barrier operating member 593.2, 893.2 adapted to cooperate with the outlet barrier in regulating the tightness of the outlet barrier seal 553, 853.

This can be obtained by the outlet barrier 550, 850 comprising an actuator portion 550.2, 850.2 providing the outlet sealing member 546, 846. The actuator portion is movably arranged between a first position and a second position relative to the barrier operating member 593.2, 893.2, and adapted to be configured in an unconnected and a connected configuration.

In the unconnected configuration, the outlet barrier is in the closed configuration, wherein the closed configuration of the outlet barrier further comprises the actuator portion 550.2, 850.2 being in the first position relative to the barrier operating member 593.2, 893.2, whereby the second outlet valve member 555, 855 is adapted to cooperate with the first outlet valve member 554, 854 to provide the outlet barrier seal 553, 853 adapted to allow a drug contained in the first channel to flow downstream from the channel inlet and out of the channel outlet 549, 849, in response to the pressure in the first channel 247 being above a second threshold. The second threshold defines the tightness of the outlet barrier seal 553, 853 in the unconnected configuration and is larger than the first threshold.

In the connected configuration, the outlet barrier is in the flow configuration, wherein the flow configuration of the outlet barrier further comprises the actuator portion 550.2, 850.2 is in the second position relative to the barrier operating member 593.2, 893.2, whereby the second outlet valve member 555, 855 is adapted to cooperate with the first outlet valve member 554, 854 to provide the outlet barrier seal 553, 853 adapted allow a drug contained in the first channel to flow downstream from the channel inlet and out of the channel outlet 549, 849, in response to the pressure in the first channel 247 being above the first threshold, wherein the first threshold defines the tightness of the outlet barrier seal in the connected configuration.

In some embodiments of the flow communication unit according to the present disclosure, the actuator portion is adapted to be manipulated from the first position to the second position, by the flow conducting device upon connection.

In some embodiments of the flow communication unit according to the present disclosure, the flow communication unit is further adapted for being in: (i) the unconnected configuration, wherein the barrier seal 553, 853 is defined by a second threshold, and (ii) the connected configuration, wherein the barrier seal 553, 853 is defined by the first threshold.

Embodiments with Reference to FIG. 5—Intermediate Valve Member

In some embodiments of the flow communication unit according to the present disclosure, the flow communication unit further comprises an intermediate valve member 594.

In some embodiments of the flow communication unit according to the present disclosure, wherein the proximal support member 597 comprises a distal end 597.11 and a distal portion 597.12 adapted to support the intermediate valve member 594.

In some embodiments of the flow communication unit according to the present disclosure, the proximal support member 597 is rigid, and the distal portion 597.12 of the proximal support member 597 comprises a surface portion defining an intermediate valve seat 597.6 adapted to provide an intermediate seat sealing surface 597.7. The intermediate valve member 594 comprises a surface portion adapted to provide an intermediate valve sealing surface 594.1. Hereby, an intermediate fluid tight seal 597.8 can be provided between the intermediate valve sealing surface 594.1 and the intermediate seat sealing surface 597.7.

In some embodiments of the flow communication unit according to the present disclosure, the proximal portion of the first channel 247 provided by the proximal support member extends from the proximal end 597.9 to the distal end 597.11. Doesn't it extend from the inlet?

In some embodiments of the flow communication unit according to the present disclosure, the intermediate valve member 594 comprises a proximal surface portion for interfacing the proximal support member 597, and wherein the intermediate valve member 594 is flexible and can be changed from a normal configuration to a forced configuration, in response to a fluid pressure on the proximal surface.

In some embodiments of the flow communication unit according to the present disclosure, the normally closed configuration of the flow communication unit 540 further comprises, the intermediate valve member being in the normal configuration and provides the intermediate fluid tight seal 597.8.

Embodiments with Reference to FIG. 5—Distal Support Member

In some embodiments of the flow communication unit according to the present disclosure, the flow communication unit further comprises a distal support member 593.

In some embodiments of the flow communication unit according to the present disclosure, the distal support member 593 is rigid and provides a distal portion of the first channel 247.

In some embodiments of the flow communication unit according to the present disclosure, the distal support member 593 comprises an enlarged channel portion 593.1 adapted to receive a portion of a flexible portion 594.2 of the intermediate valve member 594, wherein the flexible portion 594.2 of the intermediate valve member 594 comprises the intermediate valve sealing surface 594.1. The open configuration of the flow communication unit 540 further comprises the enlarged channel portion 593.1 receiving the portion of the flexible portion of the intermediate valve member in the forced configuration, wherein the intermediate fluid tight seal 597.3 is not provided.

In some embodiments of the flow communication unit according to the present disclosure, the distal support member 593 further comprises a support portion adapted to be supported by the proximal support member, and thereby provide stability to the flow communication unit.

In some embodiments of the flow communication unit according to the present disclosure, the distal support member 593 and the proximal support member 597 are adapted to clamp a portion of the intermediate valve member 594. Hereby, the clamped portion is fixed and the unclamped portion is adapted to be moved between the normal and the forced configuration.

In some embodiments of the flow communication unit according to the present disclosure, the distal support member 593 further comprises a support portion adapted to be supported by the drug delivery device 210, and thereby provide support for the flow communication unit in relation to the drug delivery device 210.

Embodiments with Reference to FIG. 5—Outlet Barrier

In some embodiments of the flow communication unit according to the present disclosure, the distal support member 593 comprises a distal end and a distal portion adapted to support the outlet barrier 550.

In some embodiments of the flow communication unit according to the present disclosure, the distal support member 593 is rigid and the distal portion of the distal support member 593 comprises a surface portion defining the first outlet valve member 554 adapted to provide a seat sealing surface, wherein the outlet barrier 550 comprises a surface portion defining the second outlet valve member 555 adapted to provide a valve sealing surface, and wherein the outlet barrier seal 553 can be provided between the valve sealing surface and the seat sealing surface.

In some embodiments of the flow communication unit according to the present disclosure, the outlet barrier 550 comprises a proximal surface portion for interfacing the distal support member 593, and wherein the outlet barrier 550 is flexible and can be changed from a normal configuration to a forced configuration, in response to the pressure in the first channel 247 and on the proximal surface portion being above the first threshold.

In some embodiments of the flow communication unit according to the present disclosure, the normally closed configuration of the flow communication unit 540 further comprises, the outlet barrier being in the normal configuration and provides the outlet barrier seal 553.

In some embodiments of the flow communication unit according to the present disclosure, the flow conducting device 230 comprises an enlarged channel inlet 238 adapted to receive a portion of a flexible portion 550.1 of the outlet barrier 550, wherein the flexible portion 550.1 of the outlet barrier 550 comprises the valve sealing surface. The open configuration of the flow communication unit further comprises the enlarged channel inlet 238 receiving the portion of the flexible portion 550.1 of the outlet barrier in the forced configuration, wherein the outlet barrier seal 553 is not provided.

In some embodiments of the flow communication unit according to the present disclosure, the outlet barrier 550 provides the outlet sealing member 546.

In some embodiments of the flow communication unit according to the present disclosure, the distal support member 593 comprises a distal end and a distal portion adapted to support the outlet barrier 550, wherein
  the distal support member further comprises a spacing member 593.2 adapted to separate the supported outlet barrier from the distal support member, whereby a space is provided between the distal support member and the outlet barrier, and
  wherein the outlet barrier 550 comprises an actuator portion 550.2 providing the outlet sealing member 546 and movably arranged between a first position and a second position relative to the spacing member 593.2, and adapted to be configured in an:
  (i) unconnected configuration, wherein the outlet barrier is in the closed configuration, wherein the closed configuration of the outlet barrier further comprises the actuator portion 550.2 being in the first position relative to the spacing member 593.2, whereby the second outlet valve member 555 is adapted to cooperate with the first outlet valve member 554 to provide the outlet barrier seal 553 adapted to allow a drug contained in the first channel to flow downstream from the channel inlet and out of the channel outlet 549, in response to the pressure in the first channel 247 being above a second threshold, wherein the second threshold defines the tightness of the outlet barrier seal 553 and is larger than the first threshold,
  (ii) a connected configuration, wherein the outlet barrier is in the flow configuration, wherein the flow configuration of the outlet barrier further comprises the actuator portion 550.2 is in the second position relative to the spacing member 593.2, whereby the second outlet valve member 555 is adapted to cooperate with the first outlet valve member 554 to provide the outlet barrier seal 553 adapted allow a drug contained in the first channel to flow downstream from the channel inlet and out of the channel outlet 549, in response to the pressure in the first channel 247 being above the first threshold, wherein the first threshold defines the tightness of the outlet barrier seal.

Hereby, the actuator portion, which also provides the outlet sealing member 546, is adapted to be manipulated from the first position to the second position, by the flow conducting device upon connection.

Hereby is provided a flow communication unit, wherein the flow communication unit is further adapted for being in:
  (i) the unconnected configuration, wherein the tightness of the barrier seal 553 is defined by a second threshold, and
  (ii) the connected configuration, wherein the tightness of the barrier seal 553 is defined by the first threshold.

Hereby, is obtained a flow communication unit, which enables extended use of a multi-dose injection device comprising a drug which does not in itself prevent microbial growth, and the extended use is enabled, as the channel seal is arranged downstream to the outlet, and as the outlet is positioned on an outer surface of the device. In other words, the flow communication unit eliminates the problem arising, when a portion of a potentially contaminated flow conducting device, e.g., pen needles entering, crosses the outer surface of a drug delivery device. If this happens there is a risk of contaminating of the internal parts of the drug delivery device. Furthermore, when portions of a flow conducting device penetrates an outer surface, wherein a channel seal is created between the penetrating conducting device and the outer surface, e.g., a septum, a vacuum is created in the drug delivery device, when the flow conducting device is detached from the drug delivery device, and body fluids may consequently be withdrawn into drug delivery device. This effect is also eliminated or minimized, when the channel seal is created on the outer surface of the drug delivery device, i.e., no portions of the flow conducting device is crossing the outer surface.

Embodiments with Reference to FIG. 6 —Support Member

In some embodiments of the flow communication unit according to the present disclosure, the flow communication unit further comprises a support member 697 comprising a proximal end 697.9 and a proximal portion adapted 697.10 to support the proximal valve member 698.

In some embodiments of the flow communication unit according to the present disclosure, the support member 697 is rigid, and the proximal valve member 698 is a self-contained valve 698 comprising a first valve member comprising a surface portion adapted to provide a first proximal valve sealing surface. The proximal valve member further comprises a second valve member comprising a surface portion adapted to provide a second proximal valve sealing surface. The two valve members are adapted to provide a proximal fluid tight seal 698.2 between the first and the second proximal valve sealing surface.

In some embodiments of the flow communication unit according to the present disclosure, the support member 697 is rigid, and the proximal portion of the support member 697 comprises a proximal valve housing 697.1 adapted to accommodate an accommodative portion 698.3 of the self-contained valve 698.

In some embodiments of the flow communication unit according to the present disclosure, the support member 697 provides a portion of the first channel 247.

In some embodiments of the flow communication unit according to the present disclosure, the portion of the first channel 247 provided by the support member 697, extends from the proximal end 697.9 of the support member 697.

In some embodiments of the flow communication unit according to the present disclosure, the self-contained valve 698 comprises a surface portion providing a portion of the inlet surface 241 for interfacing the drug delivery device 210, and the self-contained valve 698 is flexible and can be changed from a normal configuration to a forced configuration, in response to a fluid pressure on the inlet surface 241.

In some embodiments of the flow communication unit according to the present disclosure, the flow communication unit 640 comprises a normally closed configuration, wherein the self-contained valve is in the normal configuration, and thereby provides the proximal fluid tight seal 698.2.

In some embodiments of the flow communication unit according to the present disclosure, the self-contained valve is in the forced configuration, and the proximal fluid tight seal 698.2 is not provided.

In some embodiments of the flow communication unit according to the present disclosure, the proximal valve housing 697.1 comprises an enlarged channel portion adapted to accommodate the accommodative portion 698.3, wherein the accommodative portion of the self-contained valve comprises the first and the second proximal valve sealing surface, wherein the accommodative portion radially expands as the self-contained valve changes from the normal to the forced configuration, and wherein the proximal valve housing is adapted to provide a stop for the radial expansion, and thereby define the maximum expansion.

In some embodiments of the flow communication unit according to the present disclosure, the support member 697 further comprises a support portion 697.5 adapted to be supported by the drug delivery device 210, and thereby provide support for the flow communication unit in relation to the drug delivery device 210.

Embodiments with Reference to FIG. 6—Outlet Barrier

In some embodiments of the flow communication unit according to the present disclosure, the support member 697 comprises a distal end 697.11 and a distal portion 697.12 adapted to support the outlet barrier 650.

In some embodiments of the flow communication unit according to the present disclosure, the distal portion 697.12 comprises a surface portion defining the first outlet valve member 654 adapted to provide a seat sealing surface, wherein the outlet barrier 650 comprises a surface portion defining the second outlet valve member 655 adapted to provide a valve sealing surface, and wherein the outlet barrier seal 653 can be provided between the valve sealing surface and the seat sealing surface.

In some embodiments of the flow communication unit according to the present disclosure, the outlet barrier 650 comprises a proximal surface portion for interfacing the distal portion 697.12, and wherein the outlet barrier 650 is flexible and can be changed from a normal configuration to a forced configuration, in response to a fluid pressure on the proximal surface.

In some embodiments of the flow communication unit according to the present disclosure, the normally closed configuration of the flow communication unit 640 further comprises, the outlet barrier being in the normal configuration and provides the outlet barrier seal 653.

In some embodiments of the flow communication unit according to the present disclosure, the flow conducting device 230 comprises an enlarged channel inlet 238 adapted to accommodate a portion of a flexible portion 650.1 of the outlet barrier 650, wherein the flexible portion 650.1 of the outlet barrier 650 comprises the valve sealing surface, wherein the open configuration of the flow communication unit further comprises the enlarged channel inlet 238 accommodating the portion of the flexible portion 650.1 of the outlet barrier in the forced configuration, wherein the outlet barrier seal 653 is not provided.

Embodiments with Reference to FIG. 7—Proximal Support Member

In some embodiments of the flow communication unit according to the present disclosure, the flow communication unit further comprises a proximal support member 797 comprising a proximal end 797.9 and a proximal portion adapted 797.10 to support the proximal valve member 798.

In some embodiments of the flow communication unit according to the present disclosure, the proximal support member 797 is rigid, and the proximal valve member 798 is a self-contained valve 798 comprising a first valve member comprising a surface portion adapted to provide a first proximal valve sealing surface. The proximal valve member 798 further comprises a second valve member comprising a surface portion adapted to provide a second proximal valve sealing surface, wherein a proximal fluid tight seal 798.2 can be provided between the first and the second proximal valve sealing surface.

In some embodiments of the flow communication unit according to the present disclosure, the proximal support member 797 is rigid, and the proximal valve member comprises a skirt portion adapted to surround and fixedly engage the proximal portion 797.1 of the proximal support member 797.

In some embodiments of the flow communication unit according to the present disclosure, the self-contained valve 798 comprises a surface portion providing a portion of the inlet surface 241 for interfacing the drug delivery device 210, and wherein the self-contained valve 798 is flexible and can be changed from a normal configuration to a forced configuration, in response to a fluid pressure on the inlet surface 241.

In some embodiments of the flow communication unit according to the present disclosure, the flow communication unit 740 comprises a normally closed configuration, wherein the self-contained valve is in the normal configuration, and thereby provides the proximal fluid tight seal 798.2.

In some embodiments of the flow communication unit according to the present disclosure, the flow communication unit 740 comprises an open configuration, wherein the self-contained valve is in the forced configuration, and wherein the proximal fluid tight seal 798.2 is not provided.

In some embodiments of the flow communication unit according to the present disclosure, the proximal portion 797.1 of the proximal support member 797 comprises an enlarged channel portion adapted to receive a portion of a flexible portion 798.3 of the self-contained valve 798, wherein the flexible portion comprises a portion of the first and the second proximal valve sealing surface, wherein the flexible portion axially deflects into the enlarged channel portion, in response to the self-contained valve changes from the normal to the forced configuration, and wherein the proximal portion 797.1 is adapted to provide a stop for the axial deflection, and thereby define the maximum deflection.

In some embodiments of the flow communication unit according to the present disclosure, the proximal support member 797 further comprises a support portion 797.5 adapted to be supported by the drug delivery device 210, and thereby provide support for the flow communication unit in relation to the drug delivery device 210.

Embodiments with Reference to FIG. 7—Proximal Support Member —Distal Portion/Outlet Barrier In some embodiments of the flow communication unit according to the present disclosure, the proximal support member 797 comprises a distal end 797.11 and a distal portion 797.12 adapted to support the outlet barrier 750.

In some embodiments of the flow communication unit according to the present disclosure, the proximal support member 797 is rigid, and the distal portion 797.12 of the proximal support member 797 comprises a surface portion defining the first outlet valve member 754 adapted to provide a seat sealing surface, wherein outlet barrier 750 comprises a surface portion defining the second outlet valve member 755 adapted to provide a valve sealing surface, and wherein the outlet barrier seal 753 can be provided between the valve sealing surface and the seat sealing surface.

In some embodiments of the flow communication unit according to the present disclosure, the outlet barrier 750 comprises an inner surface portion for interfacing the distal portion 797.12 of proximal support member 797, and wherein the outlet barrier 750 is flexible and can be changed from a normal configuration to a forced configuration, in response to a fluid pressure on the inner surface portion.

In some embodiments of the flow communication unit according to the present disclosure, the normally closed configuration of the flow communication unit 740 further comprises, the outlet barrier being in the normal configuration and provides the outlet barrier seal 753.

In some embodiments of the flow communication unit according to the present disclosure, the proximal support member 797 provides a proximal portion of the first channel 247.

In some embodiments of the flow communication unit according to the present disclosure, the proximal portion of the first channel 247 provided by the proximal support member 797 extends from the proximal end 797.9 to an intermediate position 797.13.

In some embodiments of the flow communication unit according to the present disclosure, a distal portion of the first channel 247 is provided in a space between the distal portion 797.12 and the outlet barrier 750, and wherein the distal portion of the first channel extends from the intermediate position 797.13 to the outlet 749.

Embodiments with Reference to FIG. 7—Intermediate Valve Member

In some embodiments of the flow communication unit according to the present disclosure, the outlet barrier 750 provides an intermediate valve member 750.2.

In some embodiments of the flow communication unit according to the present disclosure, the distal portion 797.12 of the proximal support member 797 is adapted to support the intermediate valve member 750.2.

In some embodiments of the flow communication unit according to the present disclosure, the distal portion 797.12 of the proximal support member 797 comprises a surface portion defining an intermediate valve seat 750.3 adapted to provide an intermediate seat sealing surface, wherein the intermediate valve member 750.2 comprises a surface portion adapted to provide an intermediate valve sealing surface, and wherein an intermediate fluid tight seal can be provided between the intermediate valve sealing surface and the intermediate seat sealing surface.

In some embodiments of the flow communication unit according to the present disclosure, the intermediate valve member 750.2 comprises an inner surface portion for interfacing the proximal support member 797, and wherein the intermediate valve member 750.2 is flexible and can be changed from a normal configuration to a forced configuration, in response to a fluid pressure on the inner surface portion.

In some embodiments of the flow communication unit according to the present disclosure, the normally closed configuration of the flow communication unit 740 further comprises, the intermediate valve member being in the normal configuration and provides the intermediate fluid tight seal.

In some embodiments of the flow communication unit according to the present disclosure, the intermediate valve member is arranged in the distal portion of the first channel 247.

Embodiments with Reference to FIG. 7—Distal Support Member

In some embodiments of the flow communication unit according to the present disclosure the flow communication unit further comprises a distal support member 793.

In some embodiments of the flow communication unit according to the present disclosure, the distal support member 793 comprises a tubular portion 793.1 adapted to accommodate an accommodative portion of the outlet barrier 750, wherein the accommodative portion radially expands as the outlet barrier 750 changes from the normal to the forced configuration, and wherein the tubular portion 793.1 is adapted to provide a stop for the radial expansion, and thereby define the maximum expansion.

In some embodiments of the flow communication unit according to the present disclosure, the accommodative portion of the outlet barrier 750 comprises the second outlet valve member 755, wherein the open configuration of the flow communication unit 740 further comprises the outlet barrier being in the forced configuration, and wherein the outlet barrier seal 753 is not provided.

In some embodiments of the flow communication unit according to the present disclosure, the accommodative portion of the outlet barrier 750 comprises the intermediate valve member 750.2, wherein the open configuration of the flow communication unit 740 further comprises the outlet barrier being in the forced configuration, and wherein the intermediate fluid tight seal is not provided.

In some embodiments of the flow communication unit according to the present disclosure, the distal support member 793 further comprises a support portion adapted to be supported by the proximal support member, and thereby provide stability to the flow communication unit.

Embodiments with Reference to FIG. 7—Distal Sealing Member

In some embodiments of the flow communication unit according to the present disclosure, the flow communication unit further comprises a distal sealing member 794 providing the outlet sealing member 746.

In some embodiments of the flow communication unit according to the present disclosure, the distal support member 793 is adapted to support the distal sealing member 794.

Embodiments with Reference to FIG. 8—Proximal Valve Member

In some embodiments of the flow communication unit according to the present disclosure, the proximal valve member further comprises a support portion adapted to be supported by the drug delivery device 210, and thereby provide support for the flow communication unit in relation to the drug delivery device 210.

In some embodiments of the flow communication unit according to the present disclosure, the proximal valve member is adapted to fit into an adapter top 290 having a retaining member on an inner surface, wherein the proximal valve member comprises a planar distal surface, and a recess adapted to receive the retaining member when the proximal valve member is inserted into the adaptor top 290, and whereby the distal surface remains planar to allow close contact with another planar surface.

Embodiments with Reference to FIG. 8—Proximal Support Member

In some embodiments of the flow communication unit according to the present disclosure, the flow communication unit further comprises a proximal support member 897 comprising a proximal end 897.9 and a proximal portion adapted 897.10 to support the proximal valve member 898.

In some embodiments of the flow communication unit according to the present disclosure, the proximal support member 897 is rigid, and the proximal valve member 898 is a self-contained valve 898 comprising a first valve member comprising a surface portion adapted to provide a first proximal valve sealing surface, and a second valve member comprising a surface portion adapted to provide a second proximal valve sealing surface, wherein a proximal fluid tight seal 898.2 can be provided between the first and the second proximal valve sealing surface.

In some embodiments of the flow communication unit according to the present disclosure, the proximal support member 897 is rigid with a planar proximal surface, and wherein the self-contained valve comprises a substantially planar distal surface, and wherein the proximal support member is adapted to transfer a compression force to the self-contained valve 898, and wherein the self-contained valve is adapted to transfer a compression force to the drug delivery device.

In some embodiments of the flow communication unit according to the present disclosure, the proximal support member 897 is rigid, and wherein the proximal support member is adapted to fit into an adaptor top 290 having a retaining member on an inner surface, and wherein the proximal support member comprises a planar proximal surface adapted to be supported by the retaining member, and whereby the proximal surface can be retained in close contact with a distal planar surface of the self-contained valve 898, when the proximal support member 897 and the self-contained valve 898 are inserted into the adaptor top 290.

In some embodiments of the flow communication unit according to the present disclosure, the proximal support member 897 is rigid and provides a proximal portion of the first channel 247.

In some embodiments of the flow communication unit according to the present disclosure, the proximal portion of the first channel 247 provided by the proximal support member 897, extends from the proximal end 897.9 of the proximal support member 897.

In some embodiments of the flow communication unit according to the present disclosure, the self-contained valve 898 comprises a surface portion providing a portion of the inlet surface 241 for interfacing the drug delivery device 210, and wherein the self-contained valve 898 is flexible and can be changed from a normal configuration to a forced configuration, in response to a fluid pressure on the inlet surface 241.

In some embodiments of the flow communication unit according to the present disclosure, the flow communication unit 840 comprises a normally closed configuration, wherein the self-contained valve is in the normal configuration, and thereby provides the proximal fluid tight seal 898.2.

In some embodiments of the flow communication unit according to the present disclosure, the flow communication unit 840 comprises an open configuration, wherein the self-contained valve is in the forced configuration, and wherein the proximal fluid tight seal 898.2 is not provided.

In some embodiments of the flow communication unit according to the present disclosure, the proximal portion 897.1 of the proximal support member 897 comprises an enlarged channel portion adapted to receive a portion of a flexible portion 898.3 of the self-contained valve 898, wherein the flexible portion comprises a portion of the first and the second proximal valve sealing surface, wherein the portion of the flexible portion axially deflects into the enlarged channel portion, in response to the self-contained valve changes from the normal to the forced configuration, and wherein the proximal portion 797.1 is adapted to provide a stop for the axial deflection, and thereby define the maximum deflection.

Embodiments with Reference to FIG. 8—Intermediate Valve Member

In some embodiments of the flow communication unit according to the present disclosure, the flow communication unit further comprises an intermediate valve member 894.

In some embodiments of the flow communication unit according to the present disclosure, the proximal support member 897 comprises a distal end 897.11 and a distal portion 897.12 adapted to support the intermediate valve member 894.

In some embodiments of the flow communication unit according to the present disclosure, the proximal support member 897 is rigid, and the distal portion 897.12 of the proximal support member 897 comprises a surface portion defining an intermediate valve seat 897.6 adapted to provide an intermediate seat sealing surface, wherein the intermediate valve member 894 comprises a surface portion adapted to provide an intermediate valve sealing surface, and wherein an intermediate fluid tight seal 897.8 can be provided between the intermediate valve sealing surface and the intermediate seat sealing surface.

In some embodiments of the flow communication unit according to the present disclosure, the proximal portion of the first channel 247 extends from the proximal end 897.9 to the distal end 897.11.

In some embodiments of the flow communication unit according to the present disclosure, the intermediate valve member 894 comprises a proximal surface portion for interfacing the distal portion of the proximal support member 897, and wherein the intermediate valve member 894 is flexible and can be changed from a normal configuration to a forced configuration, in response to a fluid pressure on the proximal surface.

In some embodiments of the flow communication unit according to the present disclosure, the normally closed configuration of the flow communication unit 840 further comprises, the intermediate valve member being in the normal configuration and provides the intermediate fluid tight seal 897.8.

Embodiments with Reference to FIG. 8—Distal Support Member

In some embodiments of the flow communication unit according to the present disclosure, the flow communication unit further comprises a distal support member 893.

In some embodiments of the flow communication unit according to the present disclosure, the distal support member 893 is rigid and provides a distal portion of the first channel 247.

In some embodiments of the flow communication unit according to the present disclosure, the distal support member 893 comprises an enlarged channel portion 893.1 adapted to receive a portion of a flexible portion 894.2 of the intermediate valve member 894, wherein the flexible portion 894.2 of the intermediate valve member 894 comprises the intermediate valve sealing surface 894.1, wherein the open configuration of the flow communication unit 840 further comprises the enlarged channel portion 893.1 receiving the portion of the flexible portion of the intermediate valve member in the forced configuration, wherein the intermediate fluid tight seal 897.3 is not provided.

In some embodiments of the flow communication unit according to the present disclosure, the proximal support member 897, the intermediate valve member 894 and the distal support member 893 provides a unit, wherein a portion of the intermediate valve member is clamped between the support members, and wherein the support members are welded together by ultra-sound.

In some embodiments of the flow communication unit according to the present disclosure, the clamped portion is fixed and the unclamped portion is flexible and adapted to be moved between the normal and the forced configuration.

Embodiments with Reference to FIG. 8—Outlet Barrier

In some embodiments of the flow communication unit according to the present disclosure, the distal support member 893 comprises a distal end and a distal portion adapted to support the outlet barrier 850.

In some embodiments of the flow communication unit according to the present disclosure, the distal support member 893 is rigid, and the outlet barrier 850 is a self-contained valve 850 comprising a first valve member 854 comprising a surface portion adapted to provide a first proximal valve sealing surface, and a second valve member 855 comprising a surface portion adapted to provide a second proximal valve sealing surface, wherein a proximal fluid tight seal 853 can be provided between the first and the second proximal valve sealing surface.

In some embodiments of the flow communication unit according to the present disclosure, the self-contained valve 850 comprises a proximal surface portion for covering the first channel 247, and wherein the self-contained valve 850 is flexible and can be changed from a normal configuration to a forced configuration, in response to a fluid pressure in the first channel, and thereby on the proximal surface portion of the self-contained valve.

In some embodiments of the flow communication unit according to the present disclosure, the normally closed configuration of the flow communication unit 840 comprises the self-contained valve is in the normal configuration, and thereby provides the proximal fluid tight seal 853.

In some embodiments of the flow communication unit according to the present disclosure, the open configuration of the flow communication unit 840 comprises the self-contained valve is in the forced configuration, and wherein the proximal fluid tight seal 853 is not provided.

In some embodiments of the flow communication unit according to the present disclosure, the proximal portion 897.1 of the proximal support member 897 comprises an enlarged channel portion adapted to receive a portion of a flexible portion 898.3 of the self-contained valve 898, wherein the flexible portion comprises a portion of the first and the second proximal valve sealing surface, wherein the portion of the flexible portion axially deflects into the enlarged channel portion, in response to the self-contained valve changes from the normal to the forced configuration, and wherein the proximal portion 897.1 is adapted to provide a stop for the axial deflection, and thereby define the maximum deflection.

In some embodiments of the flow communication unit according to the present disclosure, the distal support member 893 is rigid with a planar distal surface, and wherein the self-contained valve comprises a substantially planar proximal surface, and wherein the distal support member is adapted to transfer a compression force to the outlet barrier 850, and wherein the outlet barrier is adapted to transfer a compression force to an adaptor top 290.

In some embodiments of the flow communication unit according to the present disclosure, the proximal support member 897 is rigid, and wherein the proximal support member, the intermediate valve member, the distal support member and the outlet barrier are adapted to fit into an adaptor top 290 having a retaining member on an inner surface, and wherein the proximal support member comprises a planar proximal surface adapted to be supported by the retaining member, and whereby the proximal surface can be retained in close contact with a the distal planar surface of the proximal valve member 898, when all members are inserted into the adaptor top 290.

In some embodiments of the flow communication unit according to the present disclosure, the proximal support member 897, the intermediate valve member 894 and the distal support member 893 provides a unit, wherein a portion of the intermediate valve member is clamped between the support members, and wherein the unit is adapted to be fitted into an adaptor top 290 having a unit retaining member adapted to retain the unit in a compressed state.

In some embodiments of the flow communication unit according to the present disclosure, the outlet barrier and the unit are adapted to be retained in a compressed state in the adaptor top, wherein the retaining member can transfer a compression force to the unit, and the unit can transfer the compression force to a retaining surface of the adaptor top 290.

In some embodiments of the flow communication unit according to the present disclosure, the outlet barrier and the unit are adapted to be retained in a compressed state in the adaptor top, wherein the proximal valve member is adapted to be fitted into the adaptor top in a compressed state, and wherein the adaptor top comprises a device retaining member on an inner surface, wherein the device retaining member is adapted to connect the adaptor top to the drug retaining device, wherein the proximal valve member is supported by the drug delivery device in a compressed state.

In some embodiments of the flow communication unit according to the present disclosure, the flow conducting device 230 comprises an enlarged channel inlet 238 adapted to receive a portion of a flexible portion 850.1 of the self-contained valve 850, wherein the flexible portion 850.1 of the self-contained valve 850 comprises a portion of the outlet barrier seal 853, wherein the open configuration of the flow communication unit further comprises the enlarged channel inlet 238 receiving the portion of the flexible portion 850.1 of the outlet barrier in the forced configuration, wherein the outlet barrier seal 853 is not provided.

In some embodiments of the flow communication unit according to the present disclosure, the outlet barrier 850 provides the outlet sealing member 846.

In a further aspect the flow conducting device comprises sealing members adapted to cooperate with the outlet sealing members of provided on the outlet barrier.

In a further aspect the outlet barrier is stretched by the sealing members of the flow conducting device, wherein the first and the second outlet sealing members are pulled away from each other (indicated by arrow 896 on FIG. 8D), and thereby decreases the strength of the fluid tight outlet seal.

In a further aspect the outlet barrier being in the closed configuration further comprises, the outlet barrier being adapted to allow a drug contained in the first channel to flow downstream from the channel inlet and out of the channel outlet, in response to the pressure in the first channel being above a second threshold, wherein the second threshold is larger than the first threshold, as the outlet barrier is not stretched in the closed configuration.

In some embodiments of the flow communication unit according to the present disclosure, the distal support member 893 comprises a distal end and a distal portion adapted to support the outlet barrier 850, wherein
- the distal support member further comprises a spacing member 893.2 adapted to separate the supported outlet barrier from the distal support member, whereby a space is provided between the distal support member and the outlet barrier, and
- wherein the outlet barrier 850 comprises an actuator portion 850.2 providing the outlet sealing member 846 and movably arranged between a first position and a second position relative to the spacing member 893.2, and adapted to be configured in an:
  - (i) unconnected configuration, wherein the outlet barrier is in the closed configuration, wherein the closed configuration of the outlet barrier further comprises the actuator portion 850.2 being in the first position relative to the spacing member 893.2, whereby the second outlet valve member 855 is adapted to cooperate with the first outlet valve member 854 to provide the outlet barrier seal 853 adapted to allow a drug contained in the first channel to flow downstream from the channel inlet and out of the channel outlet 849, in response to the pressure in the first channel 247 being above a second threshold, wherein the second threshold defines the tightness of the outlet barrier seal 853 and is larger than the first threshold,
  - (ii) a connected configuration, wherein the outlet barrier is in the flow configuration, wherein the flow configuration of the outlet barrier further comprises the actuator portion 850.2 is in the second position relative to the spacing member 893.2, whereby the second outlet valve member 855 is adapted to cooperate with the first outlet valve member 854 to provide the outlet barrier seal 853 adapted allow a drug contained in the first channel to flow downstream from the channel inlet and out of the channel outlet 849, in response to the pressure in the first channel 247 being above the first threshold, wherein the first threshold defines the tightness of the outlet barrier seal.

Hereby, the actuator portion, which also provides the outlet sealing member 846, is adapted to be manipulated from the first position to the second position, by the flow conducting device upon connection.

Hereby is provided a flow communication unit, wherein the flow communication unit is further adapted for being in:
- (i) the unconnected configuration, wherein the tightness of the barrier seal 853 is defined by a second threshold, and
- (ii) the connected configuration, wherein the tightness of the barrier seal 853 is defined by the first threshold.

Embodiments with Reference to FIG. 9—Proximal Valve Member

In some embodiments of the flow communication unit according to the present disclosure, the proximal valve member 998 provides the channel inlet 948 in a normal configuration, wherein the valve is closed.

In some embodiments of the flow communication unit according to the present disclosure, the proximal valve member provides a channel passage in a forced configuration, wherein the valve is open.

In some embodiments of the flow communication unit according to the present disclosure, the proximal valve member comprises a distal surface portion for interfacing a movable channel member, and wherein the proximal valve member 998 is flexible and can be changed from a normal configuration to a forced configuration, in response to a pressure from the movable channel member on the distal surface portion.

Embodiments with Reference to FIG. 9 —Proximal Support Member

In some embodiments of the flow communication unit according to the present disclosure, the flow communication unit further comprises a proximal support member 997 comprising a proximal end 997.9 and a proximal portion adapted 997.10 to support the proximal valve member 998.

In some embodiments of the flow communication unit according to the present disclosure, the proximal support member 997 is rigid, wherein the proximal valve member 998 is a self-contained valve 998 comprising a first valve member comprising a surface portion adapted to provide a first proximal valve sealing surface, and a second valve member comprising a surface portion adapted to provide a second proximal valve sealing surface, wherein a proximal fluid tight seal 998.2 can be provided between the first and the second proximal valve sealing surface.

In some embodiments of the flow communication unit according to the present disclosure, the proximal support member 997 is rigid, and wherein the self-contained valve 998 comprises a skirt portion adapted to surround and/or be surrounded by the proximal portion 997.1 of the proximal support member 997, whereby the self-contained valve and the proximal support member are fixedly engaged to each other.

In some embodiments of the flow communication unit according to the present disclosure, the self-contained valve 998 comprises a proximal surface portion providing a portion of the inlet surface 241 for interfacing the drug delivery device 210, and a distal surface portion for interfacing a movable channel member. The self-contained valve 998 is flexible and (i) the self-contained valve can be changed from a normal configuration to a forced configuration, in response to a pressure from the movable channel member on the distal surface portion, and (ii) the movable channel member supports the self-contained valve 998 in the normal configuration, in response to a fluid pressure on the inlet surface 241, and whereby the fluid tight seal 998.2 remains tight.

In some embodiments of the flow communication unit according to the present disclosure, the flow communication unit 940 comprises a normally closed configuration, wherein the self-contained valve is in the normal configuration, and thereby provides the proximal fluid tight seal 998.2.

In some embodiments of the flow communication unit according to the present disclosure, the flow communication unit 940 comprises an open configuration, wherein the self-contained valve is in the forced configuration and the channel inlet 948 is provided by the movable channel member, and wherein the proximal fluid tight seal 998.2 is not provided.

In some embodiments of the flow communication unit according to the present disclosure, the proximal portion 997.1 of the proximal support member 997 is adapted to receive a portion of the self-contained valve 998, wherein the received portion of the self-contained valve 998 defines a channel seat portion, wherein the channel seat portion is adapted to provide a seat for a proximal portion of the movable channel member in a distal position, and wherein the self-contained valve is in the forced configuration.

In some embodiments of the flow communication unit according to the present disclosure, the proximal portion 997.1 of the proximal support member 997 is adapted to receive a portion of the self-contained valve 998 defining a channel seat portion, wherein the channel seat portion is adapted to provide a seat for a distal portion of the movable channel member in a proximal position, wherein the movable channel member extends across the self-contained valve 998, wherein the self-contained valve 998 provides a seal around the movable channel member, and wherein the self-contained valve is in the forced configuration.

In some embodiments of the flow communication unit according to the present disclosure, the proximal support member 997 further comprises a support portion 997.5 adapted to be supported by the drug delivery device 210, and thereby provide support for the flow communication unit in relation to the drug delivery device 210.

Embodiments with Reference to FIG. 9—Proximal Support Member—Distal Portion

In some embodiments of the flow communication unit according to the present disclosure, the proximal support member 997 comprises a distal end 997.11 and a distal portion 997.12 adapted to support the outlet barrier 750.

Embodiments with Reference to FIG. 9—Distal Support Member

In some embodiments of the flow communication unit according to the present disclosure, the flow communication unit further comprises a distal support member 993.

In some embodiments of the flow communication unit according to the present disclosure, wherein the proximal support member 997 comprises a tubular portion adapted to accommodate the distal support member 993, wherein the distal support member 993 is movably arranged within the tubular portion, and wherein the distal support member is adapted to be moved between a distal position and a proximal position.

In some embodiments of the flow communication unit according to the present disclosure, the distal support member 993 comprises a proximal end 993.9 and a proximal portion 993.10 comprising a movable channel member.

In some embodiments of the flow communication unit according to the present disclosure, the distal support member 993 comprises a distal end 993.11 and a distal portion 993.12 adapted to support the outlet barrier 950.

In some embodiments of the flow communication unit according to the present disclosure, the distal support member 993 is rigid, and wherein the distal portion 993.12 of the distal support member 993 comprises a surface portion defining the first outlet valve member 954 adapted to provide a seat sealing surface, wherein outlet barrier 950 comprises a surface portion defining the second outlet valve member 955 adapted to provide a valve sealing surface, and wherein the outlet barrier seal 953 can be provided between the valve sealing surface and the seat sealing surface. 134. The flow communication unit according to any of claims 129-133, wherein the outlet barrier (950) comprises an inner surface portion for interfacing the distal portion (993.12) of the distal support member (993), and wherein the outlet barrier (950) is flexible and can be changed from a normal configuration to a forced configuration, in response to a fluid pressure on the inner surface portion.

In some embodiments of the flow communication unit according to the present disclosure, the normally closed configuration of the flow communication unit 940 further comprises, the outlet barrier being in the normal configuration and provides the outlet barrier seal 953.

In some embodiments of the flow communication unit according to the present disclosure, the proximal portion 993.10 of the distal support member 993 provides a proximal portion of the first channel 247.

In some embodiments of the flow communication unit according to the present disclosure, the proximal portion of the first channel 247 provided by the distal support member 993 extends from the proximal end 993.9 to an intermediate position 993.13.

In some embodiments of the flow communication unit according to the present disclosure, a distal portion of the first channel 247 is provided between the distal portion 993.12 and the outlet barrier 950, and wherein the distal portion of the first channel extends from the intermediate position 997.13 to the outlet 949.

In some embodiments of the flow communication unit according to the present disclosure, the flow communication comprises a biasing member 994 adapted to bias the distal support member 993 towards the distal position.

In some embodiments of the flow communication unit according to the present disclosure, the biasing member 994 is positioned between a distal surface of the proximal support member 998 and a proximal surface of the distal support member 993.

In some embodiments of the flow communication unit according to the present disclosure, the biasing member 994 is a compression spring.

Embodiments with Reference to FIG. 9—Intermediate Valve Member

In some embodiments of the flow communication unit according to the present disclosure, the outlet barrier 950 provides an intermediate valve member 950.2.

In some embodiments of the flow communication unit according to the present disclosure, the distal portion 993.12 of the distal support member 993 is adapted to support the intermediate valve member 950.2.

In some embodiments of the flow communication unit according to the present disclosure, the distal portion 993.12 of the distal support member 993 comprises a surface portion defining an intermediate valve seat 993.14 adapted to provide an intermediate seat sealing surface, wherein the intermediate valve member 950.2 comprises a surface portion adapted to provide an intermediate valve sealing surface, and wherein an intermediate fluid tight seal can be provided between the intermediate valve sealing surface and the intermediate seat sealing surface.

In some embodiments of the flow communication unit according to the present disclosure, the intermediate valve member 950.2 comprises an inner surface portion for interfacing the distal support member 993, and wherein the intermediate valve member 950.2 is flexible and can be changed from a normal configuration to a forced configuration, in response to a fluid pressure on the inner surface portion.

In some embodiments of the flow communication unit according to the present disclosure, the normally closed configuration of the flow communication unit 940 further comprises, the intermediate valve member being in the normal configuration and provides the intermediate fluid tight seal.

In some embodiments of the flow communication unit according to the present disclosure, the intermediate valve member is positioned in the distal portion of the first channel (247), and provides additional safety.

Embodiments with Reference to FIG. 9—Outlet Barrier

In some embodiments of the flow communication unit according to the present disclosure, the outlet sealing member 946 is provided by the outlet barrier 950.

Embodiments with Reference to FIG. 10, 11, 12

In some embodiments of the flow communication unit 1040, 1140, 1240 according to the present disclosure, the flow communication unit further comprises a central portion 1198, 1298 extending from the inlet surface 241 to the outlet surface 242, wherein the central portion provides a portion of the inlet surface and the outlet surface, and wherein the central portion comprises the first flow channel 247, the central portion further comprises a side surface extending in a direction between the inlet and the outlet surface 242, wherein the channel outlet 1049, 1149 and the first outlet valve member 1054, 1154, 1254 is provided in the side surface, and wherein the first outlet valve member surrounds the channel outlet 1049, 1149, 1249.

The outlet barrier 1050, 1150, 1250 surrounds the central portion and provides the second outlet valve member 1055, 1155, 1255, and the outlet barrier 1050, 1150, 1250 is movably arranged and can be moved between a distal position and a proximal position The outlet surface 242 can be arranged in the connected configuration, when the outlet barrier 1050, 1150, 12050 is positioned in the proximal position, and the outlet surface 242 can be arranged in the unconnected configuration, when the outlet barrier 1050, 1150, 1250 is positioned in the distal position.

A circumferential portion 1197, 1297, connected to the central portion, provides the intermediate surfaces 243, 244 extending between the inlet surface and the outlet surface, and wherein the circumferential portion comprises a portion of the inlet and the outlet surface.

The inlet surface, the outlet surface and the intermediate surfaces define the outer surface and confines the interior space 245 of the flow communication unit, for the outlet surface 242 being in any of the connected and the unconnected configurations, wherein the outlet barrier is positioned proximally or distally.

The outlet sealing member 1046, 1146, 1246 is provided in the side surface of the central portion, and the outlet sealing member surrounds the channel outlet 1049, 1149, 1249, whereby the outlet sealing member provides a portion of the outlet surface 242 in the connected configuration.

The outlet barrier 1050, 1150, 1250 provides a portion of the outlet surface 242, wherein the outlet surface provided by the outlet barrier is flush with the outlet portions provided by the central and the circumferential portion, when the outlet surface is in the unconnected configuration, whereby it is easier to keep the outlet surface clean.

Further, the outlet barrier 1050, 1150, 1250 provides a portion of the outlet surface 242, wherein the outlet surface provided by the outlet barrier is depressed relative to outlet surface portions provided by the central and the circumferential portion, when the outlet surface is in the connected configuration.

The second outlet valve member 1055, 1155, 1255 is adapted to cooperate with the first outlet valve member 1054, 1154 to provide an outlet barrier seal 1053, 1153, 1253, wherein the outlet barrier is adapted for being in:
  (i) a closed configuration, wherein the outlet surface is in the unconnected configuration, whereby the outlet barrier is in the distal position, and whereby the outlet barrier seal is adapted to reduce the entrance of contaminations, and
  (ii) a flow configuration, wherein the outlet surface is in the connected configuration, whereby the outlet barrier is in the proximal position, whereby the outlet barrier 1050, 1150, 1250 is adapted to allow a drug contained in the first channel 247 to flow downstream from the channel inlet and out of the channel outlet 1049, 1149, 1249, in response to the pressure in the first channel 247 being above the first threshold.

The flow communication unit is further adapted for being in:
  (i) the unconnected configuration, in response to disconnecting the flow communication unit from the flow conducting device, and wherein the outlet barrier 1050, 1150, 1250 is allowed to be in the closed configuration, and
  (ii) the connected configuration, in response to connecting the flow communication unit to the flow conducting device 230, wherein the outlet barrier is allowed to be in the flow configuration, wherein the outlet sealing member 1046, 1146, 1246 is arranged to be able to contact the flow conducting device to provide the channel seal 1060, 1160, 1260 downstream to the channel outlet 1049 to allow flow communication between the channel outlet 1049, 1149, 1249 and the flow conducting device, wherein the channel outlet 1049, 1149, 1249 for the first channel is arranged at the outlet surface (242) of the flow communication unit.

Hereby a combined flow channel 267 can be provided between the drug delivery device 210, the first channel 247 and the flow conducting device 230 with the channel seal arranged downstream to the channel outlet, when the channel inlet is arranged in flow communication with the drug delivery device and the flow communication unit 1040, 1140, 1240 is in the connected configuration.

In this way the flow communication unit 1040, 1140, 1240 is adapted to enable the extended use of the multi-use drug delivery device, and whereby the flow communication unit is adapted to inhibit microbial entrance in the multi-use drug delivery device during the extended use.

Embodiments with Reference to FIG. 10,
12—Locking Member

In some embodiments the flow communication unit 1040, 1240 according to the present disclosure further comprises an outlet barrier locking member 1050.10, 1250.10 adapted to be released by the flow conducting device 230 upon connection. The outlet barrier is further adapted for being in (i) the closed configuration, wherein the outlet surface is in the unconnected configuration, wherein the outlet barrier is locked by the outlet barrier locking member 1050.10, 1250.10 in the distal position, and (ii) a flow configuration, wherein the outlet surface is in the connected configuration, wherein the outlet barrier is released and allowed to be moved to the proximal position.

In some embodiments the flow communication unit 1040, 1240 according to the present disclosure the barrier locking member 1050.10, 1250.10 is further adapted for being released by a connecting member 230.10 of the flow conducting device 230.

List of Embodiments

A flow communication unit (240, 540, 640, 740, 840, 940, 1040, 1140, 1240) for establishing flow communication from a multi-use drug delivery device (210) adapted for extended use, to a flow conducting device (230), wherein the drug delivery device (210) comprises a reservoir comprising multiple doses of a liquid drug formulation, wherein the reservoir is adapted to pressurize the liquid drug formulation, wherein the flow conducting device (230) is adapted for conducting the drug to the subcutaneous tissue of a subject, wherein the flow communication unit comprises:
  an inlet surface (241) for interfacing a drug delivery device (210),
  an outlet surface (242) configured for being in: (i) a connected configuration, wherein the outlet surface allows the flow communication unit and the flow conducting device to be connected, and wherein the outlet surface is adapted for interfacing the flow conducting device (230), (ii) an unconnected configuration, wherein the outlet surface allows the flow communication unit and the flow conducting device to be unconnected, and wherein the outlet surface is adapted for reducing the entrance of contaminations into the interior space (245) of the flow communication unit;
  intermediate surfaces (243, 244) extending between the inlet surface and the outlet surface, wherein the inlet surface, the outlet surface and the intermediate surfaces define an outer surface and confines an interior space (245) of the flow communication unit, for the outlet surface being in any of the connected and the unconnected configurations,
  an outlet sealing member (246, 546, 646, 746, 846, 946, 1046, 1146, 1246) providing a portion of the outlet surface (242), for the outlet surface being in the connected configuration, wherein the outlet sealing member (246, 546, 646, 746, 846, 946, 1046, 1146, 1246) is adapted for contacting the flow conducting device to establish a fluid tight channel seal (260, 560, 660, 760, 860, 960, 1060, 1160, 1260), wherein the outlet sealing member is adapted to provide fluid tight contact with the flow conducting device, wherein the functionality of a second valve member can be maintained or improved upon contact with the flow conducting device,
  a first flow channel (247) comprising a channel inlet (248, 348, 448, 548, 648, 748, 948, 1048, 1148, 1248) adapted for providing flow communication with the drug delivery device, and a channel outlet (249, 549, 649, 749, 849, 949, 1049, 1149, 1249) adapted for providing flow communication with the flow conducting device,
  a first outlet valve member (554, 654, 754, 854, 954, 1054, 1154, 1254),
  an outlet barrier (250, 550, 660, 760, 850, 950, 1050, 1150, 1250) comprising the second outlet valve member (555, 655, 755, 855, 955, 1055, 1155, 1255) adapted to cooperate with the first outlet valve member (554, 654, 754, 854, 954, 1054, 1154, 1254), wherein the outlet barrier (250, 550, 650, 750, 850, 950, 1050, 1150, 1250) provides a portion of the outlet surface (242), and wherein the outlet barrier is configured for being in:
  (i) a closed configuration, wherein the outlet surface is in the unconnected configuration, wherein the second outlet valve member (555, 655, 755, 855, 955, 1055, 1155, 1255) is adapted to cooperate with the first outlet valve member (554, 654, 754, 854, 954, 1054, 1154, 1254) to provide an outlet barrier seal (253, 553, 653, 753, 853, 953, 1053, 1153, 1253), and wherein the outlet barrier seal is adapted to reduce the entrance of contaminations through the channel outlet and into the first channel, and
  (ii) a flow configuration, wherein the outlet surface is in the connected configuration, wherein the second outlet valve member (555, 655, 755, 855, 955, 1055, 1155, 1255) is adapted to cooperate with the first outlet valve member (554, 654, 754, 854, 954, 1054, 1154, 1254) to allow a drug contained in the first channel (247) to flow downstream from the channel inlet and out of the channel outlet (249, 549, 749, 849, 949, 1049, 1149, 1249), in response to the pressure in the first channel (247) being above a first threshold;
wherein the flow communication unit is further adapted for being in:
  (i) an unconnected configuration, in response to disconnecting the flow communication unit from the flow conducting device, wherein the outlet surface is in the unconnected configuration, and wherein the outlet barrier is in the closed configuration, and
  (ii) a connected configuration, in response to connecting the flow communication unit to the flow conducting device (230), wherein the outlet surface is in the connected configuration, wherein the outlet barrier is in the flow configuration, wherein the outlet sealing member (246, 546, 646, 746, 946, 1046, 1146, 1246) is arranged to be able to contact the flow conducting device to provide the channel seal (260, 560, 660, 760, 860, 960, 1060, 1160, 1260) downstream to the channel outlet (249, 549, 649, 749, 849, 949, 1049, 1149) of the first flow channel, and thereby adapted to allow flow communication between the channel outlet (249, 549, 649, 746, 849, 949, 1049, 1149, 1249) and the flow conducting device, wherein the channel outlet (249, 549, 649, 749, 849, 949, 1049, 1149, 1249) is arranged at the outlet surface (242) of the flow communication unit; and wherein a combined flow channel (267) can be provided between the drug delivery device (210), the first flow channel (247) and the flow conducting device (230) with the channel seal arranged downstream to the channel outlet, in response to the channel inlet being arranged in flow communication with the drug delivery device and the flow communication unit (240, 540, 640, 740, 840, 940, 1040, 1140, 1240) being connected to the flow conducting device;

whereby the flow communication unit (240, 540, 640, 740, 840, 940, 1040, 1140, 1240) is adapted to enable the extended use of the multi-use drug delivery device, and whereby the flow communication unit is adapted to inhibit microbial entrance in the multi-use drug delivery device during the extended use.

Channel Outlet

2. The flow communication unit according to embodiment 1, wherein the outlet barrier (550, 650, 750, 850, 950) provides the channel outlet (549, 649, 749, 849, 949).

Unidirectional Valve

3. The flow communication unit (240, 540, 640, 740, 840, 940, 1040, 1140, 1240) according to any of embodiment 1, wherein the flow communication unit further comprises a unidirectional valve (270) arranged along the first channel (247) and adapted for guiding the flow downstream and inhibiting upstream flow towards the drug delivery device.

Proximal Piercing Needle

4. The flow communication unit (1140, 1240) according to any of embodiments 1 and 3, wherein the flow communication unit further comprises a proximal piercing needle (391, 491, 1191, 1291) extending from the inlet surface in an extended configuration, wherein the proximal needle comprises a proximal open end providing the channel inlet (249).

5. The flow communication unit according to embodiment 4, wherein the flow communication unit further comprises a proximal piercing needle actuator (492) adapted to change the proximal piercing needle from a retracted configuration to the extended configuration, in response to connecting the flow communicating unit with the flow conducting device.

Embodiment: FIG. 5, 6, 7, 8, 9

6. The flow communication unit according to any of the embodiments 1 and 3, wherein the flow communication unit further comprises a proximal valve member (598, 698, 798, 898, 998), adapted to allow a flow from the inlet towards the outlet and for preventing a reverse flow.

7. The flow communication unit according to embodiment 6, wherein the proximal valve member (598, 698, 798, 898, 998) provides a portion of the inlet surface (241) for interfacing the drug delivery device (210).

8. The flow communication unit according to any of embodiments 6-7, wherein the proximal valve member (598, 698, 798, 898, 998) provides a portion of the intermediate surfaces (243, 244) extending between the inlet surface (241) and the outlet surface (242).

9. The flow communication unit according to any of embodiments 6-8, wherein the portion of the intermediate surfaces (243, 244) is soft and provides a device sealing surface (598.1, 698.1, 798.1, 898.1, 998.1) to seal against the drug delivery device (210).

Embodiment: FIG. 5, 6, 7, 8

10. The flow communication unit according to any of embodiments 6-9, wherein the proximal valve member provides the channel inlet (548, 648, 748, 848).

Embodiment: FIG. 5

Proximal Support Member

11. The flow communication unit according to any of embodiments 1, 3 and 6-10, wherein the flow communication unit further comprises a proximal support member (597, 797) comprising a proximal end (597.9, 797.9) and a proximal portion adapted (597.10, 797.10) to support the proximal valve member (598, 798).

12. The flow communication unit according to embodiment 11, wherein the proximal support member (597) is rigid, and wherein the proximal portion of the proximal support member (597) comprises a surface portion defining a proximal valve seat (597.1) adapted to provide a proximal seat sealing surface (597.2), wherein the proximal valve member (598) comprises a surface portion adapted to provide a proximal valve sealing surface (598.2), and wherein a proximal fluid tight seal (597.3) can be provided between the proximal valve sealing surface (598.2) and the proximal seat sealing surface (597.2).

13. The flow communication unit according to any of embodiments 11-12, wherein the proximal support member (597) is rigid and provides a proximal portion of the first channel (247).

14. The flow communication unit according to embodiment 13, wherein the proximal portion of the first channel (247) provided by the proximal support member (597), extends from the proximal end (597.9) of the proximal support member (597).

15. The flow communication unit according to any of embodiments 13-14, wherein the proximal valve member (598) comprises a surface portion providing a portion of the inlet surface (241) for interfacing the drug delivery device (210), and wherein the proximal valve member (598) is flexible and can be changed from a normal configuration to a forced configuration, in response to a fluid pressure on the inlet surface (241).

16. The flow communication unit according to embodiment 15, wherein the flow communication unit (540) comprises a normally closed configuration, wherein the proximal valve member is in the normal configuration, and thereby provides the proximal fluid tight seal (597.3).

17. The flow communication unit according to embodiment 16, wherein the proximal support member (597) comprises an enlarged channel portion (597.4) adapted to accommodate an accommodative portion (598.3) of the proximal valve member, wherein the accommodative portion of the proximal valve member comprises the proximal valve sealing surface (598.2), wherein the flow communication unit (540) comprises an open configuration, wherein the enlarged channel portion (597.4) accommodates the accommodative portion of the proximal valve member in the forced configuration, and wherein the proximal fluid tight seal (597.3) is not provided.

18. The flow communication unit according to any of embodiments 11-17, wherein the proximal support member (597, 697) further comprises a support portion (597.5, 697.5) adapted to be supported by the drug delivery device (210), and thereby provide support for the flow communication unit in relation to the drug delivery device (210).

Intermediate Valve Member

19. The flow communication unit according to any of the embodiments 1, 6-18 comprising an intermediate valve member (594).

20. The flow communication unit according to embodiment 19, wherein the proximal support member (597) comprises a distal end (597.11) and a distal portion (597.12) adapted to support the intermediate valve member (594).

21. The flow communication unit according to embodiment 20, wherein the proximal support member (597) is rigid, and wherein the distal portion (597.12) of the proximal support member (597) comprises a surface portion defining an intermediate valve seat (597.6) adapted to provide an intermediate seat sealing surface (597.7), wherein the intermediate valve member (594) comprises a surface portion adapted to provide an intermediate valve sealing surface (594.1), and wherein an intermediate fluid tight seal (597.8) can be provided between the intermediate valve sealing surface (594.1) and the intermediate seat sealing surface (597.7).

22. The flow communication unit according to any of embodiments 20-21, wherein the proximal portion of the first channel (247) provided by the proximal support member (597) extends from the proximal end (597.9) to the distal end (597.11).

23. The flow communication unit according to any of embodiments 19-22, wherein the intermediate valve member (594) comprises a proximal surface portion for interfacing the proximal support member (597), and wherein the intermediate valve member (594) is flexible and can be changed from a normal configuration to a forced configuration, in response to a fluid pressure on the proximal surface.

24. The flow communication unit according to embodiment 23, wherein the normally closed configuration of the flow communication unit (540) further comprises, the intermediate valve member being in the normal configuration and provides the intermediate fluid tight seal (597.8).

Distal Support Member

25. The flow communication unit according to any of the embodiments 1, 6-24 comprising a distal support member (593).

26. The flow communication unit according to embodiment 25, wherein the distal support member (593) is rigid and provides a distal portion of the first channel (247).

27. The flow communication unit according to embodiment 26, wherein the distal support member (593) comprises an enlarged channel portion (593.1) adapted to receive a portion of a flexible portion (594.2) of the intermediate valve member (594), wherein the flexible portion (594.2) of the intermediate valve member (594) comprises the intermediate valve sealing surface (594.1), wherein the open configuration of the flow communication unit (540) further comprises the enlarged channel portion (593.1) receiving the portion of the flexible portion of the intermediate valve member in the forced configuration, wherein the intermediate fluid tight seal (597.3) is not provided.

28. The flow communication unit according to any of embodiments 25-27, wherein the distal support member (593) further comprises a support portion adapted to be supported by the proximal support member, and thereby provide stability to the flow communication unit.

29. The flow communication unit according to any of the embodiments 25-28, wherein the distal support member (593) and the proximal support member (597) are adapted to clamp a portion of the intermediate valve member (594), and whereby the clamped portion is fixed and the unclamped portion adapted to be moved between the normal and the forced configuration.

30. The flow communication unit according to any of embodiments 25-29, wherein the distal support member (593) further comprises a support portion adapted to be supported by the drug delivery device (210), and thereby provide support for the flow communication unit in relation to the drug delivery device (210).

Outlet Barrier

31. The flow communication unit according to any of the embodiments 1, 25-30, wherein the distal support member (593) comprises a distal end and a distal portion adapted to support the outlet barrier (550).

32. The flow communication unit according to embodiment 31, wherein the distal support member (593) is rigid, and wherein the distal portion of the distal support member (593) comprises a surface portion defining the first outlet valve member (554) adapted to provide a seat sealing surface, wherein the outlet barrier (550) comprises a surface portion defining the second outlet valve member (555) adapted to provide a valve sealing surface, and wherein the outlet barrier seal (553) can be provided between the valve sealing surface and the seat sealing surface.

33. The flow communication unit according to any of embodiments 31-32, wherein the outlet barrier (550) comprises a proximal surface portion for interfacing the distal support member (593), and wherein the outlet barrier (550) is flexible and can be changed from a normal configuration to a forced configuration, in response to the pressure in the first channel (247) and on the proximal surface portion being above the first threshold.

34. The flow communication unit according to embodiment 33, wherein the normally closed configuration of the flow communication unit (540) further comprises, the outlet barrier being in the normal configuration and provides the outlet barrier seal (553).

35. The flow communication unit according to embodiment 34, wherein the flow conducting device (230) comprises an enlarged channel inlet (238) adapted to receive a portion of a flexible portion (550.1) of the outlet barrier (550), wherein the flexible portion (550.1) of the outlet barrier (550) comprises the valve sealing surface, wherein the open configuration of the flow communication unit further comprises the enlarged channel inlet (238) receiving the portion of the flexible portion (550.1) of the outlet barrier in the forced configuration, wherein the outlet barrier seal (553) is not provided.

36. The flow communication unit according to any of the previous embodiments, wherein the outlet barrier (550) provides the outlet sealing member (546).

Embodiment: FIG. 6

37. The flow communication unit according to any of embodiments 1, 3 and 6-10, wherein the flow communication unit further comprises a support member (697) comprising a proximal end (697.9) and a proximal portion adapted (697.10) to support the proximal valve member (698).

38. The flow communication unit according to embodiment 37, wherein the support member (697) is rigid, wherein the proximal valve member (698) is a self-contained valve (698) comprising a first valve member comprising a surface portion adapted to provide a first proximal valve sealing surface, and a second valve member comprising a surface portion adapted to provide a second proximal valve sealing surface, wherein a proximal fluid tight seal (698.2) can be provided between the first and the second proximal valve sealing surface.

39. The flow communication unit according to any of embodiments 37-38, wherein the support member (697) is rigid, and wherein the proximal portion of the support member (697) comprises a proximal valve housing (697.1) adapted to accommodate an accommodative portion (698.3) of the self-contained valve (698).

40. The flow communication unit according to any of embodiments 37-39, wherein the support member (697) provides a portion of the first channel (247).

41. The flow communication unit according to embodiment 40, wherein the portion of the first channel (247), extends from the proximal end (697.9) of the support member (697).

42. The flow communication unit according to any of embodiments 38-41, wherein the self-contained valve (698) comprises a surface portion providing a portion of the inlet surface (241) for interfacing the drug delivery device (210), and wherein the self-contained valve (698) is flexible and can be changed from a normal configuration to a forced configuration, in response to a fluid pressure on the inlet surface (241).

43. The flow communication unit according to embodiment 42, wherein the flow communication unit (640) comprises a normally closed configuration, wherein the self-contained valve is in the normal configuration, and thereby provides the proximal fluid tight seal (698.2).

44. The flow communication unit according to embodiment 43, wherein the flow communication unit (540) comprises an open configuration, wherein the self-contained valve is in the forced configuration, and wherein the proximal fluid tight seal (698.2) is not provided.

45. The flow communication unit according to embodiment 44, wherein the proximal valve housing (697.1) comprises an enlarged channel portion adapted to accommodate the accommodative portion (698.3), wherein the accommodative portion of the self-contained valve comprises the first and the second proximal valve sealing surface, wherein the accommodative portion radially expands as the self-contained valve changes from the normal to the forced configuration, and wherein the proximal valve housing is adapted to provide a stop for the radial expansion, and thereby define the maximum expansion.

46. The flow communication unit according to any of embodiments 37-45, wherein the support member (697) further comprises a support portion (697.5) adapted to be supported by the drug delivery device (210), and thereby provide support for the flow communication unit in relation to the drug delivery device (210).

Outlet Barrier

47. The flow communication unit according to any of embodiments 37-46, wherein the support member (697) comprises a distal end (697.11) and a distal portion (697.12) adapted to support the outlet barrier (650).

48. The flow communication unit according to embodiment 47, wherein the distal portion (697.12) comprises a surface portion defining the first outlet valve member (654) adapted to provide a seat sealing surface, wherein the outlet barrier (650) comprises a surface portion defining the second outlet valve member (655) adapted to provide a valve sealing surface, and wherein the outlet barrier seal (653) can be provided between the valve sealing surface and the seat sealing surface.

49. The flow communication unit according to any of embodiments 47-48, wherein the outlet barrier (650) comprises a proximal surface portion for interfacing the distal portion (697.12), and wherein the outlet barrier (650) is flexible and can be changed from a normal configuration to a forced configuration, in response to a fluid pressure on the proximal surface.

50. The flow communication unit according to embodiment 49, wherein the normally closed configuration of the flow communication unit (640) further comprises, the outlet barrier being in the normal configuration and provides the outlet barrier seal (653).

51. The flow communication unit according to embodiment 50, wherein the flow conducting device (230) comprises an enlarged channel inlet (238) adapted to accommodate a portion of a flexible portion (650.1) of the outlet barrier (650), wherein the flexible portion (650.1) of the outlet barrier (650) comprises the valve sealing surface, wherein the open configuration of the flow communication unit further comprises the enlarged channel inlet (238) accommodating the portion of the flexible portion (650.1) of the outlet barrier in the forced configuration, wherein the outlet barrier seal (653) is not provided.

Embodiment: FIG. 7

Proximal Support Member

52. The flow communication unit according to any of embodiments 1, 3 and 6-10, wherein the flow communication unit further comprises a proximal support member (797) comprising a proximal end (797.9) and a proximal portion adapted (797.10) to support the proximal valve member (798).

53. The flow communication unit according to embodiment 52, wherein the proximal support member (797) is rigid, wherein the proximal valve member (798) is a self-contained valve (798) comprising a first valve member comprising a surface portion adapted to provide a first proximal valve sealing surface, and a second valve member comprising a surface portion adapted to provide a second proximal valve sealing surface, wherein a proximal fluid tight seal (798.2) can be provided between the first and the second proximal valve sealing surface.

54. The flow communication unit according to any of embodiments 52-53 wherein the proximal support member (797) is rigid, and wherein the proximal valve member comprises a skirt portion adapted to surround and fixedly engage the proximal portion (797.1) of the proximal support member (797).

55. The flow communication unit according to any of embodiments 53-54, wherein the self-contained valve (798) comprises a surface portion providing a portion of the inlet surface (241) for interfacing the drug delivery device (210), and wherein the self-contained valve (798) is flexible and can be changed from a normal configuration to a forced configuration, in response to a fluid pressure on the inlet surface (241).

56. The flow communication unit according to embodiment 55, wherein the flow communication unit (740) comprises a normally closed configuration, wherein the self-contained valve is in the normal configuration, and thereby provides the proximal fluid tight seal (798.2).

57. The flow communication unit according to embodiment 56, wherein the flow communication unit (740) comprises an open configuration, wherein the self-contained valve is in the forced configuration, and wherein the proximal fluid tight seal (798.2) is not provided.

58. The flow communication unit according to embodiment 57, wherein the proximal portion (797.1) of the proximal support member (797) comprises an enlarged channel portion adapted to receive a portion of a flexible portion (798.3) of the self-contained valve (798), wherein the flexible portion comprises a portion of the first and the second proximal valve sealing surface, wherein the flexible portion axially deflects into the enlarged channel portion, in response to the self-contained valve changes from the normal to the forced configuration, and wherein the proximal portion (797.1) is adapted to provide a stop for the axial deflection, and thereby define the maximum deflection.

59. The flow communication unit according to any of embodiments 52-58, wherein the proximal support member (797) further comprises a support portion (797.5) adapted to be supported by the drug delivery device (210), and thereby provide support for the flow communication unit in relation to the drug delivery device (210).

Proximal Support Member —Distal Portion/Outlet Barrier

60. The flow communication unit according to any of embodiments 52-59, wherein the proximal support member (797) comprises a distal end (797.11) and a distal portion (797.12) adapted to support the outlet barrier (750).

61. The flow communication unit according to embodiment 60, wherein the proximal support member (797) is rigid, and wherein the distal portion (797.12) of the proximal support member (797) comprises a surface portion defining the first outlet valve member (754) adapted to provide a seat sealing surface, wherein outlet barrier (750) comprises a surface portion defining the second outlet valve member (755) adapted to provide a valve sealing surface, and wherein the outlet barrier seal (753) can be provided between the valve sealing surface and the seat sealing surface.

62. The flow communication unit according to any of embodiments 60-61, wherein the outlet barrier (750) comprises an inner surface portion for interfacing the distal portion (797.12) of proximal support member (797), and wherein the outlet barrier (750) is flexible and can be changed from a normal configuration to a forced configuration, in response to a fluid pressure on the inner surface portion.

63. The flow communication unit according to embodiment 62, wherein the normally closed configuration of the flow communication unit (740) further comprises, the outlet barrier being in the normal configuration and provides the outlet barrier seal (753).

64. The flow communication unit according to any of embodiments 52-63, wherein the proximal support member (797) provides a proximal portion of the first channel (247).

65. The flow communication unit according to embodiment 64, wherein the proximal portion of the first channel (247) extends from the proximal end (797.9) to an intermediate position (797.13).

66. The flow communication unit according to embodiment 65, wherein a distal portion of the first channel (247) is provided between the distal portion (797.12) and the outlet barrier (750), and wherein the distal portion of the first channel extends from the intermediate position (797.13) to the outlet (749).

Intermediate Valve Member

67. The flow communication unit according to any of the embodiments 1, 6-10, 52-66, wherein the outlet barrier (750) provides an intermediate valve member (750.2).

68. The flow communication unit according to embodiment 67, wherein the distal portion (797.12) of the proximal support member (797) is adapted to support the intermediate valve member (750.2).

69. The flow communication unit according to embodiment 68, wherein the distal portion (797.12) of the proximal support member (797) comprises a surface portion defining an intermediate valve seat (750.3) adapted to provide an intermediate seat sealing surface, wherein the intermediate valve member (750.2) comprises a surface portion adapted to provide an intermediate valve sealing surface, and wherein an intermediate fluid tight seal can be provided between the intermediate valve sealing surface and the intermediate seat sealing surface.

70. The flow communication unit according to any of embodiments 67-69, wherein the intermediate valve member (750.2) comprises an inner surface portion for interfacing the proximal support member (797), and wherein the intermediate valve member (750.2) is flexible and can be changed from a normal configuration to a forced configuration, in response to a fluid pressure on the inner surface portion.

71. The flow communication unit according to embodiment 70, wherein the normally closed configuration of the flow communication unit (740) further comprises, the intermediate valve member being in the normal configuration and provides the intermediate fluid tight seal.

72. The flow communication unit according to any of the embodiments 67-71, wherein the intermediate valve member is positioned in the distal portion of the first channel (247).

Distal Support Member

73. The flow communication unit according to any of the embodiments 1, 6-10, 52-72 comprising a distal support member (793).

74. The flow communication unit according to embodiment 73, wherein the distal support member (793) comprises a tubular portion (793.1) adapted to accommodate an accommodative portion of the outlet barrier (750), wherein the accommodative portion radially expands as the outlet barrier (750) changes from the normal to the forced configuration, and wherein the tubular portion (793.1) is adapted to provide a stop for the radial expansion, and thereby define the maximum expansion.

75. The flow communication unit according to embodiment 74, wherein the accommodative portion of the outlet barrier (750) comprises the second outlet valve member (755), wherein the open configuration of the flow communication unit (740) further comprises the outlet barrier being in the forced configuration, and wherein the outlet barrier seal (753) is not provided.

76. The flow communication unit according to embodiment 74, wherein the accommodative portion of the outlet barrier (750) comprises the intermediate valve member (750.2), wherein the open configuration of the flow communication unit (740) further comprises the outlet barrier being in the forced configuration, and wherein the intermediate fluid tight seal is not provided.

77. The flow communication unit according to any of embodiments 73-76, wherein the distal support member (793) further comprises a support portion adapted to be supported by the proximal support member, and thereby provide stability to the flow communication unit.

Distal Sealing Member

78. The flow communication unit according to any of the embodiments 1, 6-10, 52-77 comprising a distal sealing member (794) providing the outlet sealing member (746).

79. The flow communication unit according to embodiment 78, wherein the distal support member (793) is adapted to support the distal sealing member (794).

Embodiment: FIG. 8

Proximal Valve Member

80. The flow communication unit according to any of embodiments 1, 3 and 6-10, wherein the proximal valve member further comprises a support portion adapted to be supported by the drug delivery device (210), and thereby provide support for the flow communication unit in relation to the drug delivery device (210).

81. The flow communication unit according to any of embodiments 6-10, 80, wherein the proximal valve member is adapted to fit into an adapter top (290) having a retaining member on an inner surface, wherein the proximal valve member comprises a planar distal surface, and a recess adapted to receive the retaining member when the proximal valve member is inserted into the adaptor top (290), and whereby the distal surface remains planar to allow close contact with another planar surface.

Proximal Support Member

82. The flow communication unit according to any of embodiments 1 and 6-10, 80-81, wherein the flow communication unit further comprises a proximal support member (897) comprising a proximal end (897.9) and a proximal portion adapted (897.10) to support the proximal valve member (898).

83. The flow communication unit according to embodiment 82, wherein the proximal support member (897) is rigid, wherein the proximal valve member (898) is a self-contained valve (898) comprising a first valve member comprising a surface portion adapted to provide a first proximal valve sealing surface, and a second valve member comprising a surface portion adapted to provide a second proximal valve sealing surface, wherein a proximal fluid tight seal (898.2) can be provided between the first and the second proximal valve sealing surface.

84. The flow communication unit according to any of embodiments 82-83, wherein the proximal support member (897) is rigid with a planar proximal surface, and wherein the self-contained valve comprises a substantially planar distal surface, and wherein the proximal support member is adapted to transfer a compression force to the self-contained valve (898), and wherein the self-contained valve is adapted to transfer a compression force to the drug delivery device.

85. The flow communication unit according to any of embodiments 82-84, wherein the proximal support member (897) is rigid, and wherein the proximal support member is adapted to fit into an adaptor top (290) having a retaining member on an inner surface, and wherein the proximal support member comprises a planar proximal surface adapted to be supported by the retaining member, and whereby the proximal surface can be retained in close contact with a distal planar surface of the self-contained valve (898), when the proximal support member (897) and the self-contained valve (898) are inserted into the adaptor top (290).

86. The flow communication unit according to any of embodiments 80-85, wherein the proximal support member (897) is rigid and provides a proximal portion of the first channel (247).

87. The flow communication unit according to embodiment 86, wherein the proximal portion of the first channel (247) provided by the proximal support member, extends from the proximal end (897.9) of the proximal support member (897).

88. The flow communication unit according to any of embodiments 82-87, wherein the self-contained valve (898) comprises a surface portion providing a portion of the inlet surface (241) for interfacing the drug delivery device (210), and wherein the self-contained valve (898) is flexible and can be changed from a normal configuration to a forced configuration, in response to a fluid pressure on the inlet surface (241).

89. The flow communication unit according to embodiment 88, wherein the flow communication unit (840) comprises a normally closed configuration, wherein the self-contained valve is in the normal configuration, and thereby provides the proximal fluid tight seal (898.2).

90. The flow communication unit according to embodiment 89, wherein the flow communication unit (840) comprises an open configuration, wherein the self-contained valve is in the forced configuration, and wherein the proximal fluid tight seal (898.2) is not provided.

91. The flow communication unit according to embodiment 90, wherein the proximal portion (897.1) of the proximal support member (897) comprises an enlarged channel portion adapted to receive a portion of a flexible portion (898.3) of the self-contained valve (898), wherein the flexible portion comprises a portion of the first and the second proximal valve sealing surface, wherein the portion of the flexible portion axially deflects into the enlarged channel portion, in response to the self-contained valve changes from the normal to the forced configuration, and wherein the proximal portion (797.1) is adapted to provide a stop for the axial deflection, and thereby define the maximum deflection.

Intermediate Valve Member

92. The flow communication unit according to any of the embodiments 1, 6-10, 80-91 comprising an intermediate valve member (894).

93. The flow communication unit according to embodiment 92, wherein the proximal support member (897) comprises a distal end (897.11) and a distal portion (897.12) adapted to support the intermediate valve member (894).

94. The flow communication unit according to embodiment 93, wherein the proximal support member (897) is rigid, and wherein the distal portion (897.12) of the proximal support member (897) comprises a surface portion defining an intermediate valve seat (897.6) adapted to provide an intermediate seat sealing surface, wherein the intermediate valve member (894) comprises a surface portion adapted to provide an intermediate valve sealing surface, and wherein an intermediate fluid tight seal (897.8) can be provided between the intermediate valve sealing surface and the intermediate seat sealing surface.

95. The flow communication unit according to any of embodiments 86-94, wherein the proximal portion of the first channel (247) extends from the proximal end (897.9) to the distal end (897.11).

96. The flow communication unit according to any of embodiments 92-95, wherein the intermediate valve member (894) comprises a proximal surface portion for interfacing the distal portion of the proximal support member (897), and wherein the intermediate valve member (894) is flexible and can be changed from a normal configuration to a forced configuration, in response to a fluid pressure on the proximal surface.

97. The flow communication unit according to embodiment 96, wherein the normally closed configuration of the flow communication unit (840) further comprises, the intermediate valve member being in the normal configuration and provides the intermediate fluid tight seal (897.8).

Distal Support Member

98. The flow communication unit according to any of the embodiments 1, 6-10, 80-97 comprising a distal support member (893).

99. The flow communication unit according to embodiment 98, wherein the distal support member (893) is rigid and provides a distal portion of the first channel (247).

100. The flow communication unit according to embodiment 99, wherein the distal support member (893) comprises an enlarged channel portion (893.1) adapted to receive a portion of a flexible portion (894.2) of the intermediate valve member (894), wherein the flexible portion (894.2) of the intermediate valve member (894) comprises the intermediate valve sealing surface (894.1), wherein the open configuration of the flow communication unit (840) further comprises the enlarged channel portion (893.1) receiving the portion of the flexible portion of the intermediate valve member in the forced configuration, wherein the intermediate fluid tight seal (897.3) is not provided.

101. The flow communication unit according to any of embodiments 98-100, wherein the proximal support member (897), the intermediate valve member (894) the distal support member (893) provides a unit, wherein a portion of the intermediate valve member is clamped between the support members, and wherein the support members are welded together by ultra-sound.

102. The flow communication unit according to embodiments 101, wherein the clamped portion is fixed and the unclamped portion is flexible and adapted to be moved between the normal and the forced configuration.

Outlet Barrier

103. The flow communication unit according to any of the embodiments 1, 6-10, 80-102, wherein the distal support member (893) comprises a distal end and a distal portion adapted to support the outlet barrier (850).

104. The flow communication unit according to embodiment 103, wherein the distal support member (893) is rigid, wherein the outlet barrier (850) is a self-contained valve (850) comprising a first valve member (854) comprising a surface portion adapted to provide a first proximal valve sealing surface, and a second valve member (855) comprising a surface portion adapted to provide a second proximal valve sealing surface, wherein a proximal fluid tight seal (853) can be provided between the first and the second proximal valve sealing surface.

105. The flow communication unit according to any of embodiments 103-104, wherein the self-contained valve (850) comprises a proximal surface portion for covering the first channel (247), and wherein the self-contained valve (850) is flexible and can be changed from a normal configuration to a forced configuration, in response to a fluid pressure in the first channel, and thereby on the proximal surface portion of the self-contained valve.

106. The flow communication unit according to embodiment 105, wherein the normally closed configuration of the flow communication unit (840) comprises the self-contained valve is in the normal configuration, and thereby provides the proximal fluid tight seal (853).

107. The flow communication unit according to embodiment 106, wherein the open configuration of the flow communication unit (840) comprises the self-contained valve is in the forced configuration, and wherein the proximal fluid tight seal (853) is not provided.

108. The flow communication unit according to embodiment 107, wherein the proximal portion (897.1) of the proximal support member (897) comprises an enlarged channel portion adapted to receive a portion of a flexible portion (898.3) of the self-contained valve (898), wherein the flexible portion comprises a portion of the first and the second proximal valve sealing surface, wherein the portion of the flexible portion axially deflects into the enlarged channel portion, in response to the self-contained valve changes from the normal to the forced configuration, and wherein the proximal portion (897.1) is adapted to provide a stop for the axial deflection, and thereby define the maximum deflection.

109. The flow communication unit according to any of embodiments 103-108, wherein the distal support member (893) is rigid with a planar distal surface, and wherein the self-contained valve comprises a substantially planar proximal surface, and wherein the distal support member is adapted to transfer a compression force to the outlet barrier (850), and wherein the outlet barrier is adapted to transfer a compression force to an adaptor top (290).

110. The flow communication unit according to any of embodiments 103-109, wherein the proximal support member (897) is rigid, and wherein the proximal support member, the intermediate valve member, the distal support member and the outlet barrier are adapted to fit into an adaptor top (290) having a retaining member on an inner surface, and wherein the proximal support member comprises a planar proximal surface adapted to be supported by the retaining member, and whereby the proximal surface can be retained in close contact with a the distal planar surface of the proximal valve member (898), when all members are inserted into the adaptor top (290).

111. The flow communication unit according to any of embodiments 103-110, wherein the proximal support member (897), the intermediate valve member (894) and the distal support member (893) provides a unit, wherein a portion of the intermediate valve member is clamped between the support members, and wherein the unit is adapted to be fitted into an adaptor top (290) having a unit retaining member adapted to retain the unit in a compressed state.

112. The flow communication unit according to embodiment 111, wherein the outlet barrier and the unit are adapted to be retained in a compressed state in the adaptor top, wherein the retaining member can transfer a compression force to the unit, and the unit can transfer the compression force to a retaining surface of the adaptor top (290).

113. The flow communication unit according to embodiment 111, wherein the outlet barrier and the unit are adapted to be retained in a compressed state in the adaptor top, wherein the proximal valve member is adapted to be fitted into the adaptor top in a compressed state, and wherein the adaptor top comprises a device retaining member on an inner surface, wherein the device retaining member is adapted to connect the adaptor top to the drug retaining device, wherein the proximal valve member is supported by the drug delivery device in a compressed state.

114. The flow communication unit according to any of embodiments 103-113, wherein the flow conducting device (230) comprises an enlarged channel inlet (238) adapted to receive a portion of a flexible portion (850.1) of the self-contained valve (850), wherein the flexible portion (850.1) of the self-contained valve (850) comprises a portion of the outlet barrier seal (853), wherein the open configuration of the flow communication unit further comprises the enlarged channel inlet (238) receiving the portion of the flexible portion (850.1) of the outlet barrier in the forced configuration, wherein the outlet barrier seal (853) is not provided.

115. The flow communication unit according to any of the previous embodiments 104-113, wherein the outlet barrier (850) provides the outlet sealing member (846).

Embodiment: FIG. 9

Proximal Valve Member

116. The flow communication unit according to any of embodiments 1, 3 and 6-9, wherein the proximal valve member provides the channel inlet (948) in a normal configuration, wherein the valve is closed.

117. The flow communication unit according to any of embodiments 6-9, 116, wherein the proximal valve member provides a channel passage in a forced configuration, wherein the valve is open.

118. The flow communication unit according to any of embodiments 6-9, 116-117, wherein the proximal valve member comprises a distal surface portion for interfacing a movable channel member, and wherein the proximal valve member (998) is flexible and can be changed from a normal configuration to a forced configuration, in response to a pressure from the movable channel member on the distal surface portion.

Proximal Support Member

119. The flow communication unit according to any of embodiments 1, 6-9, and 116-118, wherein the flow communication unit further comprises a proximal support member (997) comprising a proximal end (997.9) and a proximal portion adapted (997.10) to support the proximal valve member (998).

120. The flow communication unit according to embodiment 119, wherein the proximal support member (997) is rigid, wherein the proximal valve member (998) is a self-contained valve (998) comprising a first valve member comprising a surface portion adapted to provide a first proximal valve sealing surface, and a second valve member comprising a surface portion adapted to provide a second proximal valve sealing surface, wherein a proximal fluid tight seal (998.2) can be provided between the first and the second proximal valve sealing surface.

121. The flow communication unit according to any of embodiments 119-120, wherein the proximal support member (997) is rigid, and wherein the self-contained valve (998) comprises a skirt portion adapted to surround and/or be surrounded by the proximal portion (997.1) of the proximal support member (997), whereby the self-contained valve and the proximal support member are fixedly engaged to each other.

122. The flow communication unit according to any of embodiments 119-121, wherein the self-contained valve (998) comprises a proximal surface portion providing a portion of the inlet surface (241) for interfacing the drug delivery device (210), and a distal surface portion for interfacing a movable channel member, wherein the self-contained valve (998) is flexible and (i) wherein the self-contained valve can be changed from a normal configuration to a forced configuration, in response to a pressure from the movable channel member on the distal surface portion, and (ii) wherein the movable channel member supports the self-contained valve (998) in the normal configuration, in response to a fluid pressure on the inlet surface (241), and whereby the fluid tight seal (998.2) remains tight.

123. The flow communication unit according to any of embodiments 119-122, wherein the flow communication unit (940) comprises a normally closed configuration, wherein the self-contained valve is in the normal configuration, and thereby provides the proximal fluid tight seal (998.2).

124. The flow communication unit according to any of embodiment 119-123, wherein the flow communication unit (940) comprises an open configuration, wherein the self-contained valve is in the forced configuration and the channel inlet (948) is provided by the movable channel member, and wherein the proximal fluid tight seal (998.2) is not provided.

125. The flow communication unit according to any of embodiments 119-124, wherein the proximal portion (997.1) of the proximal support member (997) is adapted to receive a portion of the self-contained valve (998) defining a channel seat portion, wherein the channel seat portion is adapted to provide a seat for a proximal portion of the movable channel member in a distal position, and wherein the self-contained valve is in the forced configuration.

126. The flow communication unit according to any of embodiments 119-125, wherein the proximal portion (997.1) of the proximal support member (997) is adapted to receive a portion of the self-contained valve (998) defining a channel seat portion, wherein the channel seat portion is adapted to provide a seat for a distal portion of the movable channel member in a proximal position, wherein the movable channel member extends across the self-contained valve (998), wherein the self-contained valve (998) provides a seal around the movable channel member, and wherein the self-contained valve is in the forced configuration.

127. The flow communication unit according to any of embodiments 119-126, wherein the proximal support member (997) further comprises a support portion (997.5) adapted to be supported by the drug delivery device (210), and thereby provide support for the flow communication unit in relation to the drug delivery device (210).

Proximal Support Member —Distal Portion

128. The flow communication unit according to any of embodiments 119-127, wherein the proximal support member (997) comprises a distal end (997.11) and a distal portion (997.12) adapted to support the outlet barrier (750).

Distal Support Member

129. The flow communication unit according to any of embodiments 1, 6-9, 116-128 further comprising a distal support member (993).

130. The flow communication unit according to embodiment 129, wherein the proximal support member (997) comprises a tubular portion adapted to accommodate the distal support member (993), wherein the distal support member (993) is movably arranged within the tubular portion, and wherein the distal support member is adapted to be moved between a distal position and a proximal position.

131. The flow communication unit according to any of embodiments 129-130, wherein the distal support member (993) comprises a proximal end (993.9) and a proximal portion (993.10) comprising a movable channel member.

132. The flow communication unit according to any of embodiments 129-131, wherein the distal support member (993) comprises a distal end (993.11) and a distal portion (993.12) adapted to support the outlet barrier (950).

133. The flow communication unit according to embodiment 129, wherein the distal support member (993) is rigid, and wherein the distal portion (993.12) of the distal support member (993) comprises a surface portion defining the first outlet valve member (954) adapted to provide a seat sealing surface, wherein outlet barrier (950) comprises a surface portion defining the second outlet valve member (955) adapted to provide a valve sealing surface, and wherein the outlet barrier seal (953) can be provided between the valve sealing surface and the seat sealing surface.

134. The flow communication unit according to any of embodiments 129-133, wherein the outlet barrier (950) comprises an inner surface portion for interfacing the distal portion (993.12) of the distal support member (993), and wherein the outlet barrier (950) is flexible and can be changed from a normal configuration to a forced configuration, in response to a fluid pressure on the inner surface portion.

135. The flow communication unit according to embodiment 134, wherein the normally closed configuration of the flow communication unit (940) further comprises, the outlet barrier being in the normal configuration and provides the outlet barrier seal (953).

136. The flow communication unit according to any of embodiments 131-135, wherein the proximal portion (993.10) of the distal support member (993) provides a proximal portion of the first channel (247).

137. The flow communication unit according to embodiment 136, wherein the proximal portion of the first channel (247) extends from the proximal end (993.9) to an intermediate position (993.13).

138. The flow communication unit according to embodiment 137, wherein a distal portion of the first channel (247) is provided between the distal portion (993.12) and the outlet barrier (950), and wherein the distal portion of the first channel extends from the intermediate position (997.13) to the outlet (949).

139. The flow communication unit according to any of the embodiments 129-138, further comprising a biasing member (994) adapted to bias the distal support member (993) towards the distal position. 140. The flow communication unit according to embodiment 139, wherein the biasing member (994) is positioned between a distal surface of the proximal support member (998) and a proximal surface of the distal support member (993).

141. The flow communication unit according to embodiment 140, wherein the biasing member (994) is a compression spring.

Intermediate Valve Member

142. The flow communication unit according to any of the embodiments 1, 6-9, 116-141, wherein the outlet barrier (950) provides an intermediate valve member (950.2).

143. The flow communication unit according to embodiment 142, wherein the distal portion (993.12) of the distal support member (993) is adapted to support the intermediate valve member (950.2).

144. The flow communication unit according to embodiment 143, wherein the distal portion (993.12) of the distal support member (993) comprises a surface portion defining an intermediate valve seat (993.14) adapted to provide an intermediate seat sealing surface, wherein the intermediate valve member (950.2) comprises a surface portion adapted to provide an intermediate valve sealing surface, and wherein an intermediate fluid tight seal can be provided between the intermediate valve sealing surface and the intermediate seat sealing surface.

145. The flow communication unit according to any of embodiments 142-144, wherein the intermediate valve member (950.2) comprises an inner surface portion for interfacing the distal support member (993), and wherein the intermediate valve member (950.2) is flexible and can be changed from a normal configuration to a forced configuration, in response to a fluid pressure on the inner surface portion.

146. The flow communication unit according to embodiment 145, wherein the normally closed configuration of the flow communication unit (940) further comprises, the intermediate valve member being in the normal configuration and provides the intermediate fluid tight seal.

147. The flow communication unit according to any of the embodiments 142-146, wherein the intermediate valve member is positioned in the distal portion of the first channel (247), and provides additional safety.

Outlet Barrier

148. The flow communication unit according to any of the embodiments 1, 6-9, 116-147, wherein the outlet sealing member (946) is provided by the outlet barrier (950).

Embodiment: FIG. 10

149. The flow communication unit (1040, 1140, 1240) according to any of the embodiments 1, 3 and 4, wherein the flow communication unit further comprises:

a central portion (1198, 1298) extending from the inlet surface (241) to the outlet surface (242), wherein the central portion provides a portion of the inlet surface and the outlet surface, and wherein the central portion comprises the first flow channel (247), the central portion further comprises a side surface extending in a direction between the inlet and the outlet surface (242), wherein the channel outlet (1049, 1149) and the first outlet valve member (1054, 1154, 1254) is provided in the side surface, and wherein the first outlet valve member surrounds the channel outlet (1049, 1149, 1249), wherein the outlet barrier (1050, 1150, 1250) surrounds the central portion and provides the second outlet valve member (1055, 1155, 1255), wherein the outlet barrier (1050, 1150, 1250) is movably arranged and can be moved between a distal position and a proximal position, wherein the outlet surface (242) can be arranged in the connected configuration, when the outlet barrier (1050, 1150, 12050) is positioned in the proximal position, wherein the outlet surface (242) can be arranged in the unconnected configuration, when the outlet barrier (1050, 1150, 1250) is positioned in the distal position, wherein a circumferential portion (1197, 1297) connected to the central portion provides the intermediate surfaces (243, 244) extending between the inlet surface and the outlet surface, wherein the circumferential portion comprises a portion of the inlet and the outlet surface, wherein the inlet surface, the outlet surface and the intermediate surfaces define the outer surface and confines the interior space (245) of the flow communication unit, for the outlet surface (242) being in any of the connected and the unconnected configurations, wherein the outlet barrier is positioned proximally or distally, wherein the outlet sealing member (1046, 1146, 1246) is provided in the side surface of the central portion, and wherein the outlet sealing member surrounds the channel outlet (1049, 1149, 1249), whereby the outlet sealing member provides a portion of the outlet surface (242) in the connected configuration, wherein the outlet barrier (1050, 1150, 1250) provides a portion of the outlet surface (242), wherein the outlet surface provided by the outlet barrier is flush with the outlet portions provided by the central and the circumferential portion, when the outlet surface is in the unconnected configuration, whereby it is easier to keep the outlet surface clean, and wherein the outlet surface provided by the outlet barrier is depressed relative to outlet surface portions provided by the central and the circumferential portion, when the outlet surface is in the connected configuration, wherein the second outlet valve member (1055, 1155, 1255) is adapted to cooperate with the first outlet valve member (1054, 1154) to provide an outlet barrier seal (1053, 1153, 1253), wherein the outlet barrier is adapted for being in:

(i) a closed configuration, wherein the outlet surface is in the unconnected configuration, whereby the outlet barrier is in the distal position, and whereby the outlet barrier seal is adapted to reduce the entrance of contaminations, and (ii) a flow configuration, wherein the outlet surface is in the connected configuration, whereby the outlet barrier is in the proximal position, whereby the outlet barrier (1050, 1150, 1250) is adapted to allow a drug contained in the first channel (247) to flow downstream from the channel inlet and out of the channel outlet (1049, 1149, 1249), in response to the pressure in the first channel (247) being above the first threshold;

wherein the flow communication unit is further adapted for being in:

(i) the unconnected configuration, in response to disconnecting the flow communication unit from the flow conducting device, and wherein the outlet barrier (1050, 1150, 1250) is allowed to be in the closed configuration, and (ii) the connected configuration, in response to connecting the flow communication unit to the flow conducting device (230), wherein the outlet barrier is allowed to be in the flow configuration, wherein the outlet sealing member (1046, 1146, 1246) is arranged to be able to contact the flow conducting device to provide the channel seal (1060, 1160, 1260) downstream to the channel outlet (1049) to allow flow communication between the channel outlet (1049, 1149, 1249) and the flow conducting device, wherein the channel outlet (1049, 1149, 1249) for the first channel is arranged at the outlet surface (242) of the flow communication unit; and wherein a combined flow channel (267) can be provided between the drug delivery device (210), the first channel (247) and the flow conducting device (230) with the channel seal arranged downstream to the channel outlet, when the channel inlet is arranged in flow communication with the drug delivery device and the flow communication unit (1040, 1140, 1240) is in the connected configuration;

whereby the flow communication unit (1040, 1140, 1240) is adapted to enable the extended use of the multi-use drug delivery device, and whereby the flow communication unit is adapted to inhibit microbial entrance in the multi-use drug delivery device during the extended use.

150. The flow communication unit (1040, 1240) according to embodiment 149 further comprising an outlet barrier locking member (1050.10, 1250.10) adapted to be released by the flow conducting device (230) upon connection, wherein the outlet barrier is further adapted for being in:

(i) the closed configuration, wherein the outlet surface is in the unconnected configuration, wherein the outlet barrier is locked by the outlet barrier locking member (1050.10, 1250.10) in the distal position, and (ii) a flow configuration, wherein the outlet surface is in the connected configuration, wherein the outlet barrier is released and allowed to be moved to the proximal position.

151. The flow communication unit (1040, 1240) according to embodiment 150, wherein the barrier locking member (1050.10, 1250.10) is further adapted for being released by a connecting member (230.10) of the flow conducting device (230).

The invention claimed is:

1. A drug delivery system comprising:
a multiple injection drug delivery device,
a flow conducting device, and
a flow communication unit for establishing flow communication from the multiple injection drug delivery device adapted for extended use, to the flow conducting device,
wherein the drug delivery device comprises a reservoir comprising multiple doses of a liquid drug formulation, wherein the reservoir is adapted to pressurize the liquid drug formulation, wherein the flow conducting device is adapted for conducting the drug for subcutaneous injection of a subject, wherein the flow communication unit comprises:
an inlet surface for interfacing the drug delivery device,
an outlet surface configured for being in:
(i) a connected/flow configuration, wherein the outlet surface allows the flow communication unit and the flow conducting device to be connected, and wherein the outlet surface is adapted for interfacing the flow conducting device, and
(ii) an unconnected/closed configuration, wherein the outlet surface allows the flow communication unit and the flow conducting device to be unconnected, and wherein the outlet surface is adapted for inhibiting the entrance of contaminations into an interior space of the flow communication unit;
intermediate surfaces extending between the inlet surface and the outlet surface, wherein the inlet surface, the outlet surface and the intermediate surfaces define an outer surface and confines the interior space of the flow communication unit, for the outlet surface being in any of the connected and the unconnected configurations,
an outlet sealing member providing a portion of the outlet surface, for the outlet surface being in the connected configuration, wherein the outlet sealing member is adapted for contacting the flow conducting device to establish a fluid tight channel seal,
a first flow channel comprising a channel inlet adapted for providing flow communication with the drug delivery device, and a channel outlet adapted for providing flow communication with the flow conducting device,
a first outlet valve member,
an outlet barrier comprising a second outlet valve member adapted to cooperate with the first outlet valve member, wherein the outlet barrier provides a portion of the outlet surface, and wherein the outlet barrier is configured for being in:
(i) a unconnected/closed configuration, wherein the outlet surface is in the unconnected configuration, wherein the second outlet valve member is adapted to cooperate with the first outlet valve member to provide an outlet barrier seal, and wherein the outlet barrier seal is adapted to inhibit the entrance of contaminations through the channel outlet and into the first channel, and
(ii) a connected/flow configuration, wherein the outlet surface is in the connected configuration, wherein the second outlet valve member is adapted to cooperate with the first outlet valve member to allow a drug contained in the first channel to flow downstream from the channel inlet and out of the channel outlet, in response to a pressure in the first channel being above a first threshold;
wherein the flow communication unit is further adapted for being in:
(i) an unconnected/closed configuration, in response to disconnecting the flow communication unit from the flow conducting device, wherein the outlet surface is in the unconnected/closed configuration, and wherein the outlet barrier is in the unconnected/closed configuration, and (ii) a connected/flow configuration, in response to connecting the flow communication unit to the flow conducting device, wherein the outlet surface is in the connected/flow configuration, wherein the outlet barrier is in the connected/flow configuration, wherein the outlet sealing member is arranged to be able to contact the flow conducting device to provide the channel seal downstream to the channel outlet of the first flow channel, and thereby adapted to allow flow communication between the channel outlet and the flow conducting device, wherein the channel outlet is arranged at the outlet surface of the flow communication unit; and wherein a combined flow channel can be provided between the drug delivery device, the first flow channel and the flow conducting device with the channel seal arranged downstream to the channel outlet, in response to the channel inlet being arranged in flow communication with the drug delivery device and the flow communication unit being connected to the flow conducting device;

whereby the flow communication unit is adapted to enable the extended use of the multiple injection drug delivery device, and whereby the flow communication unit is adapted to inhibit microbial entrance in the multiple injection drug delivery device during the extended use.

2. The drug delivery system according to claim 1, wherein the flow communication unit further comprises a unidirectional valve arranged along the first channel and adapted for guiding the flow downstream and inhibiting upstream flow towards the drug delivery device.

3. The drug delivery system according to claim 1, wherein the outlet barrier provides the channel outlet.

4. The drug delivery system according to claim 1, wherein the flow communication unit further comprises a proximal valve member, adapted to allow a flow from the inlet towards the outlet and for preventing a reverse flow.

5. The drug delivery system according to claim 4, wherein the proximal valve member provides a portion of the inlet surface for interfacing the drug delivery device.

6. The drug delivery system according to claim 4, wherein the proximal valve member provides a portion of the intermediate surfaces extending between the inlet surface and the outlet surface.

7. The drug delivery system according to claim 4, wherein the portion of the intermediate surfaces is soft and provides a device sealing surface to seal against the drug delivery device.

8. The drug delivery system according to claim 4, wherein the proximal valve member provides the channel inlet.

9. The drug delivery system according to claim 1, wherein the flow communication unit further comprises a distal support member comprising a distal end and a distal portion adapted to support the outlet barrier, and wherein the distal support member further comprises a barrier operating member adapted to cooperate with the outlet barrier in regulating the tightness of the outlet barrier seal, wherein the outlet barrier comprises an actuator portion providing the outlet sealing member and movably arranged between a first position and a second position relative to the barrier operating member, and adapted to be configured in an:

(i) unconnected/closed configuration, wherein the outlet barrier is in the unconnected/closed configuration, wherein the unconnected/closed configuration of the outlet barrier further comprises the actuator portion being in the first position relative to the barrier operating member, whereby the second outlet valve member is adapted to cooperate with the first outlet valve member to provide the outlet barrier seal adapted to allow a drug contained in the first channel to flow downstream from the channel inlet and out of the channel outlet, in response to the pressure in the first channel being above a second threshold, wherein the second threshold defines the tightness of the outlet barrier seal in the unconnected/closed configuration and is larger than the first threshold, (ii) a connected/flow configuration, wherein the outlet barrier is in the connected/flow configuration, wherein the connected/flow configuration of the outlet barrier further comprises the actuator portion is in the second position relative to the barrier operating member, whereby the second outlet valve member is adapted to cooperate with the first outlet valve member to provide the outlet barrier seal adapted allow a drug contained in the first channel to flow downstream from the channel inlet and out of the channel outlet, in response to the pressure in the first channel being above the first threshold, wherein the first threshold defines the tightness of the outlet barrier seal in the connected/flow configuration.

10. The drug delivery system according to claim 9, wherein the actuator portion, is adapted to be manipulated from the first position to the second position, by the flow conducting device upon connection.

11. The drug delivery system according to claim 1, wherein the flow conducting device comprises a first connector adapted for connecting the flow conducting device to the flow communication unit, and an inlet surface for interfacing and contacting the outlet surface of the flow communication unit, wherein the inlet surface provides an outer surface of the flow conducting device.

12. The drug delivery system according to claim 11, wherein the flow conducting device further comprises an inlet sealing portion providing a portion of the inlet surface, and adapted for contacting the outlet sealing portion of the flow communication unit, whereby the inlet sealing portion is adapted to provide the fluid tight seal in the interface between the flow conducting device and the flow communication unit.

13. The drug delivery system according to claim 1, wherein the flow conducting device further comprises a second channel for conducting fluid having a channel inlet positioned at the inlet surface, and a channel outlet.

14. The drug delivery system according to claim 1, wherein the flow conducting device is in the form of a pen needle comprising a hub and a needle cannula, or in the form of an infusion set comprising a hub and a catheter.

* * * * *